United States Patent
Zhu et al.

(10) Patent No.: US 11,857,289 B2
(45) Date of Patent: Jan. 2, 2024

(54) SYSTEMS AND METHODS OF OPTIMIZING FUNCTIONAL IMAGES OF A LESION REGION USING GUIDED DIFFUSE OPTICAL TOMOGRAPHY

(71) Applicant: Washington University, St. Louis, MO (US)

(72) Inventors: Quing Zhu, St. Louis, MO (US); Mark Anastasio, St. Louis, MO (US); Shihab Uddin, St. Louis, MO (US)

(73) Assignee: Washington University, St. Louis, MO (US)

(*) Notice: Subject to any disclaimer, the term of this patent is extended or adjusted under 35 U.S.C. 154(b) by 285 days.

(21) Appl. No.: 16/649,743

(22) PCT Filed: Oct. 24, 2018

(86) PCT No.: PCT/US2018/057364
§ 371 (c)(1),
(2) Date: Mar. 23, 2020

(87) PCT Pub. No.: WO2019/084174
PCT Pub. Date: May 2, 2019

(65) Prior Publication Data
US 2020/0260960 A1 Aug. 20, 2020

Related U.S. Application Data

(60) Provisional application No. 62/576,188, filed on Oct. 24, 2017.

(51) Int. Cl.
*A61B 5/00* (2006.01)
*G16H 30/40* (2018.01)

(52) U.S. Cl.
CPC .......... *A61B 5/0073* (2013.01); *A61B 5/4312* (2013.01); *G16H 30/40* (2018.01)

(58) Field of Classification Search
CPC ..... A61B 5/0073; A61B 5/4312; G16H 30/40
See application file for complete search history.

(56) References Cited

U.S. PATENT DOCUMENTS

| | | | | |
|---|---|---|---|---|
| 2004/0215072 | A1* | 10/2004 | Zhu | G01S 15/899 600/407 |
| 2014/0364736 | A1* | 12/2014 | Huang | A61B 8/4477 600/447 |

(Continued)

OTHER PUBLICATIONS

Vavadi et al., "Automated data selection method to improve robustness of diffuse optical tomography for breast cancer imaging", Oct. 1, 2016, Biomedical Optics Express, vol. 7, No. 10, 4007-4020 (Year: 2016).*

(Continued)

*Primary Examiner* — Colin T. Sakamoto
*Assistant Examiner* — Andrew W Begeman
(74) *Attorney, Agent, or Firm* — Armstrong Teasdale LLP

(57) ABSTRACT

A system and method for generating at least one optimized functional images of a lesion region of a subject is provided. The system includes a diffuse optical tomography (DOT) device, and a computing device. The DOT device is configured to acquire lesion functional data of an imaging volume including the lesion region of the breast and reference functional data from a corresponding imaging volume including healthy tissue within a contralateral breast. The computing device is programmed to generate at least one functional image of the breast by reconstructing the functional data at the plurality of regions including the lesion region and the surrounding adjacent background region. The functional images may be reconstructed by an optimization method regularized a preliminary estimate generated by applying a truncated pseudoinverse matrix of a weight matrix to the functional data. The optimized functional images relate to levels of hemoglobin at the voxels.

20 Claims, 43 Drawing Sheets

(56) References Cited

U.S. PATENT DOCUMENTS

2015/0010223 A1 1/2015 Sapiro et al.
2016/0278715 A1 9/2016 Yu et al.

OTHER PUBLICATIONS

Habermehl et al., "Optimizing the regularization for image reconstruction of cerebral diffuse optical tomography", 2014, Journal of Biomedical Optics, vol. 19(9) (Year: 2014).*
Roy et al., "Truncated Newton's optimization scheme for absorption and fluorescence optical tomography: Part I theory and formulation", 1999, Optics Express, vol. 4, No. 10, 353-371 (Year: 1999).*
Zhu et al., "Assessment of Functional Differences in Malignant and Benign Breast Lesions and Improvement of Diagnostic Accuracy by Using US-guided Diffuse Optical Tomography in Conjunction with Conventional US", Aug. 2016, Radiology, vol. 280, No. 2, 387-397 (Year: 2016).*
Li et al., "Tomographic optical breast imaging guided by three-dimensional mammography", 2003, Applied Optics, vol. 42, No. 25, 5181-5190 (Year: 2003).*
Bohringer et al., "Time-Domain and Spectral-Domain Optical Coherence Tomography in the Analysis of Brain Tumor Tissue", 2006, Lasers in Surgery and Medicine, 38, 588-597 (Year: 2006).*
Shih Kang et al. A Hardware Design for Portable Continuous Wave Diffuse Optical Tomography. Database Theory and Application, Bio-Science and Bio-Technology, International Conferences, DTA and BSBT 2010, Held as Part of the Future Generation Information Technology Conference, FGIT 2010, Jeju Island, Korea, Dec. 13-15, 2010, pp. 8-18.
International Search Report and Written Opinion for PCT/US2018/057364, dated Feb. 7, 2019, 8 pages.

* cited by examiner

SYSTEMS AND METHODS OF OPTIMIZING FUNCTIONAL IMAGES OF A LESION REGION USING GUIDED DIFFUSE OPTICAL TOMOGRAPHY

CROSS-REFERENCE TO RELATED APPLICATION

This application is a National Stage application of International Application No. PCT/US2018/057364, filed on Oct. 24, 2018, entitled "SYSTEMS AND METHODS OF OPTIMIZING FUNCTIONAL IMAGES OF A LESION REGION USING GUIDED DIFFUSE OPTICAL TOMOGRAPHY", which claims priority to U.S. Provisional Application Ser. No. 62/576,188, filed Oct. 24, 2017, entitled "METHODS OF IMAGE RECONSTRUCTION," each of which is hereby incorporated herein by reference in its entirety.

GOVERNMENTAL SUPPORT

This invention was made with government support under grant number IEB002136 awarded by National Institutes of Health. The government has certain rights in the invention.

BACKGROUND

The field of the disclosure relates generally to imaging systems and methods, and more particularly to imaging systems and methods for generating optimized functional images of a lesion region of a subject using diffuse optical tomography (DOT).

Breast cancer is the most common cancer in women worldwide, with approximately 1.67 million new cases each year. Although breast cancer screening has helped greatly in reducing breast cancer mortality and treatment has been improved, more than half a million patients still die from this disease annually. Breast cancer has different histologic subtypes with different grades, growth rates, and metabolic activity levels, resulting in a wide range of functional differences. Additionally, benign breast disease encompasses a heterogeneous group of lesions that vary in vascular content, proliferative index, and metabolic activity, all of which may or may not be associated with future risk of developing into breast cancer. While the characteristics of malignant and benign breast lesions are well established by conventional imaging techniques, the overlapping appearances of the images result in approximately one million image-guided breast biopsies each year in the United States, most of which yield results of being benign tumors.

The current diagnostic imaging paradigm results in a disproportionate number of biopsy recommendations of benign lesions. The positive predictive value of a screen having detected abnormality and recommended for biopsy is just over 25%, resulting in nearly 75% of unnecessary biopsy recommendations. Despite many attempts to improve this situation, success has been limited.

DOT and diffuse optical spectroscopy (DOS) have been explored for diagnosis of breast cancers. Due to intensive light scattering in tissue, lesion localization and light quantification accuracy is an ongoing challenge. Further, because of the correlated nature of diffused light measured at multiple optical source and detector positions, as well as measurement noise, the DOT reconstruction problem is typically underdetermined and similarly poses various challenges.

Previous systems have made use of a variety of image reconstruction methods to improve target reconstruction accuracy in DOT. One class of previous systems incorporates prior information into an iterative image reconstruction method using an initial image estimate to address the DOT reconstruction problem. For example, one previous system implemented a two-step reconstruction using a Genetic Algorithm (GA) to find a suitable initial image estimate that was subsequently refined by use of a conjugate gradient (CG) method. Although the incorporation of the initial image estimate resulted in improved target quantification as compared to CG with zero initial estimate, the GA estimation was time-consuming and optimal CG stopping criteria was difficult to specify.

BRIEF DESCRIPTION

In one aspect, a system for generating an optimized functional image of a lesion region of a breast is provided. The system includes a diffuse optical tomography (DOT) device configured to acquire lesion functional data from the lesion region of the breast and to acquire reference functional data from a healthy tissue region of a contralateral breast. The system further includes a computing device in communication with the DOT device. The computing device is programmed to transform the lesion functional data and the reference functional data to produce perturbation data that represents a normalized difference between the lesion functional data and the reference functional data. The computing device is further programmed to generate a preliminary estimate of the functional image by applying a pseudoinverse matrix of a weight matrix to the perturbation data. The pseudoinverse matrix may be a truncated pseudoinverse matrix. The weight matrix includes a plurality of elements representing system measurement sensitivity and distribution of diffused optical waves in a homogenous medium. The computing device is also programmed to generate each optimized functional image by iteratively optimizing successive estimates of the functional image regularized by the preliminary estimate of the functional image weighted by a regularization parameter. A value of the optimized functional image at each voxel in the lesion region is indicative of a hemoglobin concentration at that voxel. The computing device is further programmed to display the at least one optimized functional image.

In another aspect, a computer-implemented method of generating at least one optimized functional image of a lesion region of a breast of a subject is provided. The method includes receiving, using a computing device, a plurality of measurements from a diffuse optical tomography (DOT) device. The plurality of measurements include lesion functional data from the lesion region of the breast and reference functional data from a healthy tissue region of a contralateral breast. The method further includes transforming, using the computing device, the lesion functional data and the reference functional data to produce perturbation data. The perturbation data includes a normalized difference between the lesion functional data and the reference functional data. The method also includes generating, using the computing device, a preliminary estimate of the functional image by applying a pseudoinverse matrix of a weight matrix to the perturbation data. The pseudoinverse matrix may a truncated pseudoinverse matrix. The weight matrix includes a plurality of elements representing system measurement sensitivity and distribution of diffused optical waves in a homogenous medium. The method further includes generating, using the computing device, each optimized functional image by iteratively optimizing successive estimates of the functional image regularized by the preliminary estimate of the functional image weighted by a regularization parameter. A value of the optimized functional image at each voxel in the lesion region is indicative of a hemoglobin concentration at that voxel. The method also includes displaying the at least one optimized functional image on a display device.

In yet another aspect, a non-transitory computer readable medium that includes computer-executable instructions for generating at least one optimized functional image of a lesion region of a breast is provided. When executed by at least one processor of a computing device, the computer-executable instructions cause the at least one processor to receive a plurality of measurements from a diffuse optical tomography (DOT) device. The plurality of measurements include lesion functional data from the lesion region of the breast and reference functional data from a healthy tissue region of a contralateral breast. The computer-executable instructions also cause the at least one processor to transform the lesion functional data and the reference functional data to produce perturbation data. The perturbation data represents a normalized difference between the lesion functional data and the reference functional data. The computer-executable instructions also cause the at least one processor to generate a preliminary estimate of the functional image by applying a pseudoinverse matrix of a weight matrix to the perturbation data. The pseudoinverse matrix may be a truncated pseudoinverse matrix. The weight matrix includes a plurality of elements representing system measurement sensitivity and distribution of diffused optical waves in a homogenous medium. The computer-executable instructions also cause the at least one processor to generate each optimized functional image by iteratively optimizing successive estimates of the functional image regularized by the preliminary estimate of the functional image weighted by a regularization parameter. A value of the optimized functional image at each voxel in the lesion region is indicative of a hemoglobin concentration at that voxel. The computer-executable instructions also cause the at least one processor to display the at least one optimized functional image on a display device.

BRIEF DESCRIPTION OF THE DRAWINGS

The drawings described below illustrate various aspects of the disclosure.

DETAILED DESCRIPTION

The systems and methods described herein relate to imaging systems and methods, and more specifically, imaging systems and methods used to generate optimized functional images of a lesion region in a subject. A subject as used herein is a human (live or deceased), an animal (live or deceased), an organ or part of an organ of a human or an animal, or part of a human or an animal. For example, a subject may be a breast, part of a human that includes an ovary, or part of a human that includes the colon or part of the colon. A lesion comprises abnormal tissue in a subject, such as a tumor, benign or malignant. A lesion region of a subject includes the region of the subject that comprises a lesion. Functional images are images or maps of an imaging volume that includes a lesion region. Functional images may be maps of the optical properties of the voxels of the imaging volume, such as absorption maps of the imaging volume, depicting the absorption coefficient at each voxel. Functional maps may be hemoglobin maps, depicting the hemoglobin concentration at each voxel. Functional maps may be total hemoglobin concentration (tHb) maps, oxyhemoglobin (oxyHb) maps, or deoxyhemoglobin (deoxyHb) maps, depicting the tHb, oxyHb, or deoxyHb concentration at each voxel, respectively.

The systems and methods disclosed herein can be used to detect the vasculature distribution at the lesion region of the subject, assess the malignancy of the tumor, and reduce biopsies of low-risk benign tumors without compromising cancer detection sensitivity. As a result, health care cost can be reduced while needed patient care is still delivered.

As to breast tumors, a vast majority of lesions recommended for biopsy are assessed as low to moderate suspicion (BI-RADS 4A, 4B), which may benefit from adjunctive DOT. Lesions diagnosed with a low suspicion of malignancy that also demonstrate low hemoglobin concentration may be recommended with follow-up instead of biopsy without compromising cancer detection. On the other hand, when a high suspicion (BI-RADS 4C or 5) lesion has a benign pathology result, the imaging pathology correlation is considered discordant, and a repeat biopsy or surgical excision is recommended in conventional treatment management. In such cases, an optical exam showing low vascularity can provide reassurance to allow for recommendation of less aggressive management, such as short term follow-up rather than additional tissue sampling or surgery.

The system and method disclosed herein can also be used to improve the accuracy of measured vasculature distribution and reduce the computation time to derive the measured vasculature distribution. In various embodiments, a regularized optimization method is used to reconstruct the functional data acquired by the DOT device. This method improves the stability of the computation, allows the optimization to converge fast (such as converging after 3 or less iterations) and, in the meantime, decrease the computation time.

Figure 1A:
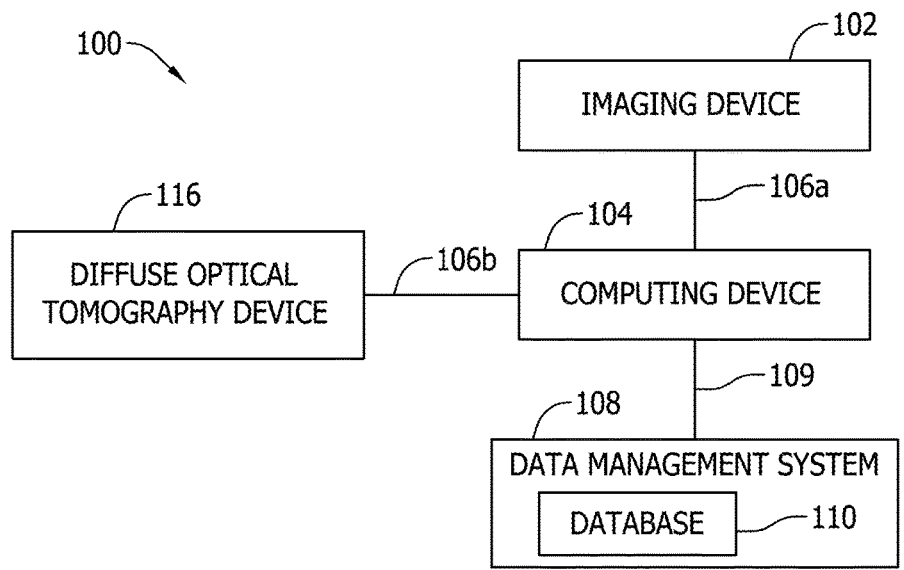
FIG. 1A is a schematic diagram showing an imaging system in accordance with an aspect of the disclosure.

As seen in FIG. 1A, system 100 includes a diffuse optical tomography (DOT) device 116, including, but not limited to, a near-infrared (NIR) diffuse optical tomography device and an NIR imager. In various embodiments, the DOT device 116 is a guided DOT device, defined herein as a DOT device operatively coupled to a second imaging device that obtains additional images of a subject in the form of guiding data used identify a region of interest corresponding to a lesion within a breast of the subject for subsequent partitioning and additional data processing of the imaging data acquired by the DOT device 116. The system 100 further comprises an imaging device 102 that is configured to acquire guiding data of a subject including the lesion region of the subject. The imaging device may be any suitable imaging device that makes use of an imaging modality different from the DOT device 116 including, but not limited to, an ultra-sound device, a magnetic resonance imaging system, an x-ray device, or a computed tomography device.

Figure 1B:
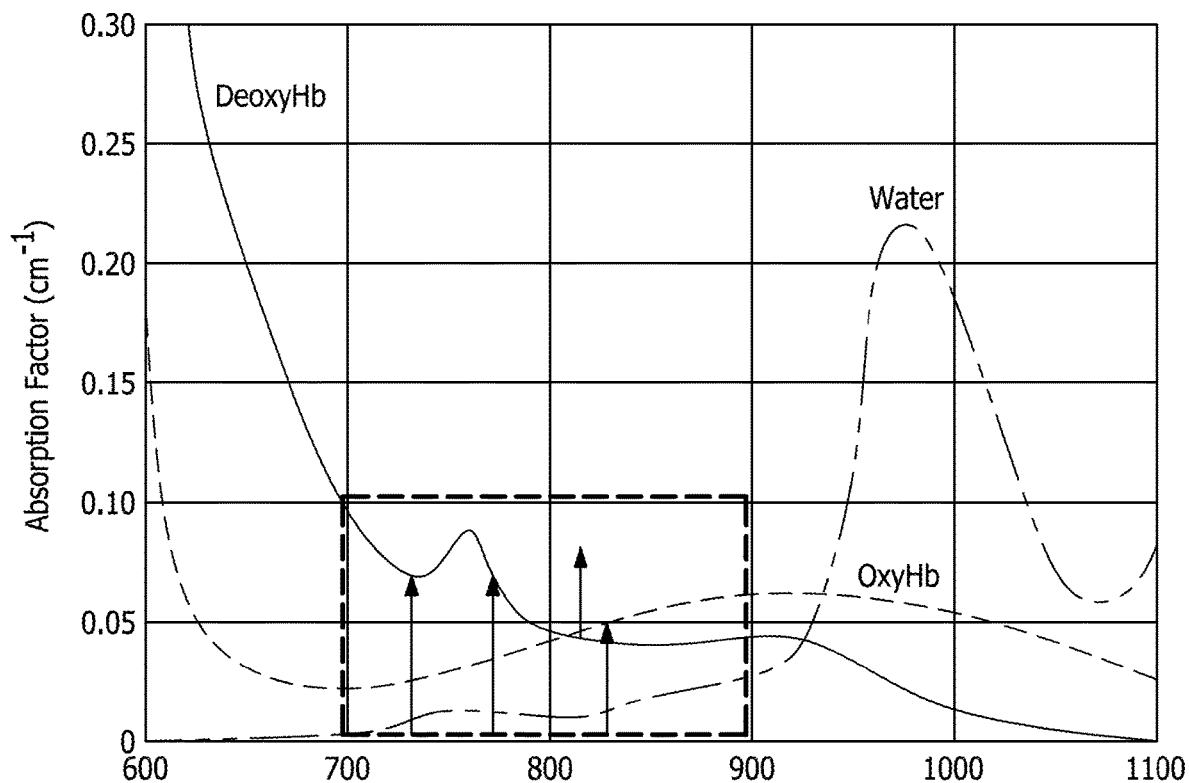
FIG. 1B is a plot showing absorption of optical waves at the near infrared spectrum by water, oxyhemoglobin (oxyHb), and deoxyhemoglobin (deoxyHb).

In various embodiments, the light spectrum used on the DOT device 116 is at the near-infrared spectrum (wavelength from ~700 to 900 nm). NIR DOT imaging is a noninvasive imaging technique that uses NIR light to estimate optical properties of tissue. FIG. 1B shows the absorption of the light as a function of the wavelength of the light for water (dashed-dashed line), oxyhemoglobin (oxyHb) (dashed line), and deoxyhemoglobin (deoxyHb) (solid line). The rectangular box includes the NIR spectrum range. As shown in FIG. 1B, in the NIR spectrum range, water absorbs light much less than oxyHb and deoxyHb, and oxyHb and deoxyHb each absorb the light at different rates depending on the wavelength of the emitted light. Four arrows superimposed on FIG. 1B point to absorption properties at wavelengths of 730 nm, 780 nm, 808 nm, and 830 nm, respectively. Because of the minimal absorption of water in the NIR spectrum (~700 to 900 nm), NIR light penetrates several centimeters in tissue. Within the NIR spectrum, oxygenated and deoxygenated hemoglobin are the major chromophores to absorb light and can be used to characterize tumor vasculature, which is directly related to tumor angiogenesis. DOT systems are usually portable, require no contrast agents, and have relatively low cost. These features make DOT systems well-suited for diagnosis of cancer and for assessment of neoadjuvant treatment response. However, intense light scattering in tissue typically causes the low spatial resolution and lesion location uncertainty in DOT images.

The DOT device 116 is configured to emit optical waves of a plurality of wavelengths toward an imaging volume of the subject. In various embodiments, the DOT device 116 is configured to emit optical waves at wavelengths 740, 780, 808 and 830 nm. The imaging volume includes a lesion region. The DOT device 116 is configured to acquire functional data representing the optical waves diffused by tissue in the imaging volume in response to the emitted optical waves.

The DOT device 116 and the imaging device 102 may be co-registered, where the imaging probes of the imaging device and the DOT device are directed to the same imaging volume. In various embodiments, the DOT device and the imaging device acquire data through one probe.

In the exemplary embodiment, system 100 also includes a computing device 104 coupled to imaging device 102 via a data conduit 106a and operatively coupled to the DOT device 116 via a data conduit 106b. It should be noted that, as used herein, the term "couple" is not limited to a direct mechanical, electrical, and/or communication connection between components, but may also include an indirect mechanical, electrical, and/or communication connection between multiple components. Imaging device 102 and the DOT device 116 may communicate with computing device 104 using a wired network connection (e.g., Ethernet or an optical fiber), a wireless communication means, such as radio frequency (RF), e.g., FM radio and/or digital audio broadcasting, an Institute of Electrical and Electronics Engineers (IEEE®) 802.11 standard (e.g., 802.11(g) or 802.11(n)), the Worldwide Interoperability for Microwave Access (WIMAX®) standard, a short-range wireless communication channel such as BLUETOOTH®, a cellular phone technology (e.g., the Global Standard for Mobile communication (GSM)), a satellite communication link, and/or any other suitable communication means. IEEE is a registered trademark of the Institute of Electrical and Electronics Engineers, Inc., of New York, New York. WIMAX is a registered trademark of WiMax Forum, of Beaverton, Oregon. BLUETOOTH is a registered trademark of Bluetooth SIG, Inc. of Kirkland, Washington.

In the exemplary embodiment, computing device 104 is configured to receive guiding data from the imaging device 102 and receive functional data from the DOT device 116. The computing device 104 may also be configured to control the imaging device 102 and the DOT device 116.

System 100 may further include a data management system 108 that is coupled to computing device 104 via a network 109. In some embodiment, the computing device 104 includes a data management system 108. Data management system 108 may be any device capable of accessing network 109 including, without limitation, a desktop computer, a laptop computer, or other web-based connectable equipment. More specifically, in the exemplary embodiment, data management system 108 includes a database 110 that includes previously acquired data of other subjects. In the exemplary embodiment, database 110 can be fully or partially implemented in a cloud computing environment such that data from the database is received from one or more computers (not shown) within system 100 or remote from system 100. In the exemplary embodiment, the previously acquired data of the other subjects may include, for example, a plurality of measurements of lesion region of other subjects. Database 110 can also include any additional information of each of the subjects that enables system 100 to function as described herein.

Data management system 108 may communicate with computing device 104 using a wired network connection (e.g., Ethernet or an optical fiber), a wireless communication means, such as, but not limited to radio frequency (RF), e.g., FM radio and/or digital audio broadcasting, an Institute of Electrical and Electronics Engineers (IEEE®) 802.11 standard (e.g., 802.11(g) or 802.11(n)), the Worldwide Interoperability for Microwave Access (WIMAX®) standard, a cellular phone technology (e.g., the Global Standard for Mobile communication (GSM)), a satellite communication link, and/or any other suitable communication means. More specifically, in the exemplary embodiment, data management system 108 transmits the data for the subjects to computing device 104. While the data is shown as being stored in database 110 within data management system 108, it should be noted that the data of the subjects may be stored in another system and/or device. For example, computing device 104 may store the data therein.

In the exemplary embodiment, when in use, the imaging device 102 acquires guiding data of the subject including a lesion region. The guiding data is transmitted to the computing device 104 via the data conduit 106a. The computing devices produces guiding images of the subject including the lesion region based on the guiding data. The DOT device 116 acquires functional data of the subject of an imaging volume that includes the lesion region. The functional data is transmitted to the computing device 104 via data conduit 106b. Although one computing device 104 is depicted in FIG. 1, two or more computing devices may be used in the system. The imaging device 102 and the DOT device 116 may be in communication with different computing devices (not shown) and the computing devices are in communication with each other.

In the exemplary embodiment, the computing device 104 is further programmed to identify the lesion region based on the guiding image reconstructed from the guiding data. The imaging volume selected for further analysis is chosen to include the lesion region. The imaging volume may be segmented into a plurality of regions including, but not limited to, the lesion region and a background region outside the lesion region. In various embodiments, the functional data at the lesion region comprises first voxels having fine voxel size and the functional data at the background region comprises second voxels having coarse voxel size that is greater than the fine voxel size. As a result, the overall number of voxels of the functional data selected for data processing and image reconstruction is reduced relative to the raw imaging data obtained by the DOT device 116, and consequently the computation complexity is reduced and computation speed is increased.

The computing device 104 generates optimized functional images of the subject including the lesion region by reconstructing the functional data using methods described in additional detail below. In various embodiments, the optimized functional images are reconstructed at the plurality of segmented regions including the lesion region and the background region.

In various embodiments, a two-step reconstruction method is used to produce DOT image estimates. In the first step, a preliminary estimate of the functional image is generated. In one aspect, the preliminary estimate is be generated by applying a pseudoinverse matrix of the weight matrix to the functional data. The pseudoinverse matrix may be a truncated pseudoinverse matrix. A weight matrix may represent the optical properties of the DOT device, as described in additional detail below. The weight matrix may also describe the distribution of diffused waves in a homogeneous medium, as well as characterizing the measurement sensitivity of the DOT device to the absorption and scattering change in the object being imaged. In one embodiment, a truncated Moore-Penrose Pseudoinverse (MPP) solution is used to compute a preliminary estimate of the functional images using the functional data or the measured data acquired by the DOT device, as described in additional detail below. In the truncated MPP solution, the pseudoinverse matrix of the weight matrix is truncated. In various embodiments, the size of the truncated pseudoinverse matrix is selected based on the number of singular values of the weight matrix greater than a threshold value. In various embodiments, this threshold value is chosen as 10% of the largest singular value of the weight matrix.

The MPP method is particularly well-suited for computing the initial estimate of the functional images, target images, or target for several reasons. First, the truncated pseudoinverse produced using MPP, by definition, produces a least-squares estimate of the image that possesses the minimum norm. Consequently, the estimate can be interpreted as an orthogonal projection of the true target image onto a subspace that is the orthogonal complement to the null space of the imaging operator. Therefore, the truncated pseudoinverse produced using MPP describes an estimate of the target that is closest to the true target but contains no component in the null space. This is a reliable strategy for image reconstruction when no reliable a priori information about the target is available. Second, the MPP truncated pseudoinverse solution can be easily regularized by excluding contributions that correspond to small values. Therefore, the regularization parameter used for subsequent optimized image reconstruction may be selected with little ambiguity. Third, the MPP truncated pseudoinverse operator can be explicitly stored in memory to speed up the computation, enabling nearly real-time image reconstruction. The systems and methods disclosed herein enhance the image's accuracy and reconstruction speed relative to the images produced using existing reconstruction methods.

In various embodiments, the second step of the two-step reconstruction method incorporates the preliminary estimate into the design of a penalized or regularized optimization method to generate optimized functional images, as described in additional detail below. In one embodiment, the optimization method may be a least squares estimator. In another embodiment, a Newton optimization method is used for the optimization method. In an additional embodiment, a conjugate gradient method is used for the optimization method. In various embodiments, the regularization parameter used in the optimization method is chosen as the largest singular value of the weight matrix multiplied by a factor proportional to the tumor size in the lesion region, as described below.

The functional data acquired by the DOT device reflects the optical properties of the object being imaged or the imaging volume imaged by the DOT device (see Eq. (1) in Example 2). In various embodiments, the optical properties of the imaging volume are derived by reconstructing the functional data according to the methods described herein. In various embodiments, to calibrate the optical properties obtained by reconstruction, e.g., curve fitting, of the functional data acquired by the DOT device, phantoms constructed with a medium having known optical properties may be used to derive the relation between the phantom and the average tissue background optical properties. The background optical properties include absorption coefficient $\mu_a$, reduced scattering coefficient $\mu_s'$, and diffusion coefficient D (D relates to $\mu_s'$ as $$D = \frac{1}{3\mu_s'}\bigg).$$

In various embodiments, the optimized functional images are indicative of the hemoglobin concentration of the tissue in the imaging volume. The value of each voxel of the optimized functional images in indicative of the hemoglobin concentration at that voxel. In various embodiments, the optimized functional images comprise absorption maps at each voxel of the optical waves. The absorption maps may be used to compute a hemoglobin concentration at each voxel.

In various embodiments, the absorption coefficient is a key parameter for evaluating tumor angiogenesis and relates to the hemoglobin concentration (oxyHb, deoxyHb, and tHb) within the tissue of the object being imaged. With this relationship between the absorption coefficient and the hemoglobin concentration, once the absorption coefficient is computed, the hemoglobin concentration, including the oxyHb concentration, the deoxyHb concentration, and the tHb, can be derived from the computed absorption coefficient.

In various embodiments, a threshold hemoglobin concentration is defined to assess various properties of the lesion tissue. In one embodiment, the malignancy level of the lesion is determined based on the measured tHb in comparison with the threshold hemoglobin concentration, and a recommendation for biopsy is generated based on the level of malignancy. In various embodiments, if the tHb is higher than the threshold hemoglobin concentration, the lesion is indicated as malignant. If the tHb is lower than the threshold hemoglobin concentration, the lesion is indicated as benign. In various embodiments, the tHb is evaluated in conjunction with the category of the breast tumor diagnosed by the radiologist. A more conservative or less conservative threshold hemoglobin concentration may be selected based on the tumor category. In various embodiments, for the purpose of biopsy recommendation, a conservative threshold hemoglobin concentration may be selected, or a more or less conservative threshold hemoglobin concentration is selected depending on the category diagnosed by the radiologist.

In the exemplary embodiment, the optimized functional images are displayed to a practitioner for further evaluation. The optimized functional images may be transmitted to a display device such as a monitor, a television, a mobile device, or a tablet, for display. The display device may be part of the computing device 104.

Figure 2:
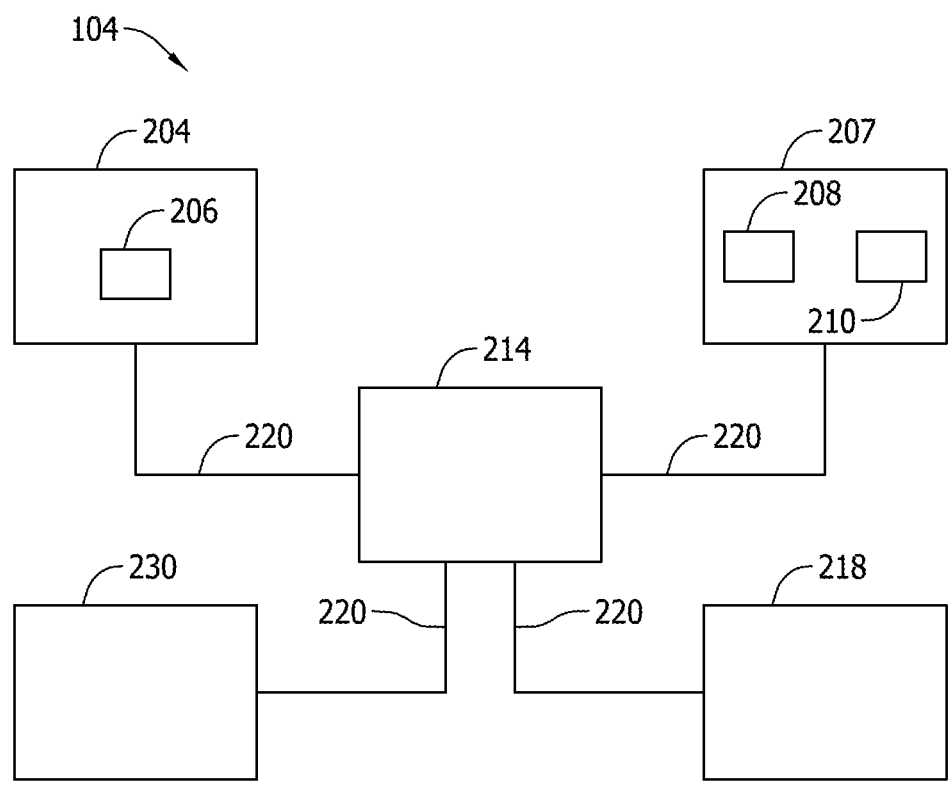
FIG. 2 is a block diagram illustrating a computing device in accordance with an aspect of the disclosure.

FIG. 2 is a block diagram of a computing device 104. In the exemplary embodiment, computing device 104 includes a user interface 204 that receives at least one input from a user, such as an operator of imaging device 102 or the DOT device 116 (shown in FIG. 1). User interface 204 may include a keyboard 206 that enables the user to input pertinent information. User interface 204 may also include, for example, a pointing device, a mouse, a stylus, a touch sensitive panel (e.g., a touch pad, a touch screen), a gyroscope, an accelerometer, a position detector, and/or an audio input interface (e.g., including a microphone).

Moreover, in the exemplary embodiment, computing device 104 includes a presentation interface 207 that presents information, such as input events and/or validation results, to the user. Presentation interface 207 may also include a display adapter 208 that is coupled to at least one display device 210. More specifically, in the exemplary embodiment, display device 210 may be a visual display device, such as a cathode ray tube (CRT), a liquid crystal display (LCD), an organic LED (OLED) display, and/or an "electronic ink" display. Alternatively, presentation interface 207 may include an audio output device (e.g., an audio adapter and/or a speaker) and/or a printer.

Computing device 104 also includes a processor 214 and a memory device 218. Processor 214 is coupled to user interface 204, presentation interface 207, and to memory device 218 via a system bus 220. In the exemplary embodiment, processor 214 communicates with the user, such as by prompting the user via presentation interface 207 and/or by receiving user inputs via user interface 204. The term "processor" refers generally to any programmable system including systems and microcontrollers, reduced instruction set circuits (RISC), application specific integrated circuits (ASIC), programmable logic circuits (PLC), and any other circuit or processor capable of executing the functions described herein. The above examples are exemplary only, and thus are not intended to limit in any way the definition and/or meaning of the term "processor."

In the exemplary embodiment, memory device 218 includes one or more devices that enable information, such as executable instructions and/or other data, to be stored and retrieved. Moreover, memory device 218 includes one or more computer readable media, such as, without limitation, dynamic random access memory (DRAM), static random access memory (SRAM), a solid state disk, and/or a hard disk. In the exemplary embodiment, memory device 218 stores, without limitation, application source code, application object code, configuration data, additional input events, application states, assertion statements, validation results, and/or any other type of data. Computing device 104, in the exemplary embodiment, may also include a communication interface 230 that is coupled to processor 214 via system bus 220. Moreover, communication interface 230 is communicatively coupled to imaging device 102, DOT device 116, and data management system 108 (shown in FIG. 1).

In the exemplary embodiment, processor 214 may be programmed by encoding an operation using one or more executable instructions and providing the executable instructions in memory device 218. In the exemplary embodiment, processor 214 is programmed to select a plurality of measurements that are received from imaging device 102 or the DOT device 116. The plurality of measurements may include, for example, a plurality of voxels of at least one image of the subject, wherein the image may be generated by processor 214 within computing device 104. The image may also be generated by an imaging device (not shown) that may be coupled to computing device 104, imaging device 102 and/or the DOT device, wherein the imaging device may generate the image based on the data received from imaging device 102 or the DOT device and then the imaging device may transmit the image to computing device 104 for storage within memory device 218. Alternatively, the plurality of measurements may include any other type measurement of the lesion region that enables system 100 to function as described herein.

Figure 3:
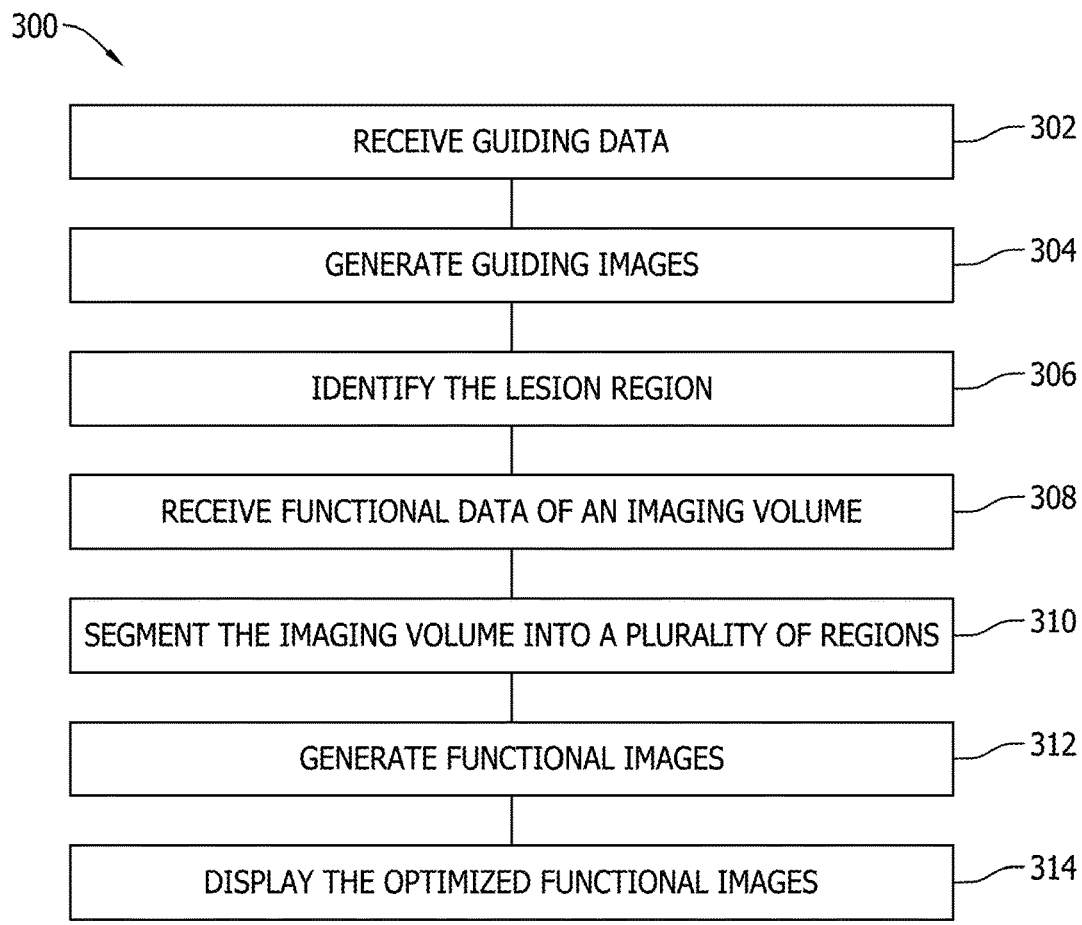
FIG. 3 is a flow chart showing an example method of generating optimized functional images.

FIG. 3 is a flow chart depicting an example method 300 of generating optimized functional images of a lesion region of a subject. The method 300 includes receiving guiding data of the subject at 302. The guiding data may be acquired by an imaging device as described above. The method 300 further includes generating guiding images of the subject by reconstructing the guiding data at 304. The reconstruction methods of the guiding images may be any method suitable for the imaging modality of the imaging device. The method 300 further includes identifying the lesion region within the guiding image of the subject at 306.

The method 300 further includes receiving functional data of an imaging volume at 308. The functional data may be acquired by a DOT device as described above. The imaging volume includes the lesion region and surrounding tissues. The method 300 further includes segmenting the imaging volume into a plurality of regions at 310. The plurality of regions includes the lesion region identified in the guiding images and a background region outside the lesion region. The functional data at the lesion region may comprise first voxels having a fine voxel size. The functional data at the background region may comprise second voxels having a coarse voxel size greater than the fine voxel size. After segmentation, the number of voxels of the functional data may be reduced. The method 300 further includes generating functional images of the subject at 312. The method 300 further includes displaying the optimized functional images at 314.

Figure 4A:
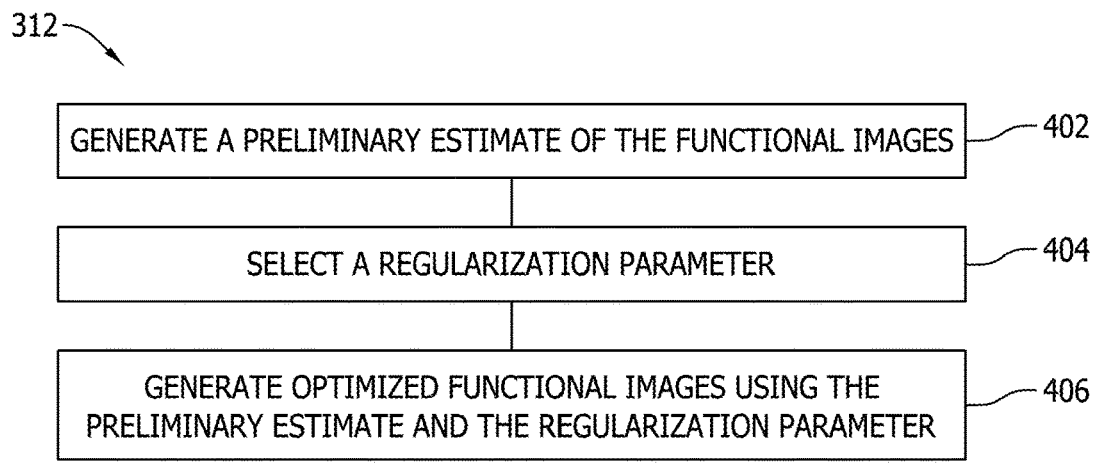
FIG. 4A is a flow chart showing an example method of generating functional images.

Referring to FIG. 4A, generating functional images of the subject at 312 may comprise generating preliminary estimates of the functional images at 402. As described herein, the preliminary estimates may be generated by applying a pseudoinverse matrix of the weight matrix to the functional data. In various embodiments, the pseudoinverse matrix comprises a truncated Moore-Penrose pseudoinverse matrix. In various embodiments, the pseudoinverse matrix is truncated to a matrix size comprising the number of singular values of the weight matrix larger than a threshold value. In various embodiments, the threshold value comprises 10% of the largest singular value of the weight matrix. Generating functional images at 312 may further comprise selecting a regularization parameter at 404. Generating functional images 312 may further comprise generating optimized functional images using the preliminary estimate and the regularization parameter at 406. In various embodiments, the optimized functional images are generated by regularized or penalized optimization method, where the optimization is regularized by the preliminary estimate weighted by the regularization parameter. The optimization method may be any suitable optimization method including, but not limited to, a conjugated gradient method and Newton method. The Newton method and the conjugate gradient are faster to converge and take less computation time than other available optimization methods.

In various embodiments, the systems and methods further include computation of perturbation imaging dataset $U_{sc}$ based on the functional data acquired by the DOT device, where the perturbation imaging dataset is used to reconstruct the functional images. As described in additional detail below, the perturbation imaging dataset $U_{sc}$ represents a change in optical properties of the lesion tissue relative to background optical properties representative of healthy tissue. The systems and methods may further include removal of outliers in acquired functional data.

Figure 4B:
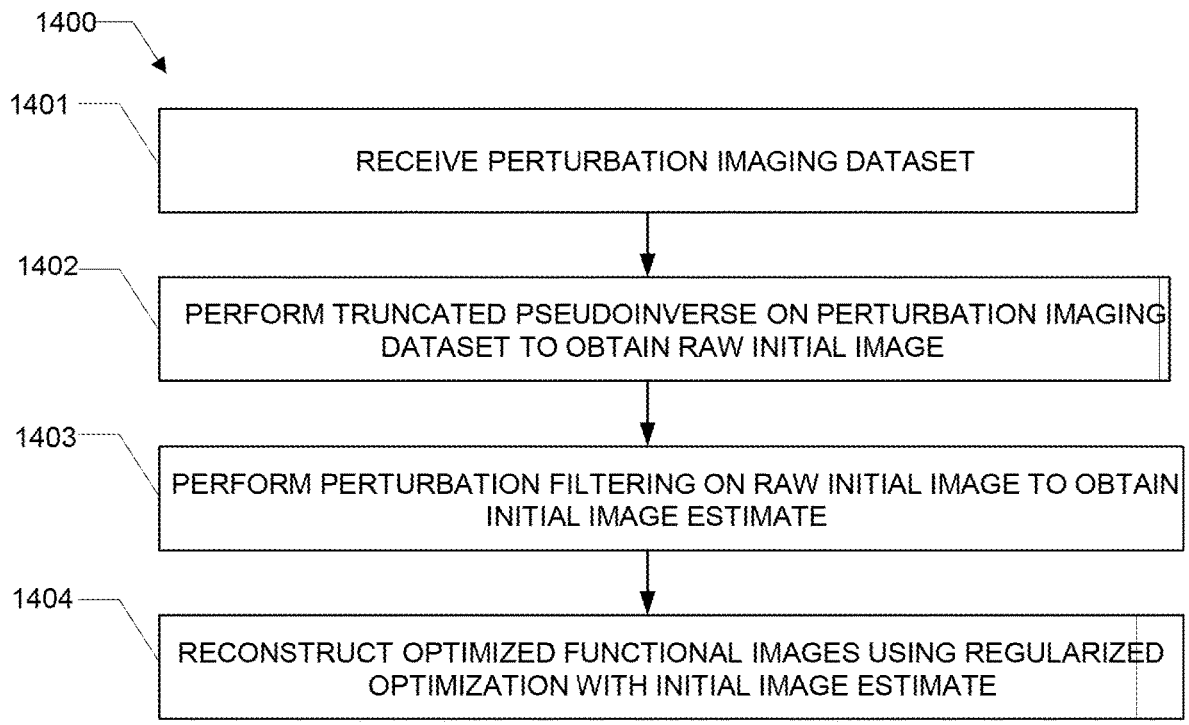
FIG. 4B is a flow chart showing an example method of reconstructing functional images.

FIG. 4B shows an example method 1400 of reconstructing functional images using the perturbation imaging dataset $U_{sc}$ computed as described herein. The method 1400 includes receiving a computed perturbation imaging dataset at 1401. The perturbation imaging dataset $U_{sc}$ may be computed in a perturbation computation module of the computing device or may be precomputed on and transmitted from a separate computing device. The method 1400 further comprises performing a truncated pseudoinverse on the perturbation imaging dataset to obtain a raw initial image at 1402. The method 1400 further comprises performing perturbation filtering on the initial image at 1403 to obtain an initial image estimate to be used as the preliminary estimate of the functional images. The method 1400 further comprises reconstructing the optimized functional image at 1404 using the regularized optimization method regularized by the initial image estimate. The regularization parameters used in the regularized optimization may be derived from the target size and the singular values of the weight matrix.

Figure 4C:
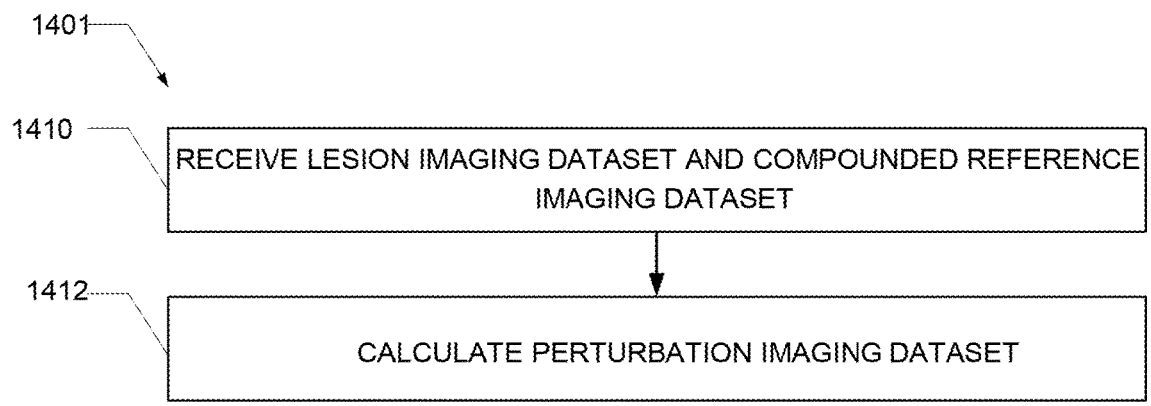
FIG. 4C is a flow chart showing an example method of computing a perturbation imaging dataset.

FIG. 4C is a block diagram illustrating additional steps of method 1400 associated with receiving the perturbation imaging dataset at 1401 as illustrated in FIG. 4B. As illustrated in FIG. 4C, receiving the perturbation imaging dataset at 1401 further comprises receiving functional data obtained using the DOT device at 1410. In various aspects, the functional data includes a lesion imaging dataset obtained from a breast containing a lesion, and a compound reference imaging dataset derived from absorption measurements of corresponding healthy tissue including, but not limited to, a contralateral breast of the patient, as described in additional detail below. The method further comprises calculating the perturbation imaging dataset at 1412.

Figure 4D:
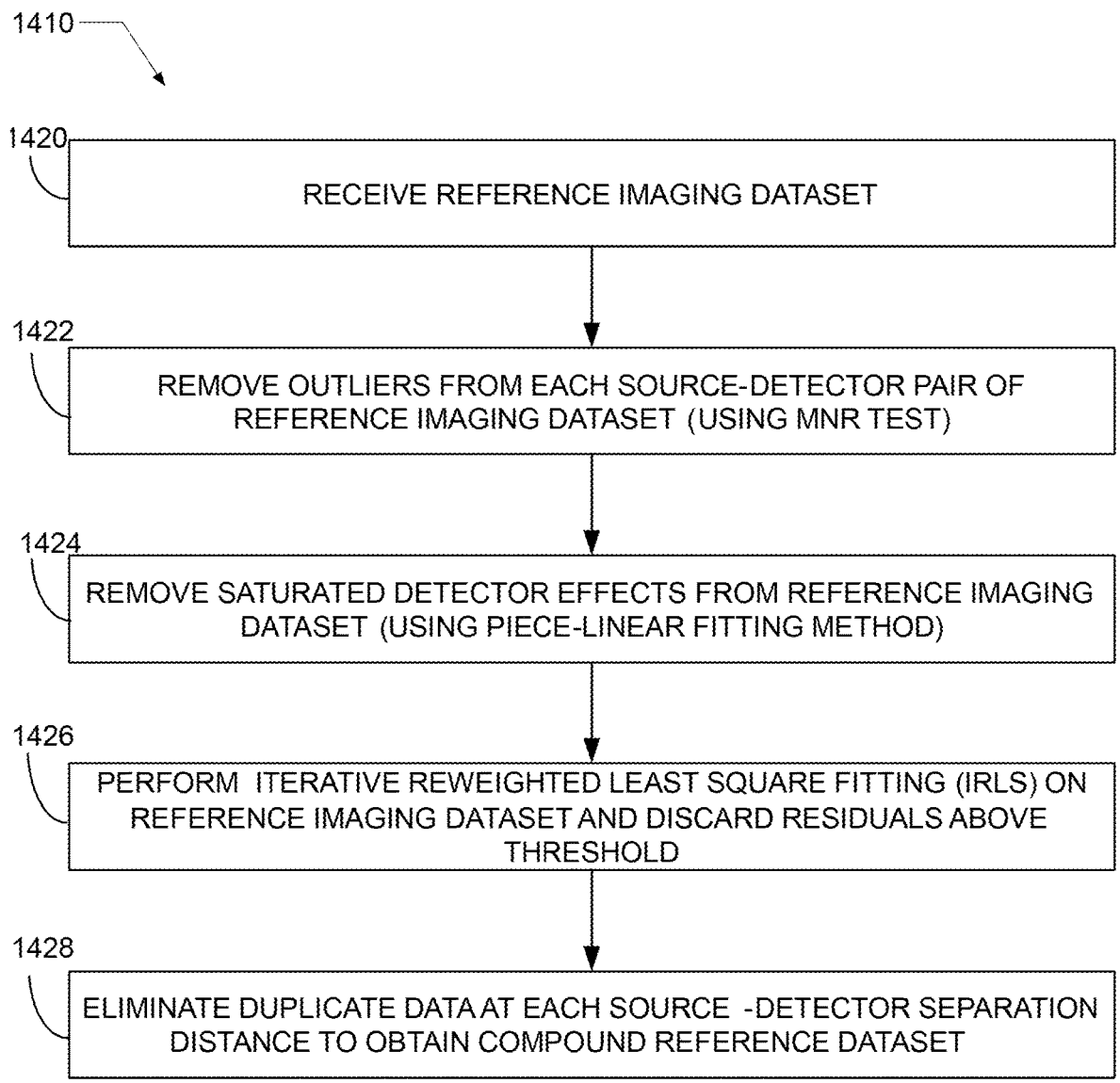
FIG. 4D is a flow chart showing an example method of constructing a compound reference dataset.

FIG. 4D is a flow chart illustrating additional steps of the method 1400 associated with receiving the lesion imaging dataset and compounded reference imaging dataset at 1410 as illustrated in FIG. 4C. Referring to FIG. 4D, receiving the functional data at 1410 further includes constructing a compound reference dataset based on absorption measurements of healthy tissue including, but not limited to, a healthy breast of the patient, as obtained by a DOT device. Constructing the compounded reference imaging dataset includes receiving a reference imaging dataset at 1420 that includes absorption measurements obtained from healthy tissue corresponding to the lesion tissue, as obtained by the DOT device from a contralateral breast of a patient in one embodiment. Receiving the functional data at 1410 further comprises removing outliers from each source-detector pair of the reference imaging dataset at 1422. In one embodiment, a maximum normed residual (MNR) test may be used to remove outliers at 1422. Receiving the functional data at 1410 may further comprise removing saturated detector effects from the reference imaging dataset at 1424. In one embodiment, a piece-linear fitting method is used to remove saturated detector effects at 1424. Receiving the functional data at 1410 may further comprise performing iterative reweighted least square fitting (IRLS) on reference imaging dataset and discarding residuals above a threshold at 1426. Receiving the functional data at 1410 further comprises eliminating duplicated data at each source-detector separation distance to obtain the compound reference dataset at 1428.

Fast data acquisition, automated and robust data processing, and image reconstruction in near real-real time make the systems and methods described herein suitable for use in clinical settings. In various embodiments, a plurality of imaging datasets are acquired using the DOT device from a breast of a patient containing a lesion and from a contralateral breast of a patient containing normal, healthy breast tissue. Each dataset from source positions and all detectors takes only a few seconds to acquire, and several data sets are acquired at the lesion for computing average hemoglobin levels after reconstruction.

In various embodiments, the probe of the DOT device is moved to the contralateral normal breast at the same quadrant as the lesion to acquire reference data used to estimate the average tissue optical properties ($\mu_a$ and $\mu_s'$). In various embodiments, several reference datasets are acquired for off-line selection of the best reference, using linear fitting criteria of the amplitude and phase profiles vs. source-detection distance. The average $\mu_a$ and $\mu_s'$ are used to compute the weight matrix W for image reconstruction. Tissue optical properties determined from the contralateral breast may be the best estimate of the background tissue for reconstruction of images of the lesion region. The entire data acquisition, including several datasets at the lesion region and contralateral sites, takes a few minutes. In some aspects, to reduce the duration of the data acquisition phase, the data processing and image reconstruction are done off-line. These data processing and image reconstruction tasks may make use of manual operation by experienced users and can take up to 30-40 minutes, depending on the amount of patient imaging data.

Reducing user interaction via automated processing can help the systems and methods move toward adoption for clinical use. In a hand-held operation, bad coupling between the light guides and the breast can result in measurement outliers. Additionally, tissue heterogeneity can cause measurement errors in some source-detector pairs. Recovered background and lesion optical properties depend on the boundary measurements of light propagating through the tissue underneath, and errors in these measurements can cause inaccuracy in the fitted background and reconstructed lesion optical properties.

In various embodiments, an automated outlier removal, data selection, and perturbation filtering method is used to improve the robustness and speed of estimating background optical properties and DOT reconstruction. This method utilizes multiple sets of reference measurements acquired at the contralateral normal breast to produce a robust set of reference measurements. Multiple sets of reference measurements are used to form a single high quality reference dataset. Background optical properties and then the weight matrix W are computed from the selected reference dataset.

A flowchart illustrating the steps of a method 1410 for automated outlier removal, data selection, and perturbation filtering is illustrated in FIG. 4D. The method 1410 includes an outlier removal procedure at 1422, e.g., MNR, to eliminate inaccurate measurements, with a criterion based on the statistical distribution of data collected at each source-detector pair. The method 1410 further includes piece-linear fitting at 1424 to reject the source-detector pair measurements obtained from saturated photomultiplier tubes (PMTs). Without being limited to any particular theory, PMT can saturate at a short source and detector distance, which varies for each individual PMT. Third, an iterative fitting of the residue of the remaining data further eliminates inaccurate measurements based on the linearity of the fitted results of the reference measurements of all source-detector pairs. The method 1410 further includes using a least-squares error method at 1426 to form the best reference dataset at 1426 used to form the compound reference at 1428, from the remaining measurements. In various aspects, the lesion measurement set obtained from the breast tissue containing the lesion is subtracted from the compound reference dataset and scaled by the compound reference dataset to form the normalized perturbation of the scattered field, $U_{sc}$.

Without being limited to any particular theory, outliers in the lesion data may be due to any one or more of a plurality of factors including, but not limited to, measurement errors and tissue heterogeneity. Lesion measurements are expected to be more heterogeneous than the reference measurements because the heterogeneity is partially caused by the lesion and partially by the background tissue. However, to separate the bad measurements caused by movement and/or bad coupling from those caused by lesion heterogeneity, caution may be needed in using an outlier removal procedure, such as MNR. In various embodiments, the threshold in the MNR statistical test may be adjusted to remove large outliers that are likely caused by motion or bad coupling.

In various embodiments, simulations were performed using different background optical properties for both reference and lesion breasts, as well as different optical properties for lesions of different sizes located at different depths. The results show that the maximum phase difference of any of the source detector pairs may be set to be 90 degrees, even in extreme cases. Further, the mean and the standard deviation of the imaginary part of the perturbation was calculated. If the imaginary part of a data point is farther than three standard deviations from the mean, the data point is classified as an outlier and removed from the perturbation dataset. Any data points in the perturbation dataset that do not meet these two criteria are rejected. This step removes outliers in the perturbation likely caused by measurement errors rather than heterogeneity of the lesion.

In various embodiments, after the steps of outlier removal and filtering, the normalized perturbation is used to reconstruct the absorption map at each wavelength. The total hemoglobin map is calculated from the four wavelength absorption data. The entire imaging reconstruction takes about 1 to 2 minutes, depending on lesion size. Therefore, the total time needed for imaging each patient can be reduced to less than 5 minutes, which is sufficient for radiologists to read the images and provide feedback on a revised BI-RADs score including the DOT data.

Although, in some of the examples provided below, the systems and methods disclosed herein are used on breasts and breast tumors, the systems and methods are not limited to this part of human or animal body or this type of tumor or cancer.

EXAMPLES

The following example illustrates various aspects of the disclosure.

Example 1: Imaging Malignant and Benign Breast Lesions

Two large scale clinical studies were performed with the system described herein. The findings are listed in Table 1 and summarized below. The two studies, performed at two sites, included more than 450 women. Study 1 included 162 patients and study 2 included 288 patients with readers or radiologists. All subjects had been referred for an ultrasound (US) guided biopsy of a suspicious sonographic lesion. The ultrasound images and optical measurements were obtained with a commercial ultrasound transducer positioned in the hybrid handheld imaging probe of the DOT device. A minimum of three co-registered ultrasound/optical imaging datasets of the lesion were acquired at each imaging location of the lesion, as well as of the contralateral breast, which was used as a reference. Optical absorption distributions at each wavelength were reconstructed, and the tHb was computed from the absorption maps. Maximum and average lesion tHb concentrations were measured. Sensitivity, specificity, and positive and negative predictive values (PPV and NPV) were calculated using a tHb threshold level (82 µmol/L for Study 1 and 80 µmol/L for Study 2) established to separate malignant from benign lesions. The thresholds were based on review of the data and determination of the value at which sensitivity would provide clinically relevant differentiation of benign and malignant tissue. Lesions that exceeded the tHb threshold level were considered malignant. The tHb threshold levels differ between the two studies because different numbers of optical wavelengths were used. Biopsies, which served as ground truth for disease status in both studies, were performed on all subjects and reviewed by pathologists. Approximately 35% of the lesions in Study 1 and 20% of the lesions in Study 2 were malignant.

TABLE 1

Summary of Two Clinical Studies

| Objective | Population | Outcome |
| --- | --- | --- |
| STUDY 2 Investigate US-guided optical imaging in distinguishing functional differences in tHb, oxyHb, and deoxyHb in malignant and benign breast lesions. Evaluate US-guided optical imaging in conjunction with US in improving diagnosis of malignant and benign breast lesions. | N = 288 subjects 60 malignant 235 benign | Mean max tHb, oxyHb, and deoxyHb were significantly higher in malignant groups than in the benign group. Sensitivity and NPV increased when tHb was used in combination with US reader data. Sensitivity for malignant lesions increased from 78.0% to 96.6% for Reader 1 and from 81.4% to 100% for Reader 2. |
| STUDY 1 Investigate the role of US-guided optical Imaging in differentiating early-stage cancers from benign lesions | N = 162 subjects 61 malignant 114 benign (lesions) | Mean max tHb was significantly higher in malignant groups than in the benign group. For early Stage cancers (Tis-T1), Sensitivity, specificity, PPV, and NPV based on tHb were 92%, 92%, 80%, and 97%, respectively. The corresponding values for T2-T4 tumors were 75%, 92%, 67% and 95%, respectively. |

Figure 5A:
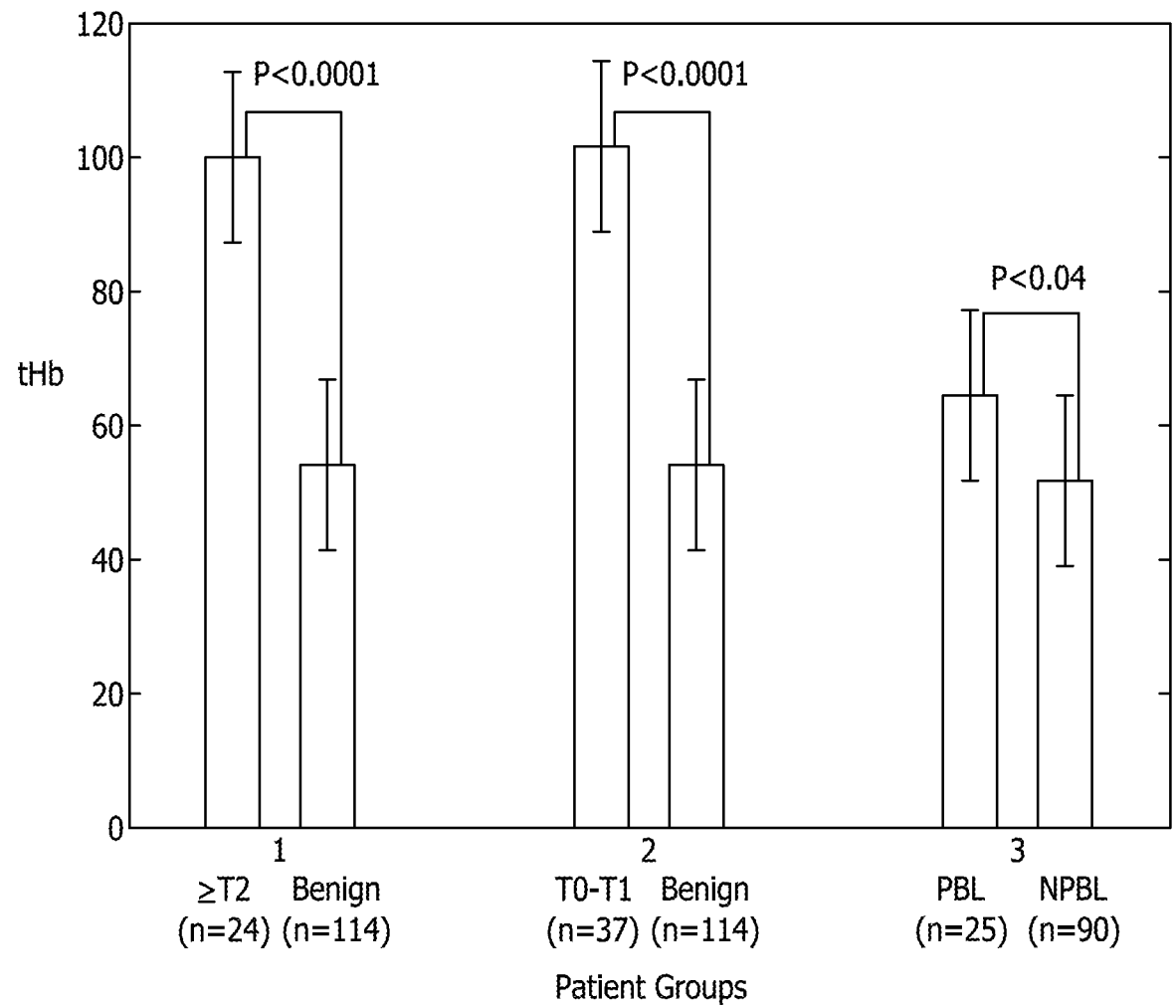
FIG. 5A is a bar graph comparing the measured total hemoglobin concentration among various patient groups.
Figure 5B:
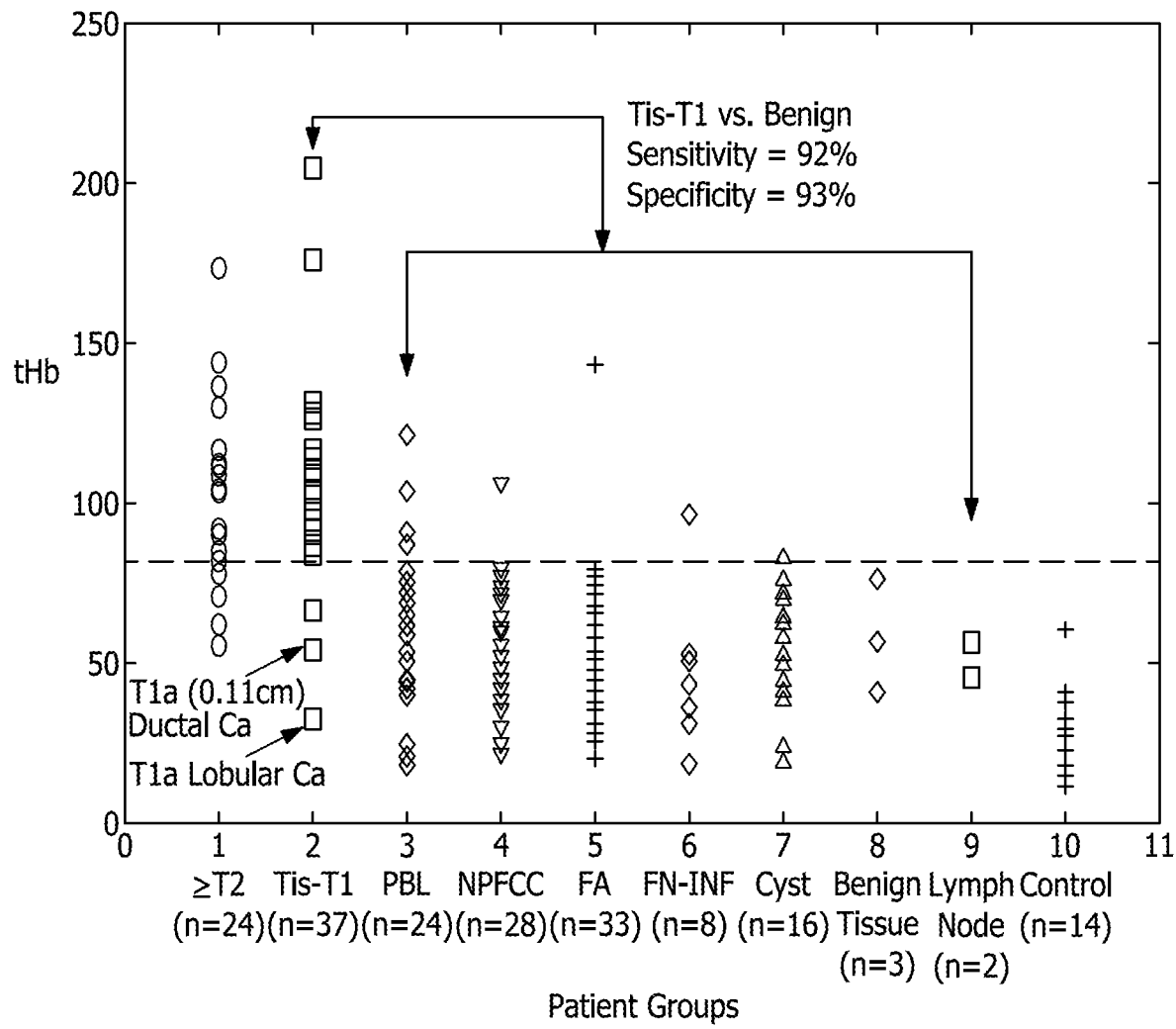
FIG. 5B is a scatter plot comparing the measured total hemoglobin concentration of various tissue.

FIG. 5A is a graph summarizing the measured total hemoglobin concentration among various patient groups in Study 1. In Study 1, maximum tHb levels were used to characterize malignant vs. benign lesions. It was found that tHb was two-fold higher in the malignant groups (Stage 2 to 4 tumors (T2-4), and Stage 1 tumors (Tis-T1)) than in the benign group (P<0.0001) (see FIG. 5A). Additionally, the proliferative lesion (PBL) group showed a higher tHb content than the other benign lesion group (P<0.04). FIG. 5B is a scatter plot of the maximum tHb of T2-T4 tumors, Tis-T1 tumors, proliferative benign lesions, non-proliferative fibrocystic changes (NPFCC), fibroadenoma (FA), fat necrosis and inflammation/reactive changes (FN-INF), complex cysts, breast tissue, lymph nodes, and the control group. When 82 µmon was chosen as the tHb threshold level to separate malignant and benign lesions, the sensitivity, specificity, PPV, and NPV for Tis-T1 tumors were 92%, 92%, 80%, and 97%, respectively. For T2-T4 tumors, the sensitivity, specificity, PPV, and NPV were 75%, 92%, 67%, and 95%, respectively.

Figure 6A:
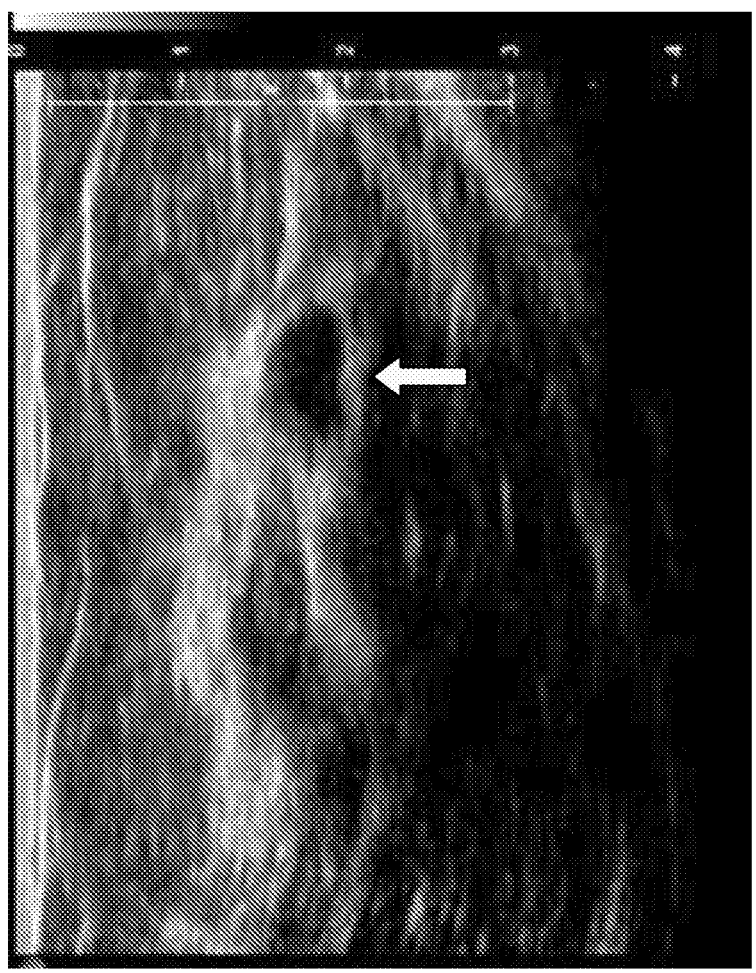
FIG. 6A is an ultrasound image of a breast of a patient.
Figure 6B:
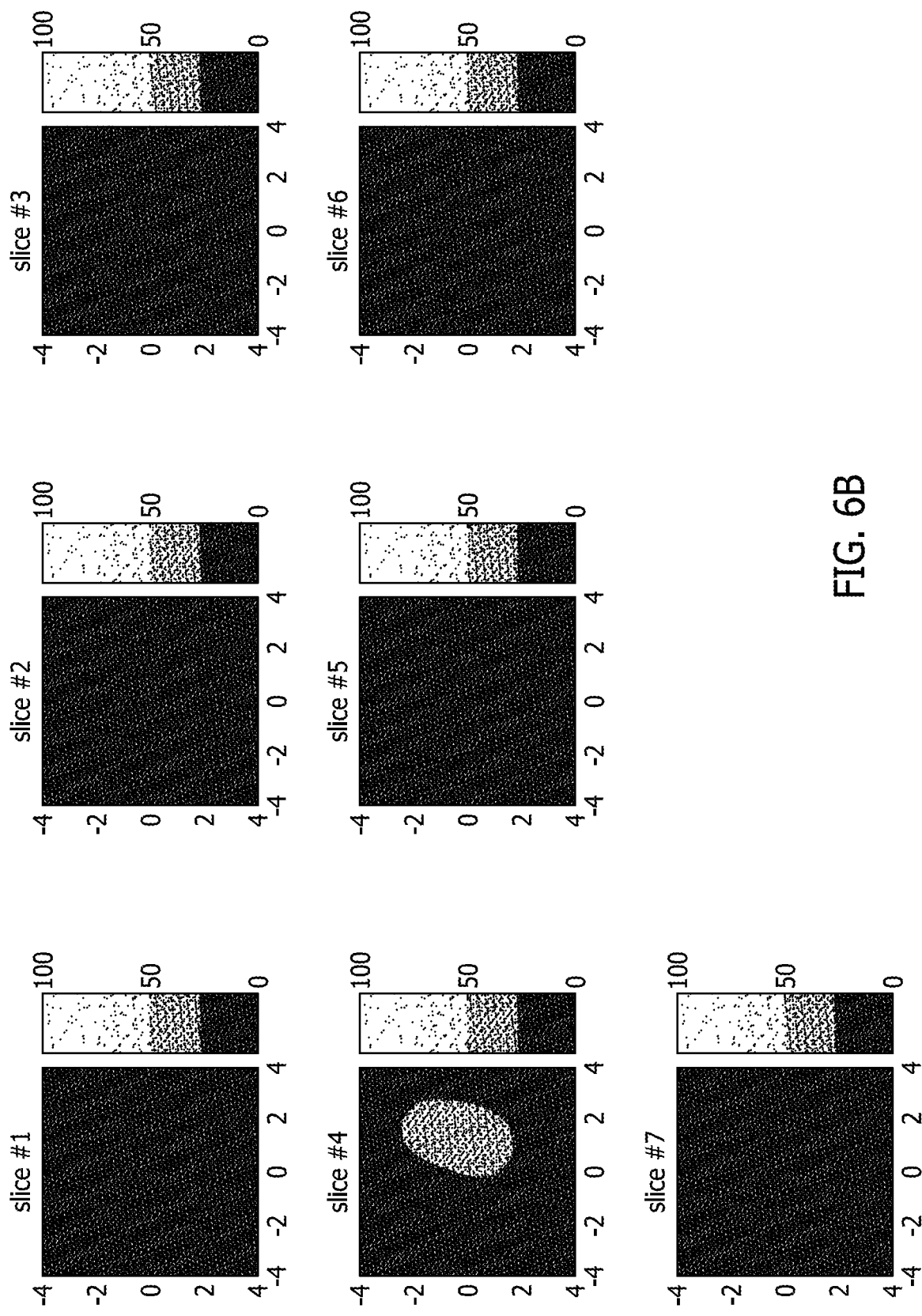
FIG. 6B contains a series of total hemoglobin concentration (tHb) maps for various slices of the breast image of FIG. 6A.
Figure 7A:
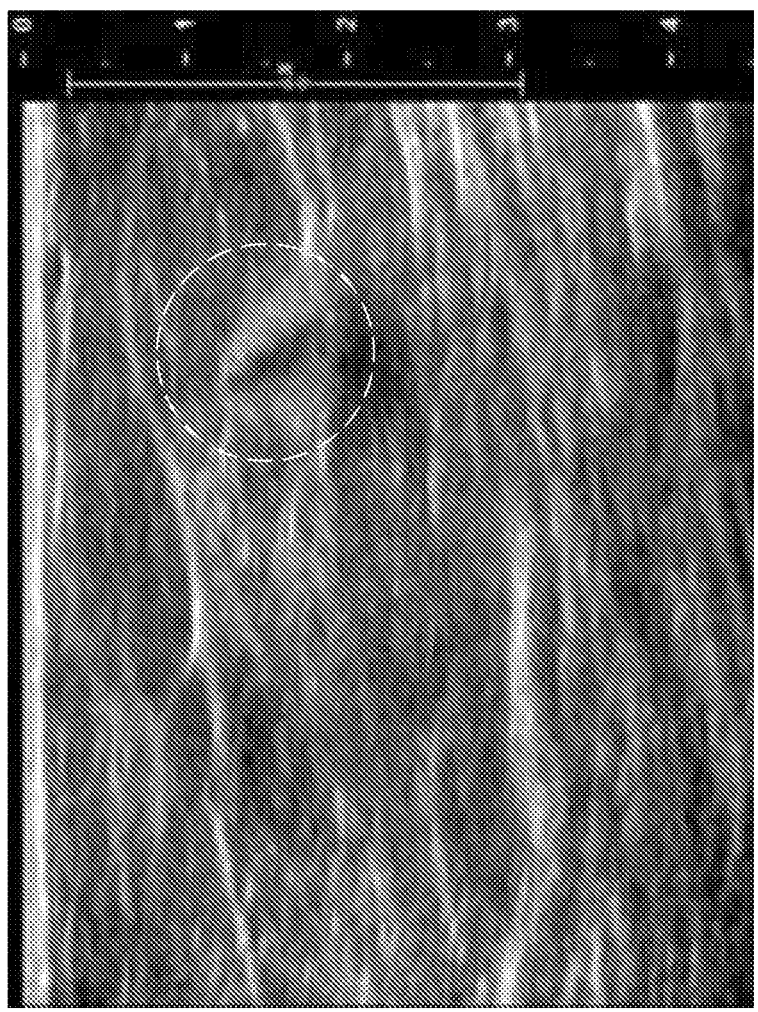
FIG. 7A is an ultrasound image of a breast of another patient.
Figure 7B:
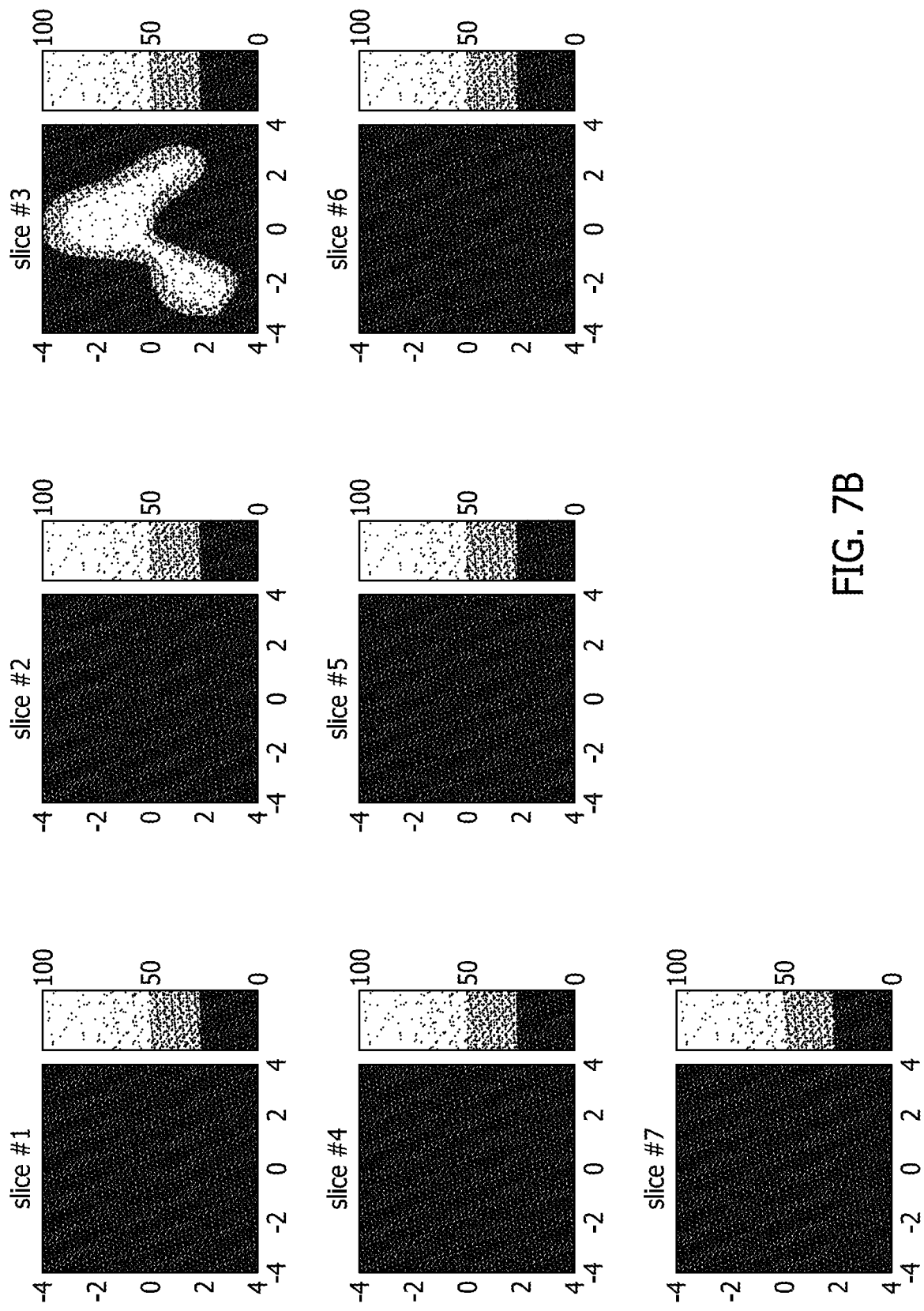
FIG. 7B contains a series of tHb maps for various slices of the breast image of FIG. 7A.

Illustrative examples of benign and malignant Stage 1 cancer cases assessed in the present example are provided below. FIG. 6A is a US image of a suspicious lesion (marked by a superimposed arrow) located in the left breast of a 37-year-old woman. The lesion was measured as 7 mm by US. FIG. 6B shows the tHb map having a low and diffused distribution with a maximum 35.3 μmon, at the corresponding depth location of slice #4. Core biopsy revealed a fibroadenoma. In the functional images, the first slice was 0.3 cm from the skin surface, and the last slice was 3.3 cm toward the chest wall. Each slice is a 9 cm-by-9 cm image at the x-y plane, with a 0.5 cm depth difference between slices. The vertical scale is the tHb concentration in μmon. FIG. 7A is a US image of a suspicious tubular-like lesion at the 12 o'clock position in the right breast of a 71-year-old woman. The lesion was measured as 7 mm by US. FIG. 7B is the tHb map, which showed an isolated, well-defined mass with a maximum ft-lb concentration of 97.8 μmon at the corresponding depth location of slice #3. The first slice was 0.7 cm below the skin surface, and the spacing between the slices was 0.5 cm. Biopsy revealed an invasive ductal carcinoma, and the pathologic tumor stage was T1c (1.2 cm).

Figure 8A:
FIG. 8A is an ultrasound image of a breast of an additional patient.
Figure 8B:
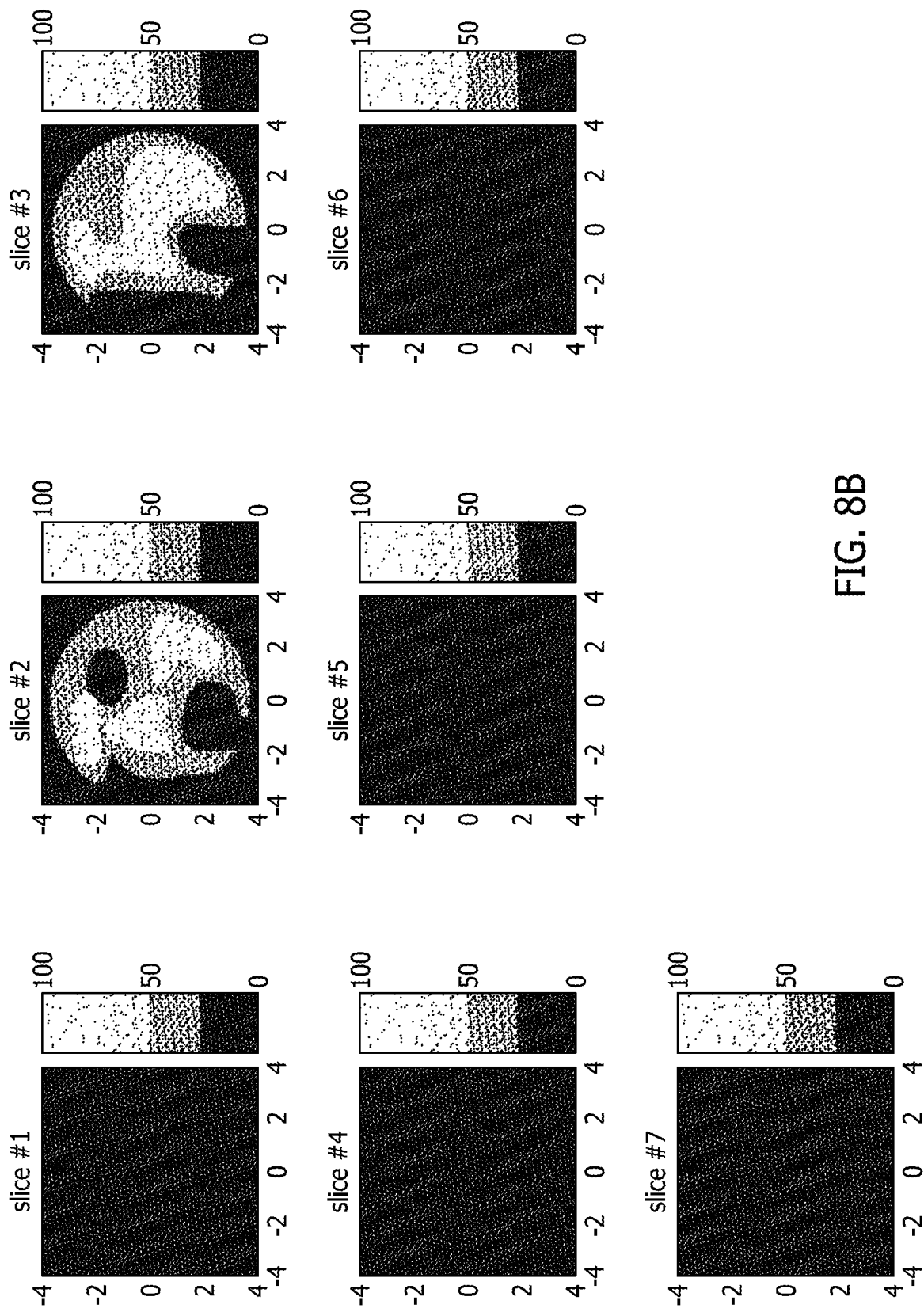
FIG. 8B contains a series of tHb maps for various slices of the breast image of FIG. 8A.

The results of these experiments demonstrated that the hemoglobin maps acquired by the systems and methods disclosed herein can be used with mammography/US for distinguishing early-stage invasive breast cancers from benign lesions. As for qualitative features seen in total hemoglobin maps of large cancers, 38% of the T2-T4 tumors showed heterogeneous periphery enhancement (FIGS. 8A-8D), which is unique and not observed in benign solid lesions. FIG. 8A is a US image of a suspicious lesion at the 11 o'clock position of the right breast of a 63-year-old woman. The lesion was measured as 3 cm in size by US. FIG. 8B shows the tHb map, which showed a heterogeneous distribution with a higher concentration at the periphery. The first slice was 0.2 cm below the skin surface. Biopsy revealed an invasive ductal carcinoma, and the pathologic tumor stage was T2 (2.2 cm).

Additionally, 33% of the T2-T4 tumors showed posterior shadowing. This shadowing is partially due to the significant light absorption by the tumor, which causes a dramatic reduction of the reflected light from the deep portion of the tumor. This light shadow effect is similar to the posterior shadow of larger tumors seen in US images. Thus, for large US-visible lesions, the systems and methods disclosed herein can provide angiogenesis distribution features and provide additional diagnostic value.

In the second, larger scale study (Study 2), the DOT device using four optical wavelengths allowed robust estimation of tHb, oxyHb, and deoxyHb concentrations. The maxima were significantly higher in the malignant groups than in the benign group (P<0.001, P<0.001, P<=0.035). For these malignant lesions, the maximum tHb moderately correlated with tumor histological grade (P=0.036) and nuclear grade (P=0.016). Thus, the tHb level can be used to identify aggressive cancers. The maximum oxyHb moderately correlated with tumor nuclear grade (P=0.042).

When a threshold of 80 μmol/L was used for tHb, the system disclosed herein achieved sensitivity, specificity, PPV, and NPV of 84.6%, 90.0%, 57.9% and 97.3%, respectively for the Tis-T1 group; the corresponding values were 72.9%, 90.0%, 64.2%, and 93.1%, respectively for the combined malignant group. Based on the US BI-RADS scores provided by the two radiologists, the corresponding values of sensitivity, specificity, PPV, and NPV for the combined malignant group were 78.0-81.4%, 83.0-90.1%, 55.8-66.7%, and 94.2-94.7%, respectively. When the radiologists' US diagnoses and tHb were used together where the radiologists' reading of 4C or 5, or tHb higher than the threshold of 80 μmol/L was considered as malignant, the corresponding values were 96.6-100%, 77.3-83.3%, 52.7-59.4% and 99.0-100%, respectively for the combined malignant group.

Figure 9A:
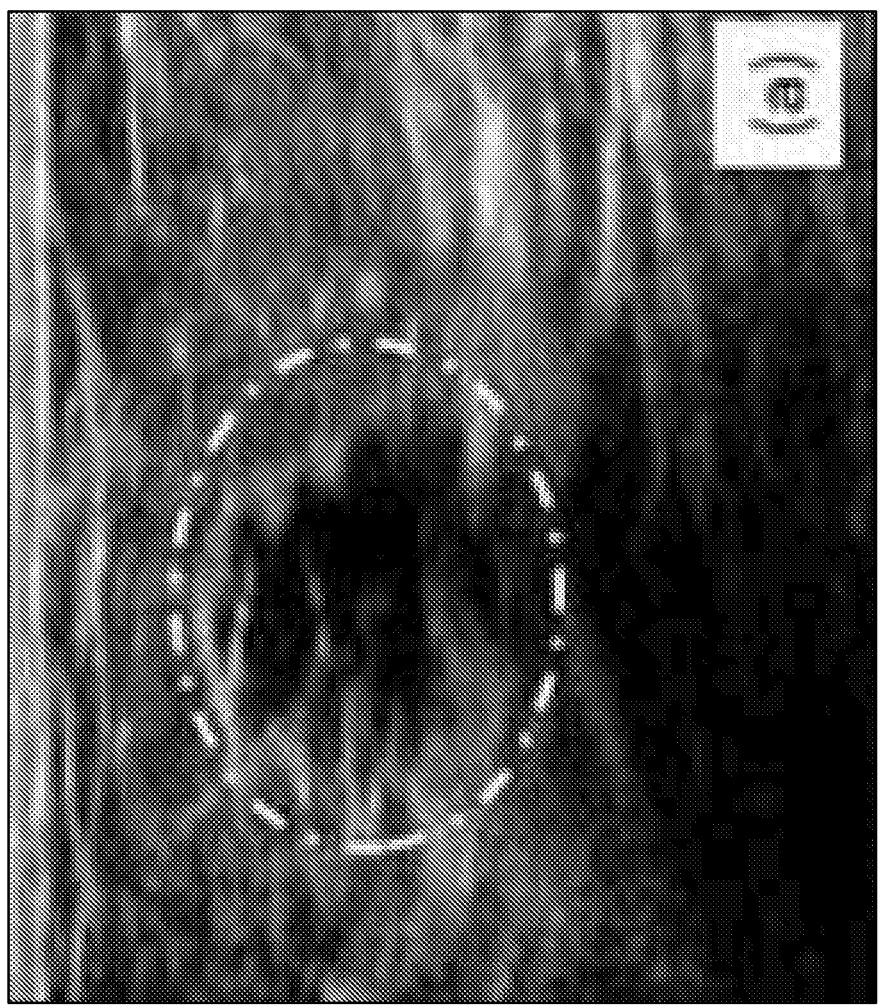
FIG. 9A is an ultrasound image of a breast of another additional patient.
Figure 9B:
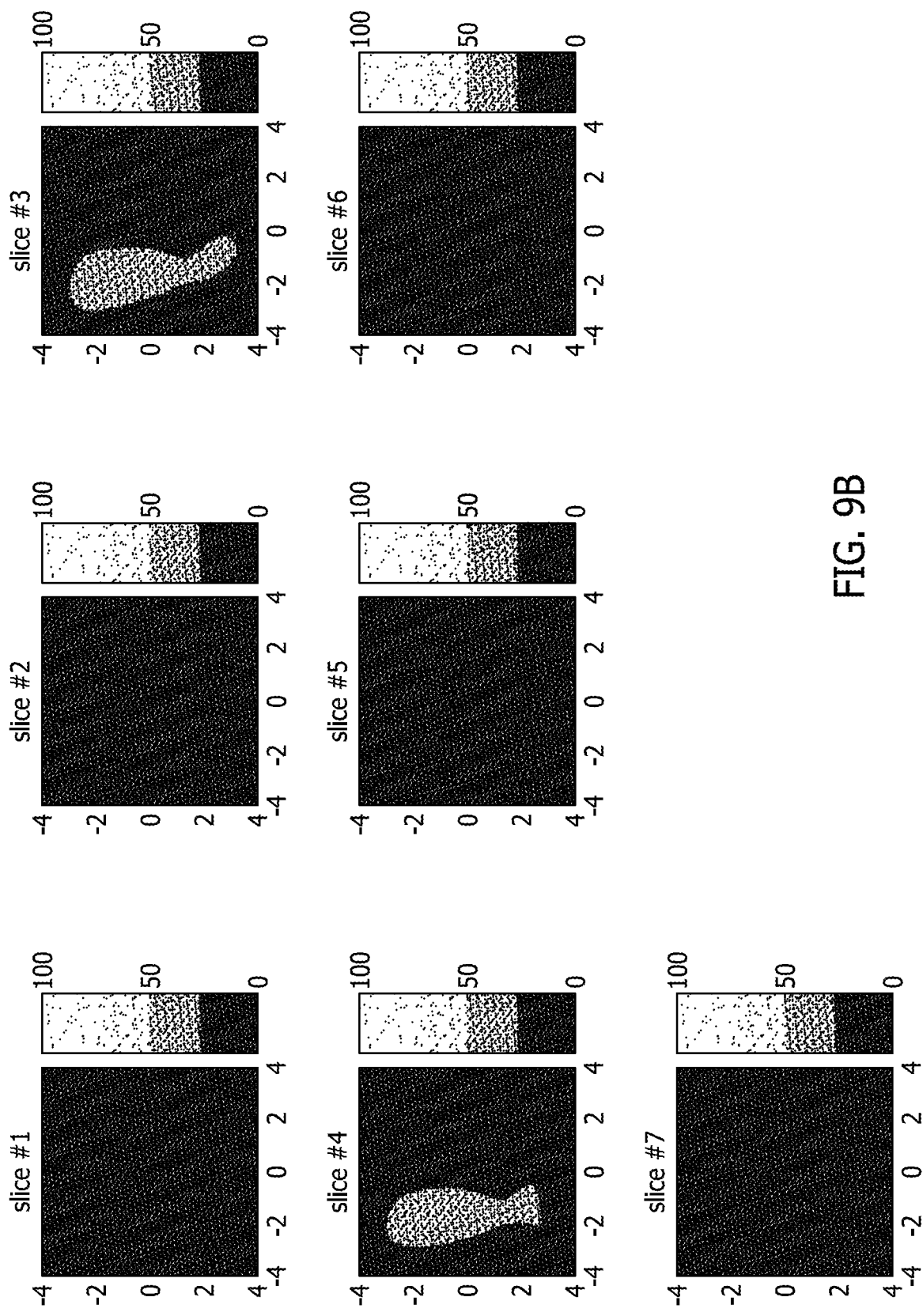
FIG. 9B contains a series of tHb maps for various slices of the breast image of FIG. 9A.
Figure 9C:
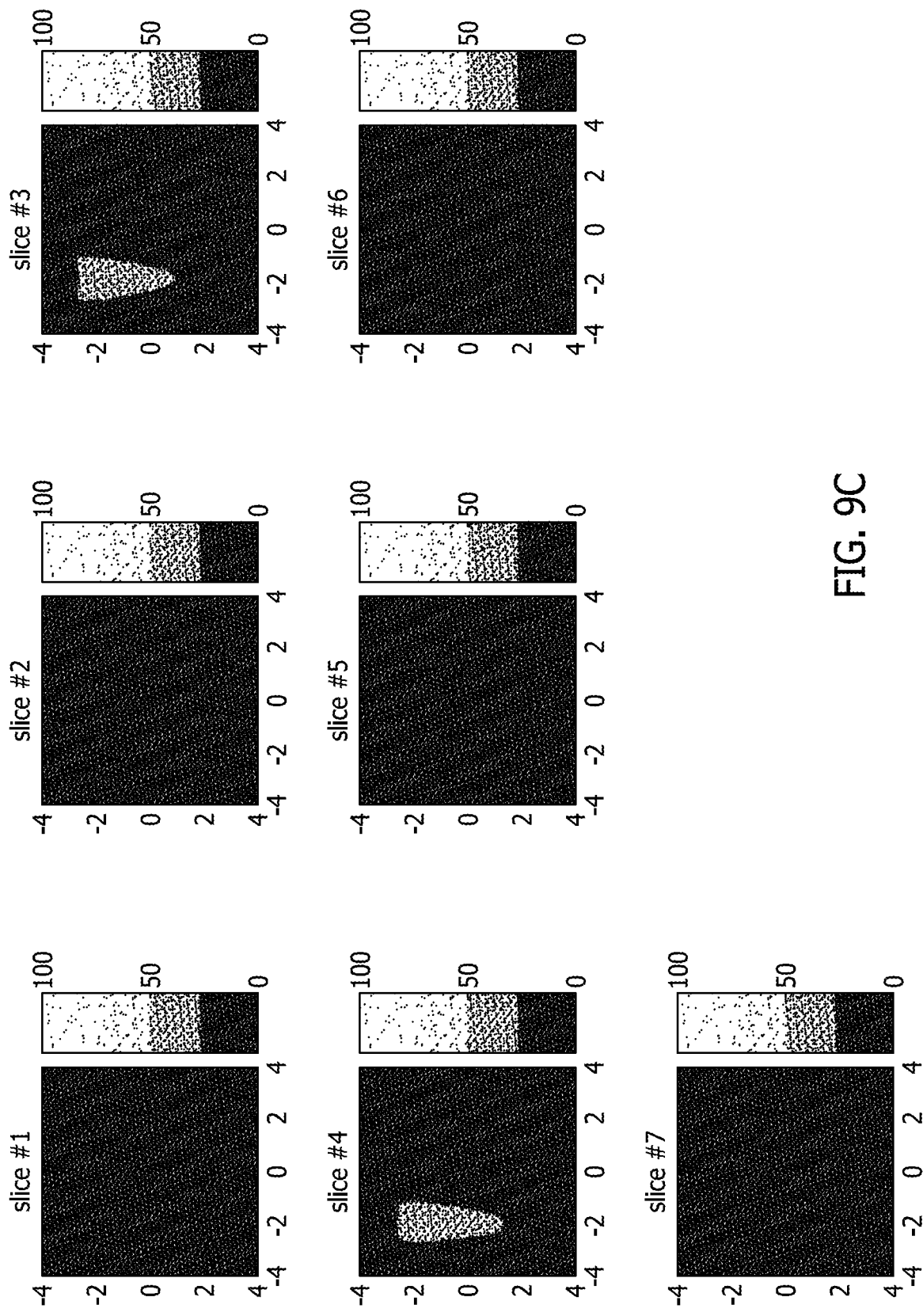
FIG. 9C contains a series of oxyHb maps for various slices of the breast image of FIG. 9A.
Figure 9D:
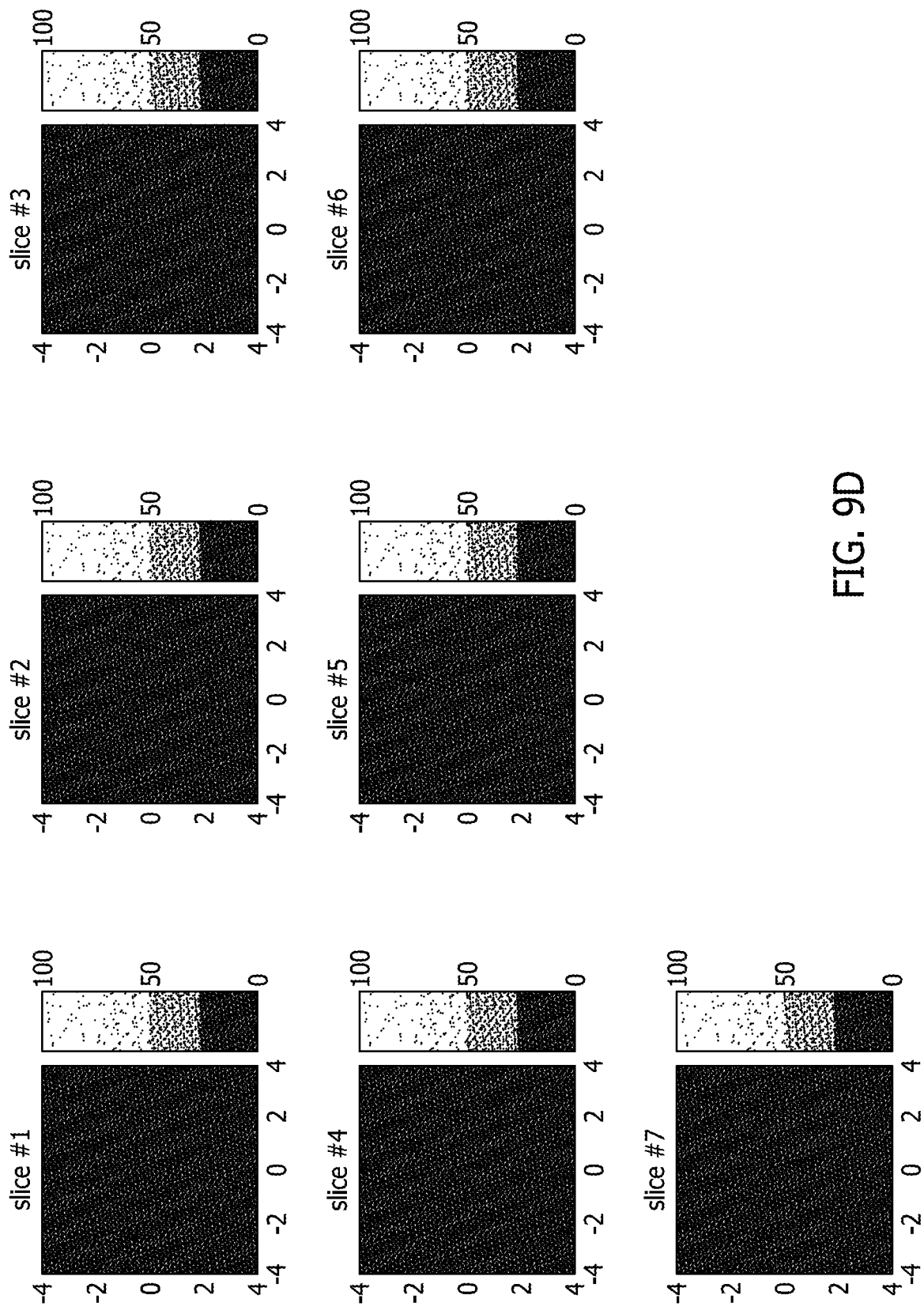
FIG. 9D contains a series of deoxyHb maps for various slices of the breast image of FIG. 9A.

As summarized in Table 2 (below), both sensitivity and NPV increased dramatically when the tHb data was used in combination with the diagnostic ultrasound data. The sensitivity for all malignant lesions, for example, increased from 78.0% to 96.6% for Reader 1, and from 81.4% to 100% for Reader 2. FIG. 9A is a US image of a hypoechoic lobulated mass with internal echoes and separations at 2 o'clock in the right breast of a 40-year-old woman. US readings from the two readers were 4B and 4C. FIG. 9B is a tHb map, showing a diffused mass with a maximum value of 52.5 μmol/L. FIG. 9C shows the oxyHb maps, and FIG. 9D shows the deoxyHb maps. Analysis of core biopsy samples revealed hylinized benign fibroadenoma.

Figure 10A:
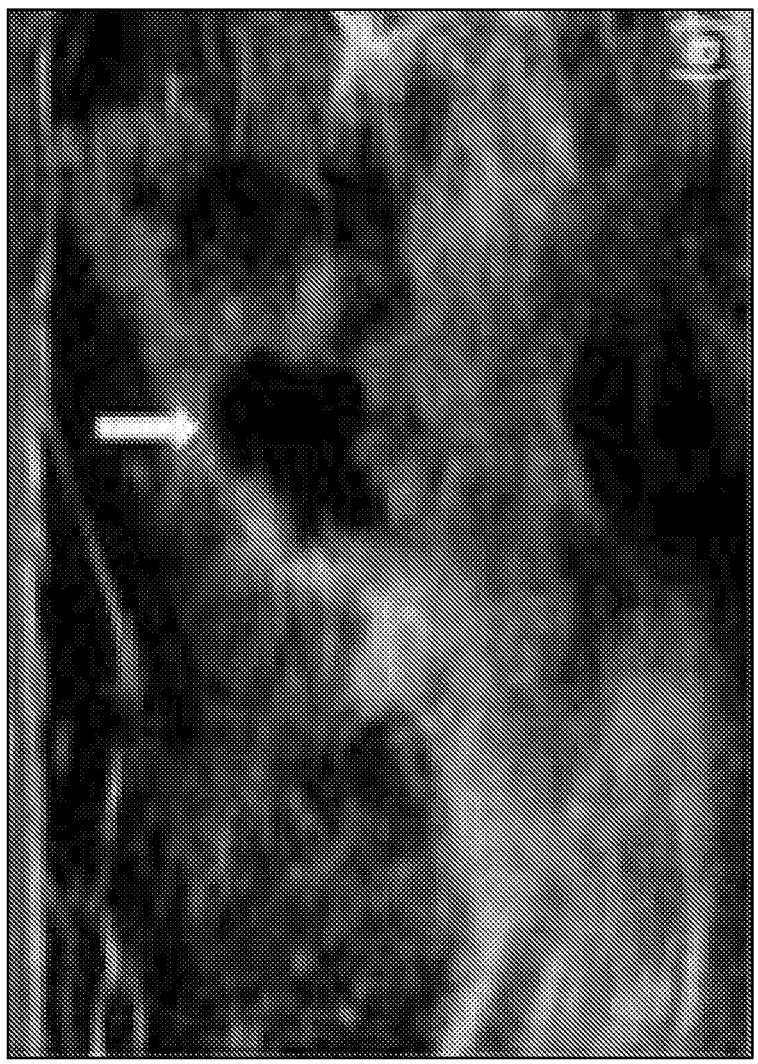
FIG. 10A is an ultrasound image of a breast of yet another patient.
Figure 10B:
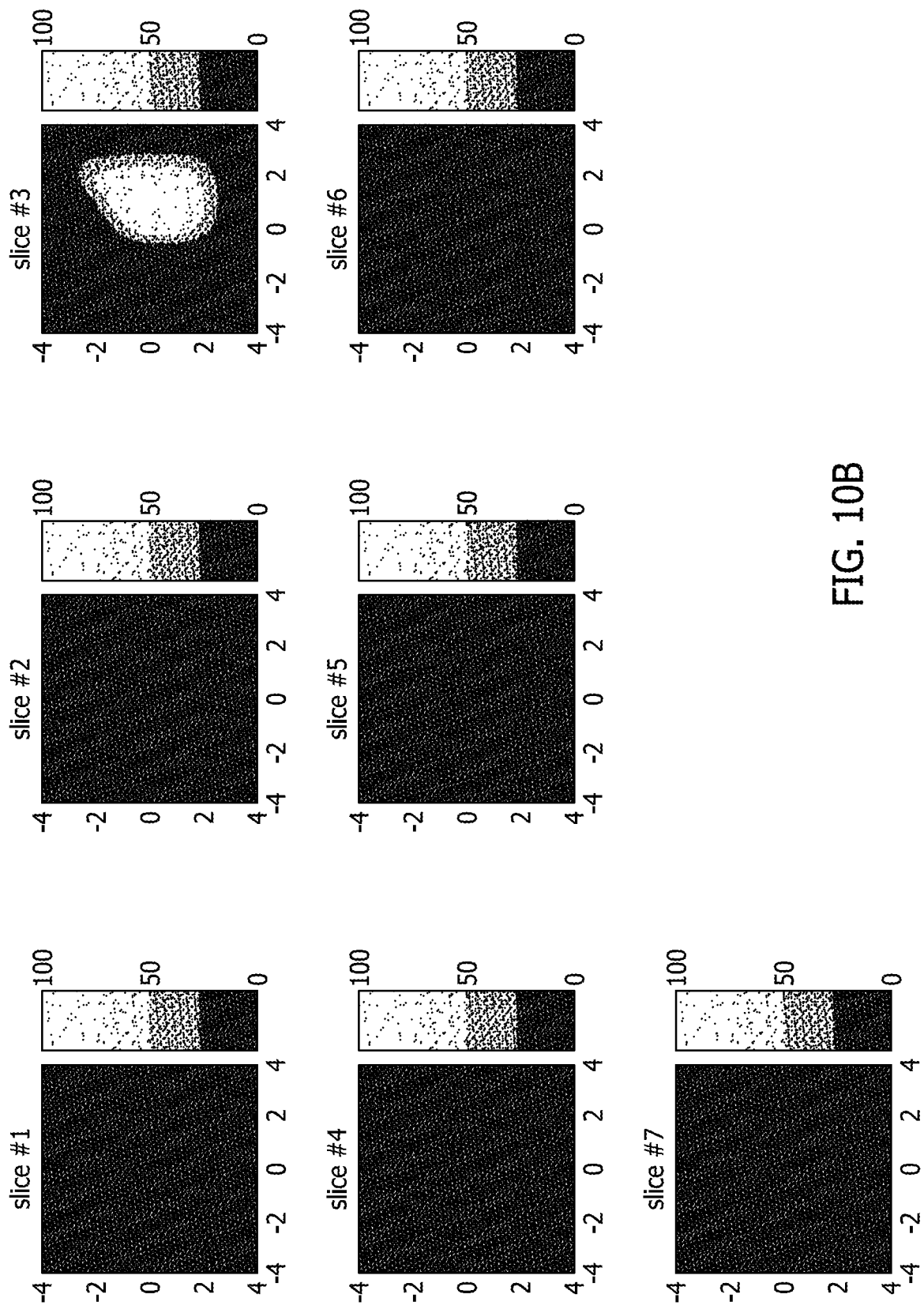
FIG. 10B contains a series of tHb maps for various slices of the breast image of FIG. 10A.
Figure 10C:
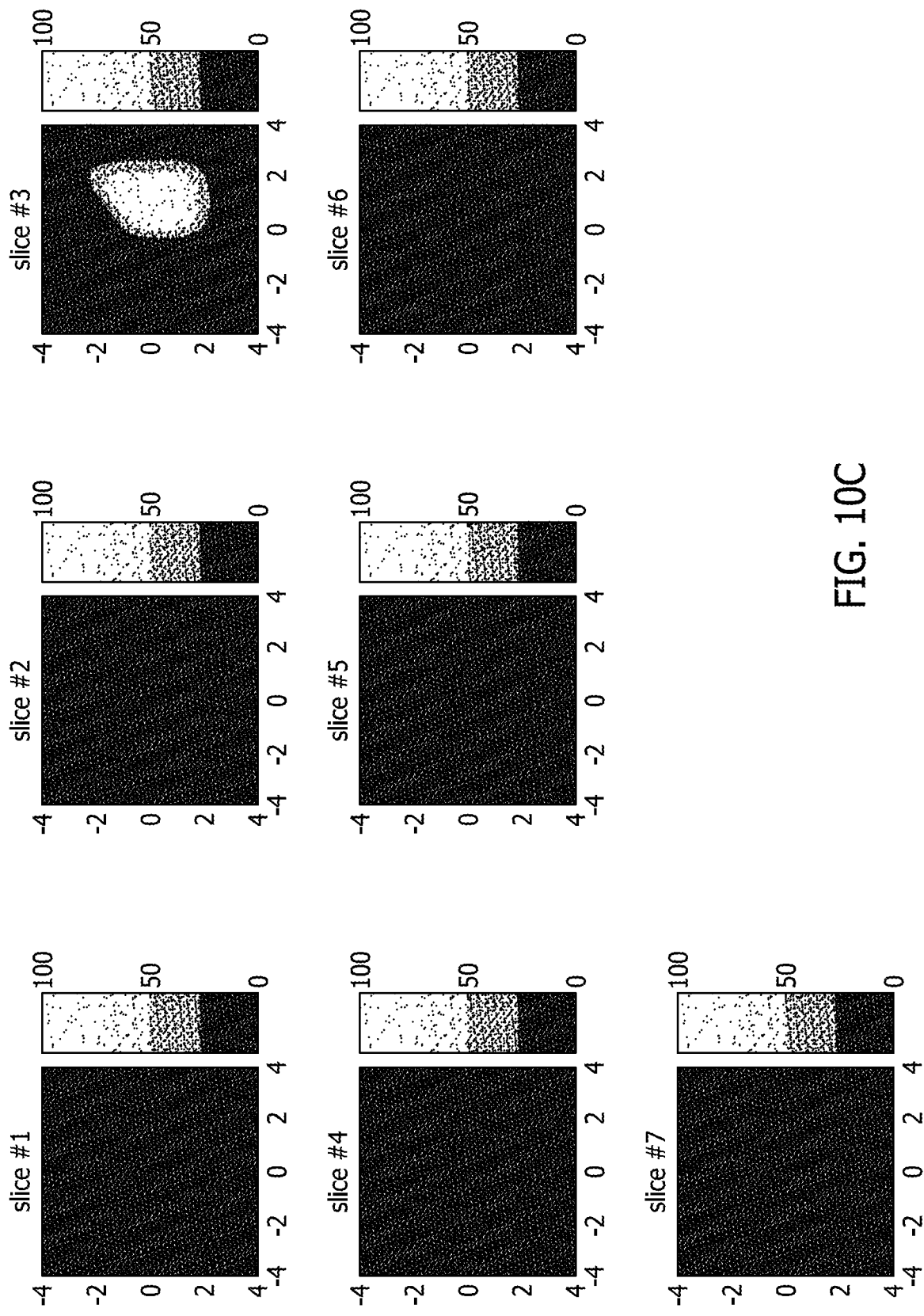
FIG. 10C contains a series of oxyHb maps for various slices of the breast image of FIG. 10A.
Figure 10D:
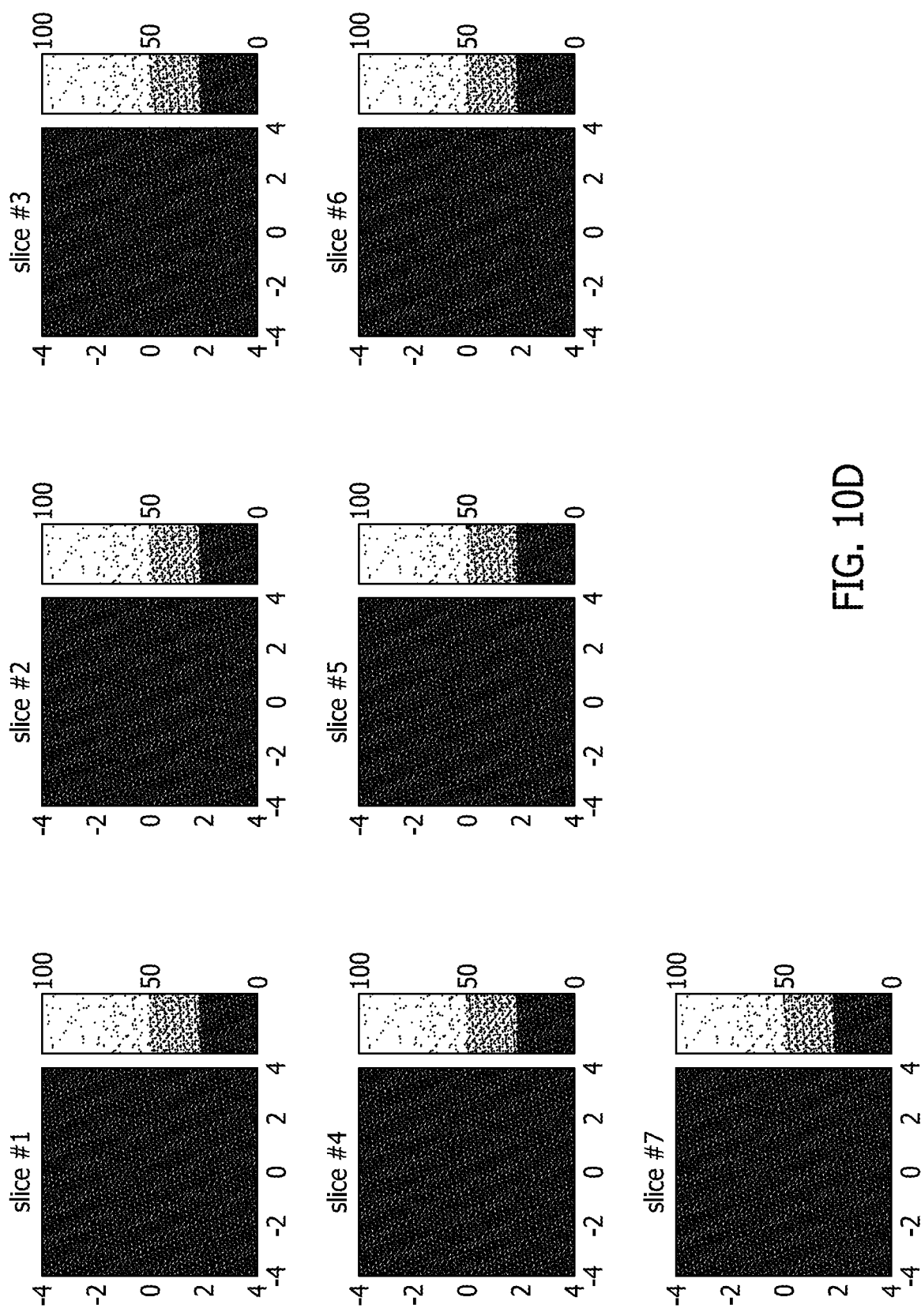
FIG. 10D contains a series of deoxyHb maps for various slices of the breast image of FIG. 10A.

FIG. 10A is a US image of a hypoechoic lobulated mass (pointed by arrow) in the right breast of a 72-year-old woman. US readings from the two readers were 4B and 4C. FIG. 10B shows the tHb maps showing an isolated mass, with a maximum of 106.2 μmol/L. FIG. 10C shows the oxyHb maps, and FIG. 10D shows the deoxyHb maps. The oxyHb map follows the tHb map closely, and the deoxyHb distribution is quite diffused. Core biopsy revealed DCIS, nuclear grade 2. Pathology at surgery revealed 0.6 cm DCIS with intraductal papilloma with atypia and microcalcification.

TABLE 2

| Comparison of Reader Assessments without/with tHb | | | | |
|---|---|---|---|---|
| | Sensitivity | Specificity | PPV | NPV |
| Diagnostic ultrasound only, without tHb data | | | | |
| Reader 1: All malignant lesions | 78.0% | 90.1% | 66.7% | 94.2% |
| Reader 2: All malignant lesions | 81.4% | 83.7% | 55.8% | 94.7% |
| Diagnostic ultrasound, with tHb data | | | | |
| Reader 1: All malignant lesions | 96.6% | 83.3% | 59.4% | 99.0% |
| Reader 2: All malignant lesions | 100% | 77.3% | 52.7% | 100% |

The Study 2 results were further analyzed to assess the potential clinical utility of guided DOT systems and methods in characterizing patients who may not need to be referred for biopsy. The great majority of biopsy lesions are rated as low suspicion BI-RADS 4A or moderately suspicion 4B. A subset of data from patients with 4A and 4B lesions was used for this analysis, where these patients, with low or moderate risk of malignancy, are routinely referred for biopsy. Table 3 shows the number of biopsy referrals categorized by the readers' BI-RADS scores. Many 4A and 4B lesions were benign (94% for both readers). Table 4 shows the number of biopsy referrals categorized by the readers' BI-RADS scores (4A and 4B) combined with tHb data. A conservative tHb threshold of 50 µmol/L was chosen to differentiate lesions based on the amount of vascularization and consequent angiogenesis and probability of malignancy. The number of 4A and 4B lesions that would be referred for biopsy was evaluated based on reader data alone or on reader data in combination with tHb data. Without tHb information, Reader 1 referred 210 patients and Reader 2 referred 195.

TABLE 3

Bi-RADS scores compared with biopsy results (295 lesions)

| Reader Score | Malignant | Benign | Total |
|---|---|---|---|
| Reader 1: 4A/B | 14 | 210 | 224 |
| 4C | 12 | 18 | 30 |
| 5 | 34 | 7 | 41 |
| Reader 2: 4A/B | 13 | 195 | 208 |
| 4C | 25 | 29 | 54 |
| 5 | 22 | 11 | 33 |
| Total | 60 | 235 | 295 |

TABLE 4

4A/4B scores and tHb (unit µmol/L), and biopsy

| | Malignant | | Benign | | |
|---|---|---|---|---|---|
| Reader Score | tHb ≤ 50 | tHb > 50 | tHb ≤ 50 | tHb > 50 | Total |
| Reader 1: 4A | 0 | 0 | 23 | 23 | 46 |
| 4B | 1 | 13 | 71 | 93 | 178 |
| Total | 1 | 13 | 94 | 116 | 224 |
| Reader 2: 4A | 0 | 1 | 21 | 16 | 38 |
| 4B | 0 | 12 | 67 | 91 | 170 |
| Total | 0 | 13 | 88 | 107 | 208 |

When the tHb data were considered using the >50 µmol/L threshold, the number of lesions referred for biopsy decreased to 106 and 120, respectively, for read 1 and reader 2. Comparing with the number of biopsy referrals of 210 and 195 without the tHb information, these reductions are significant. Biopsy referrals for 4A and 4B lesions were decreased by 50% and 39% (an average of 45%) when tHb data were considered, while maintaining a high sensitivity (see Table 5). Furthermore, the only malignant lesion missed by Reader 1 was a low grade 1 cm T1b tumor.

TABLE 5

Reader 1 (224 lesions) and Reader 2 (208 lesions) results for combined 4A/4B lesions with tHb > 50 µmol/L

| | | Biopsy | | |
|---|---|---|---|---|
| | | Malignant | Benign | Total |
| Reader 1 | | | | |
| Test, tHb > 50 µmol/L | Positive | 13 | 93 | 106 |
| | Negative | 1 | 117 | 118 |
| Total | | 14 | 210 | 224 |

TABLE 5-continued

Reader 1 (224 lesions) and Reader 2 (208 lesions) results for combined 4A/4B lesions with tHb > 50 µmol/L

| | | Biopsy | | |
|---|---|---|---|---|
| | | Malignant | Benign | Total |
| Reader 2 | | | | |
| Test, tHb > 50 µmol/L | Positive | 13 | 107 | 120 |
| | Negative | 0 | 88 | 88 |
| Total | | 13 | 195 | 208 |

The tHb data obtained through co-registered guided DOT, therefore, can be used clinically in differentiating malignant breast lesions from benign ones. Used in combination with the diagnostic standard of care, it can reduce the number of unnecessary biopsies with a low risk of malignancy.

As shown above, for 4C lesions, the cancer detection sensitivity for reader 1 was (12 out of 30) and for reader 2 was 46.3% (25 out of 54) (Table 3). The benign categories read as 4C lesions were fibroadenoma (33%-41%), fibrocystic changes (22%-31%, including fibrosis), fat necrosis and inflammatory changes (10-28%), and proliferative lesions (14%-17%). US-guided DOT had 100% cancer detection sensitivity for 4C lesions read by reader 1 and 96% sensitivity for reader 2 when 50 µmol/L was used as a conservative tHb threshold. As for BI-RADS 5 lesions, the cancer detection sensitivity for reader 1 was 82.9% and reader 2 was 66.7% (Table 3). US-guided DOT data was unlikely to have changed the radiologists' decisions on biopsy, but might have downgraded it to 4C or 4B and improved biopsy concordance.

Example 2. Image Reconstruction of the Optimized Functional Images

Constrained Optimization Method

In DOT, the propagation of diffused light through tissue can be described by photon diffusion approximation as:

$$[\nabla^2 + k^2]U(r) = -\frac{1}{D}S(r), k^2 = \frac{-v\mu_a + jw}{D}, D = \frac{1}{3\mu_s'}, \quad \text{Eq. (1)}$$

where S(r) is the equivalent isotropic source and, U(r) is the photon density wave, D is the diffusion coefficient, $j=\sqrt{-1}$, v is the speed of light, w is the modulation frequency of the optical wave, and $\mu_a$ and $\mu_s'$ are the absorption and reduced scattering coefficients, respectively. The inverse problem may be linearized by Born approximation. By digitizing the imaging space into N voxels, the resulted integral equations are formulated as following:

$$[U_{sc}]_{M\times 1} = [W]_{M\times N}[\delta\mu_a]_{N\times 1} = WX, \quad \text{Eq. (2)}$$

where $U_{sc}$ is the measured scattered photon density wave, M is the number of measurements, and $\delta\mu_a$ a denotes the unknown changes of absorption coefficient at each voxel. The weight matrix, W, describes the distribution of diffused wave in the homogenous medium and characterizes the measurement sensitivity to the absorption and scattering changes. The inverse problem can be formulated as an unregularized optimization problem as:

$$f(x) = \arg\min/x\|U_{sc} - WX\|^2 \quad \text{Eq. (3)}$$

During the reconstruction, a dual-zone mesh scheme is used to segment the imaging volume into a lesion region identified by the guiding images, e.g., co-registered US images, and a background region with fine and coarse voxel sizes, respectively. The coarse voxel size is greater than the fine voxel size. This scheme reduces the total number of voxels with unknown optical properties. The conjugate gradient (CG) method may be utilized to iteratively solve the inverse problem. As a result, the target quantification accuracy can be significantly improved. When the lesions are larger, the total number of fine voxels and coarse voxels, N, can be much larger than the total measurements, M, which is the number of sources×the number of detectors×2 (e.g., =14×9×2=252 in some embodiments) counting for both amplitude and phase data. Due to the correlated nature of diffused light measured at closely spaced sources and detector positions in addition to measurement noise, increasing the number of sources and detectors does not effectively mitigate the ill-conditioned nature of the DOT inversion problem.

The inverse problem is formulated as:

$$f(x) = \underset{X}{\mathrm{argmin}}\left(\|U_{sc} - WX\|^2 + \frac{\lambda}{2}\|(X - X^0)\|^2\right), \quad \text{Eq. (4)}$$

where $X^0$ is a preliminary estimate of the optical properties that can be determined from the measured data and $\lambda$ is a regularization parameter. A Newton or conjugate gradient optimization method is used to approximately solve Eq. (4). In various embodiments, no spatial or temporal filters were used on solution $f(x)$.

Truncated Pseudoinverse as an Initial Estimate

A truncated pseudoinverse (PINV) operator $W_{PINV}^{-1}$ of W is used to form the preliminary estimate of $X^0$ as $X^0 = W_{PINV}^{-1} U_{sc}$, which is included in the second part of Eq. (4). According to singular value decomposition (SVD) theory, W can be decomposed as:

$$W = \Sigma_{n=1}^{R} \sqrt{\sigma_n} u_n v_n^\dagger, \quad \text{Eq. (5)}$$

$\{u_n\}$ and $\{v_n\}$ are left and right singular vector of W or orthonormal eigenvector of $WW^\dagger$, $\{\sigma_n\}$ are nonzero eigenvalues of $W^\dagger W$ or $WW^\dagger$ or $\{\sqrt{\sigma_n}\}$ are the singular values of W, and R is the number of nonzero singular values.

Moore-Penrose pseudoinverse (MPP) of W is, $$W_{PINV}^{-1} = \sum_{n=1}^{R} \frac{1}{\sqrt{\sigma_n}} v_n u_n^\dagger \quad \text{Eq. (6)}$$

Based on the linear equation Eq. (2), $$\tilde{X} = W_{PINV}^{-1} U_{sc} = \sum_{n=1}^{R} \frac{1}{\sqrt{\sigma_n}} v_n u_n^\dagger U_{sc} \quad \text{Eq. (7)}$$

Since measurement contains noise, denoted as n, $U_{sc} = U_{noiseless} + n$. Then the reconstructed absorption $\tilde{X}$ is given as:

$$\tilde{X} = W_{PINV}^{-1}(U_{noiseless} + n) \quad \text{Eq. (8)}$$
$$= X + X_{noise}, \; X_{noise} = \sum_{n=1}^{R} \frac{1}{\sqrt{\sigma_n}} v_n u_n^\dagger n$$

For small singular values, where $\sqrt{\sigma_n} \to 0$, $X_{noise}$ may contain image artifacts.

In the truncated MPP approach, a threshold value $\sqrt{\sigma_{th}}$ is used to choose singular values, and the initial solution using MPP is:

$$X^0 = W_{PINV}^{-1} U_{sc} = \quad \text{Eq. (9)}$$
$$\Sigma_{n=1}^{R'} \frac{1}{\sqrt{\sigma_n}} v_n u_n^\dagger U_{sc}, \; \sqrt{\sigma_1}, \sqrt{\sigma_2}, \ldots \ldots \ldots \ldots \sqrt{\sigma_{R'}} \geq \sqrt{\sigma_{th}}$$

$\sqrt{\sigma_{th}}$ may be chosen as 10% of $\sqrt{\sigma_1}$ as a cut-off value, where $\sqrt{\sigma_1}$ is the largest singular value of the weight matrix W. From the truncated pseudoinverse, a preliminary estimate of unknown optical properties can be obtained. A projection operation is used to suppress pixels outside the region of interest identified by a sphere B obtained from measurements of co-registered ultrasound images. This projected absorption map is used as an initial solution for Newton or Conjugate gradient search method.

Newton Optimization Method

The Newton method uses $2^{nd}$ derivative of objective function (known as hessian) to calculate a $2^{nd}$ order search direction resulting in quadratic convergence rate. We reformulate our penalized least square problem as a quadratic optimization problem, $$f(x) \frac{1}{2} X^T Q X - b^T X - c$$

$$Q = 2W^T W + \lambda I, \; b = 2W^T U_{sc} + \lambda X^0 \quad \text{Eq. (10)}$$

The hessian is positive definite when $\lambda > 0$. Our solution is iteratively updated using following equations, $$X^{k+1} = X^k - (\nabla^2 f(X))^{-1}(\nabla f(x)), \; \nabla f(x) = QX - b, \; \nabla^2 f(X) = Q \quad \text{Eq. (11)}$$

The iteration process is terminated when change of objective function between successive iterations become smaller than a preset tolerance level. In various embodiments, the regularization parameter is chosen based on the tumor size measured from the guiding images, such as ultrasound images. For example, regularization parameter $\lambda$ is chosen as $\lambda = p\sqrt{\sigma_1}$, where $\sqrt{\sigma_1}$ is the largest singular value of the weight matrix, and p is proportional to the tumor size.

Choice of regularization parameter, $\lambda$, affects the reconstruction. If $\lambda$ is too small, the penalty or regularization may not have any effect on reconstruction. On the other hand, a large $\lambda$ heavily penalizes the data fidelity term and solution may not converge near true minimum of unregularized objective function. In our approach, $\lambda$ is chosen as $\lambda = p\sqrt{\sigma_1}$, which decreases with background reduced scattering coefficient $\mu_{s0}'$ and increases with background absorption coefficient $\mu_{a0}$. Thus, for higher background $\mu_{a0}$, $\lambda$ regulates more to improve the conditioning of the Q matrix (see Eq. (10)). Additionally, because the huge difference between the first and the rest of the singular values, $\lambda/\sigma_n$ increases with n and therefore $\lambda$ regulates more for smaller singular values and further improves the conditioning of Q matrix. In various embodiments, the regularization parameter is determined by trial and error using phantom data to ensure convergence, reconstruction accuracy and lower image artifacts.

Conjugate Gradient Optimization Method

The Conjugate gradient (CG) method is an iterative technique for solving symmetric positive definite linear systems of equations. This method was investigated both with regularization and without regularization. For the unregularized optimization formulation as given in Eq. (3), W is positive semi-definite because it possesses singular values that take on zero values. From phantom experiments using absorbers with known optical properties, three iterations were determined as a stopping criterion because the reconstructed absorption coefficients after three iterations were close to known values. For the regularized least square formula $Q=2W^TW+\frac{1}{2}\lambda I$, and Q is, by construction, symmetric and positive semi-definite. For a choice of $\lambda > 0$, Q is a positive definite matrix since the lower bound for the singular values of Q is $$\frac{\lambda}{2}.$$

Again, $\lambda = p\sqrt{\sigma_1}$, is chosen with p proportional to the target or tumor size measured from the ultrasound.

Comparison of Five Reconstruction Methods

Five reconstruction methods were compared using phantom and clinical data. The five methods use zero as an initial estimate of target optical properties for regularized Newton optimization (Newton Zero initial) and regularized CG optimization (CG Zero initial); using PINV as an initial estimate of target optical properties for regularized Newton optimization (Newton PINV initial), regularized CG optimization (CG PINV initial), and using zero initial estimate and unregularized CG.

Data Acquisition of the US-Guided DOT System

In the exemplary embodiment, a US-guided DOT system was used, where an ultrasound device was the imaging device used to acquire guiding data. The system comprised a commercial US system and a DOT device. Four laser diodes of wavelength 740, 780, 808 and 830 nm respectively were used to deliver light modulated at 140 MHz carrier frequency to tissue. Each laser diode was multiplexed to 9 positions on a hand-held probe and 14 photomultiplier detectors (PMT) were used to detect reflected light via light guides. A customized A/D board sampled detected signals from each patient at both lesion and contralateral normal breast. The sampled signals were then stored in a computing device, such as a personal computer. Multiple datasets acquired from contralateral normal breast were used to compute a composite or compound reference. A composite reference was considered as a homogeneous reference and used fitted optical absorption ($\mu_{a0}$) and reduced scattering ($\mu_{s0}'$) to calculate W for each wavelength. Lesion absorption maps of 4 wavelengths were reconstructed and total hemoglobin map was calculated from the absorption maps using absorption coefficients for these four wavelengths.

Example 3. Phantom Experiments

Figure 11:
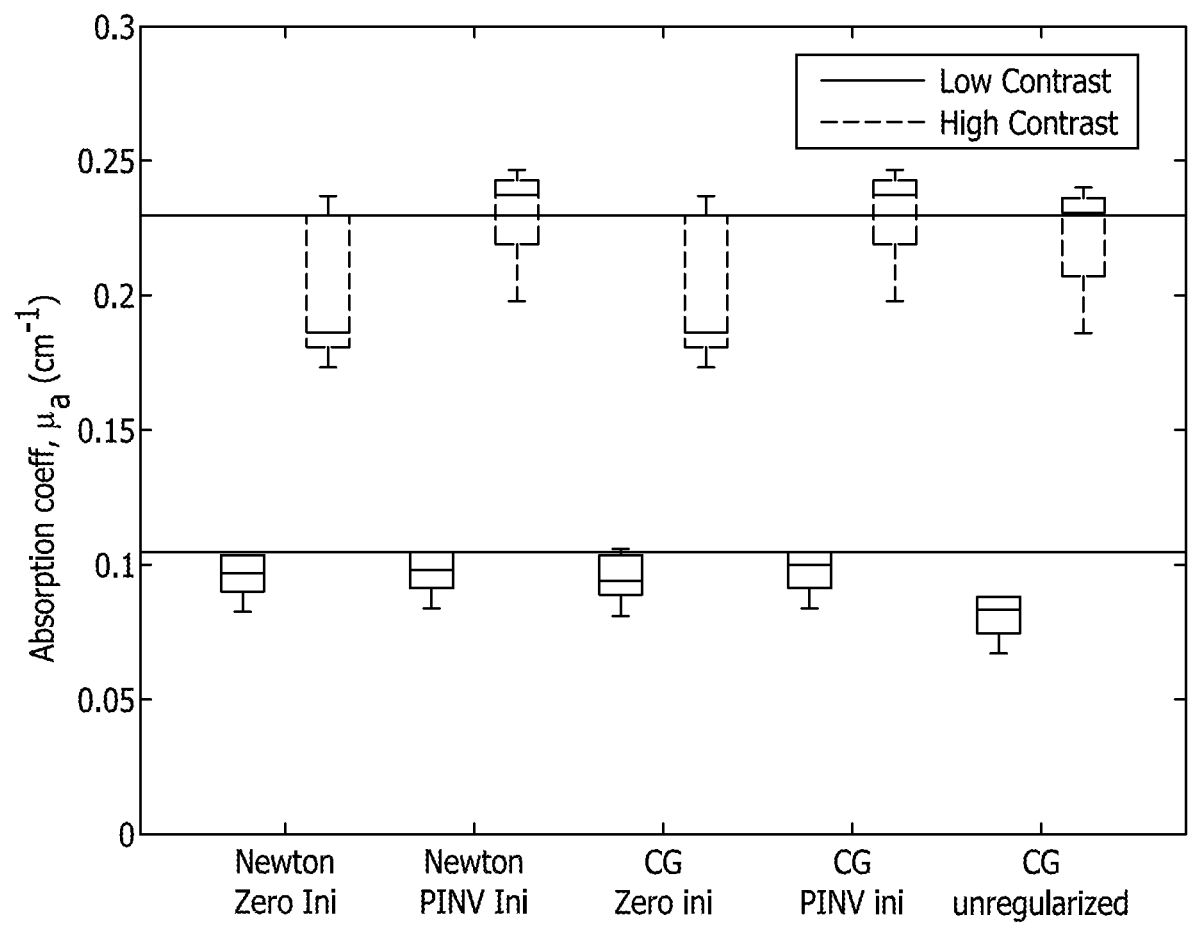
FIG. 11 is a box plot comparing absorption coefficients obtained using various reconstruction methods using DOT imaging data obtained from a variety of absorbers within an imaging phantom.

Phantom experiments were performed with solid ball phantoms of different sizes and different optical contrasts to emulate tumors. These phantoms were submerged in intralipid solution of P a in the range of 0.02-0.03 cm$^{-1}$ and $\mu_s'$ in the range of 7 to 8 cm$^{-1}$ that emulated homogeneous background tissue. Three solid balls having diameters of 1, 2 and 3 cm respectively were submerged at depths of from 1.5 cm to 3 cm in 0.5 cm increments. The calibrated high and low contrast phantoms had $\mu_a=0.23$ cm$^{-1}$ and $\mu_a=0.11$ cm$^{-1}$, mimicking malignant and benign lesions, respectively. An absorption map for each phantom location, size and contrast was reconstructed and maximum $\mu_a$ was obtained for quantitative comparison. Average reconstructed maximum $\mu_a$'s from all phantoms using five reconstruction methods are provided in Table 6(a) and shown in FIG. 11. FIG. 11 is a box plot of phantom data obtained from phantoms having diameter from 1 to 3 cm of high contrast (dashed line) and low contrast (solid line) located at different depths (1.5-3.5 cm center depth) using zero and PINV as an initial guess and Newton as the optimization method, respectively (first and second columns), zero and PINV as initial guess and CG as the optimization method, respectively (third and fourth columns), and unregularized CG (last column). Errors of both high and low contrast phantoms reconstructed using these five different methods are given in Table 6(b) below. As seen from Tables 6(a) and 6(b), Newton and CG with PINV as an initial image accurately estimated absorption coefficients while Newton and CG with a zero initial produced larger errors. Unregularized CG provided better estimates for high contrast phantoms but resulted in under reconstruction for low contrast phantoms.

TABLE 6(a)

Maximum reconstructed absorption (cm$^{-1}$) (mean ± standard deviation) for phantom

|  | Newton with zero Ini | Newton with PINV ini | CG with zero ini | CG with PINV ini | CG unconstrained |
|---|---|---|---|---|---|
| Reconstructed $\mu_a$ (low contrast) | 0.097 ± 0.018 | 0.099 ± 0.016 | 0.093 ± 0.012 | 0.100 ± 0.017 | 0.107 ± 0.069 |
| Reconstructed $\mu_a$ (high contrast) | 0.191 ± 0.042 | 0.229 ± 0.021 | 0.191 ± 0.041 | 0.228 ± 0.021 | 0.222 ± 0.027 |

TABLE 6(b)

Errors (mean ± standard deviation) in reconstructed absorption coefficient using different method

|  | Newton with zero Ini | Newton with PINV ini | CG with zero ini | CG with PINV ini | CG unconstrained |
|---|---|---|---|---|---|
| Error (low contrast) | 11.6 ± 13.8% | 0.04 ± 9.1% | 11.8 ± 13.2% | 0.1 ± 9.0% | 3.5 ± 9.9% |
| Error (high contrast) | 12.0 ± 16.1% | 9.6 ± 14.6% | 15.6 ± 10.9% | 8.8 ± 15.8% | 26.5 ± 8.5% |

Example 4. Patient Data

Clinical data of 20 patients were obtained using the system and method disclosed herein. Based on biopsy results, 10 patients had benign lesions and 10 patients had cancers.

Figure 12A:
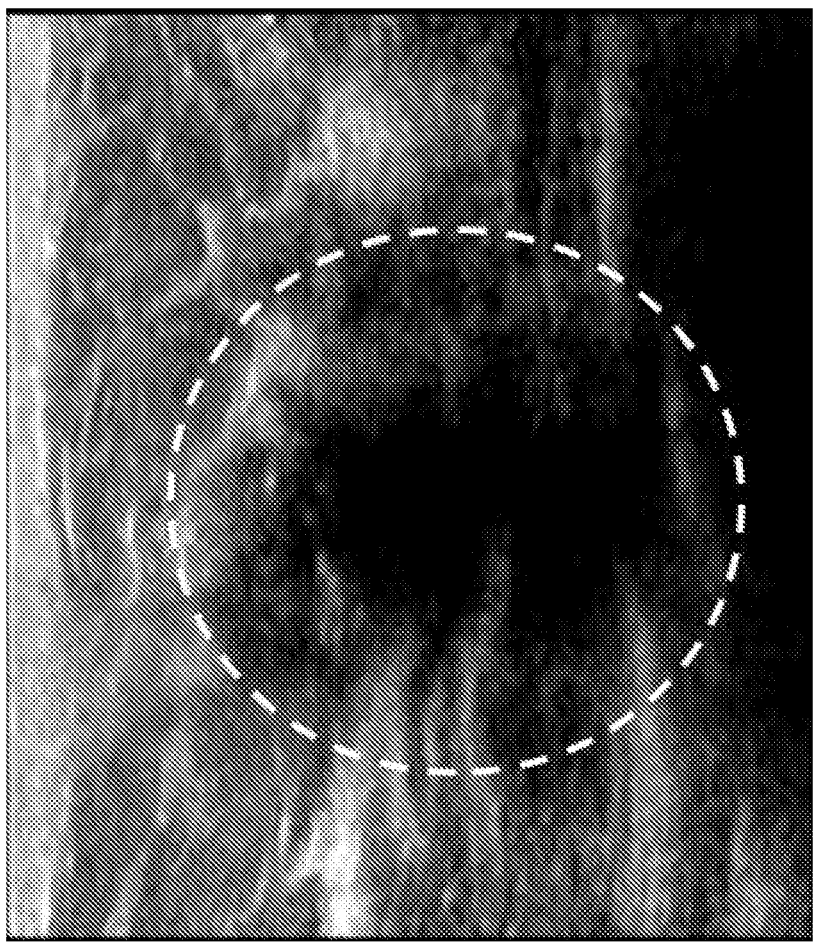
FIG. 12A is an ultrasound image of a breast of yet another patient.
Figure 12B:
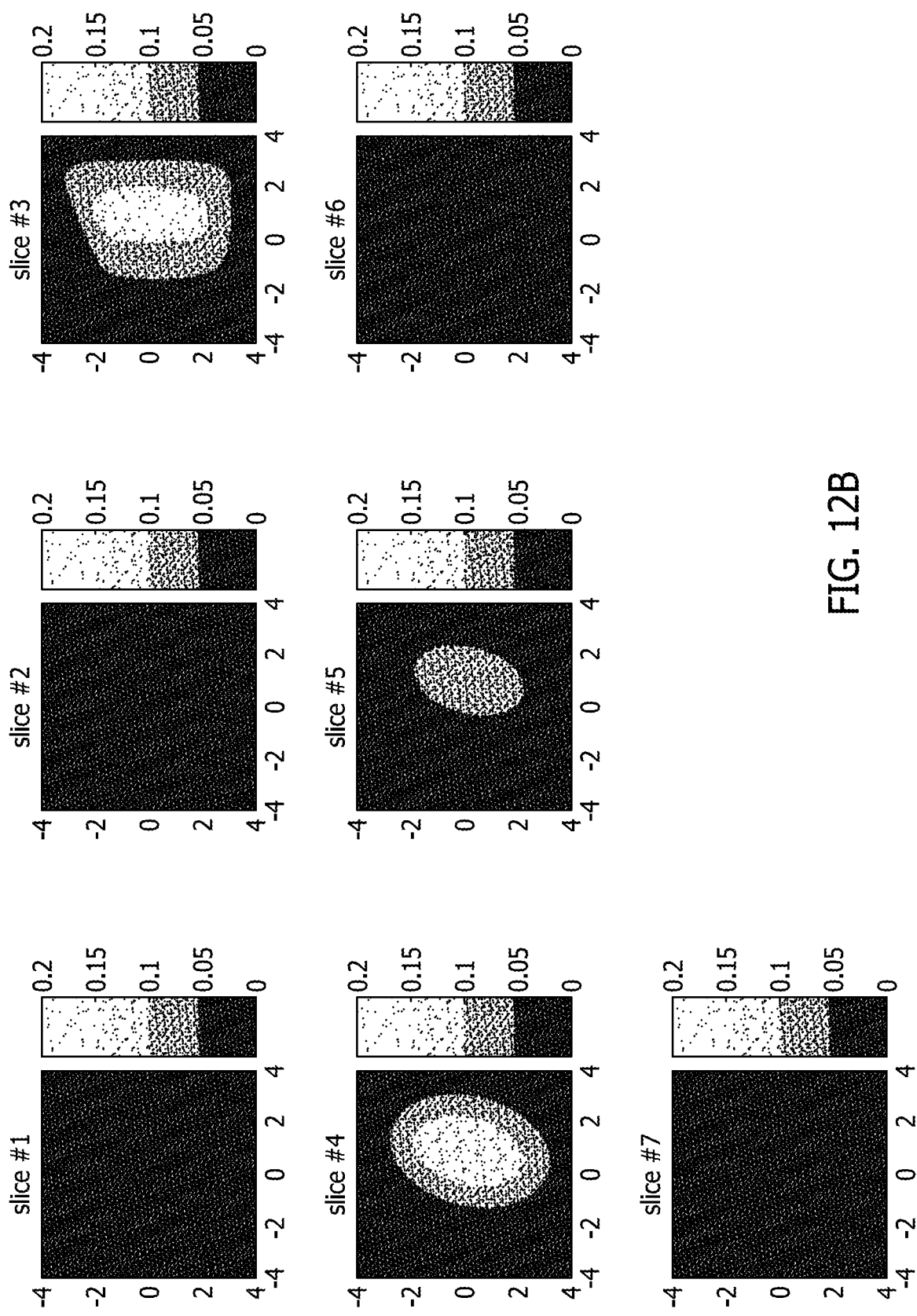
FIG. 12B shows the truncated pseudoinverse initial estimate of the absorption maps of various slices of the breast image of FIG. 12A.
Figure 12C:
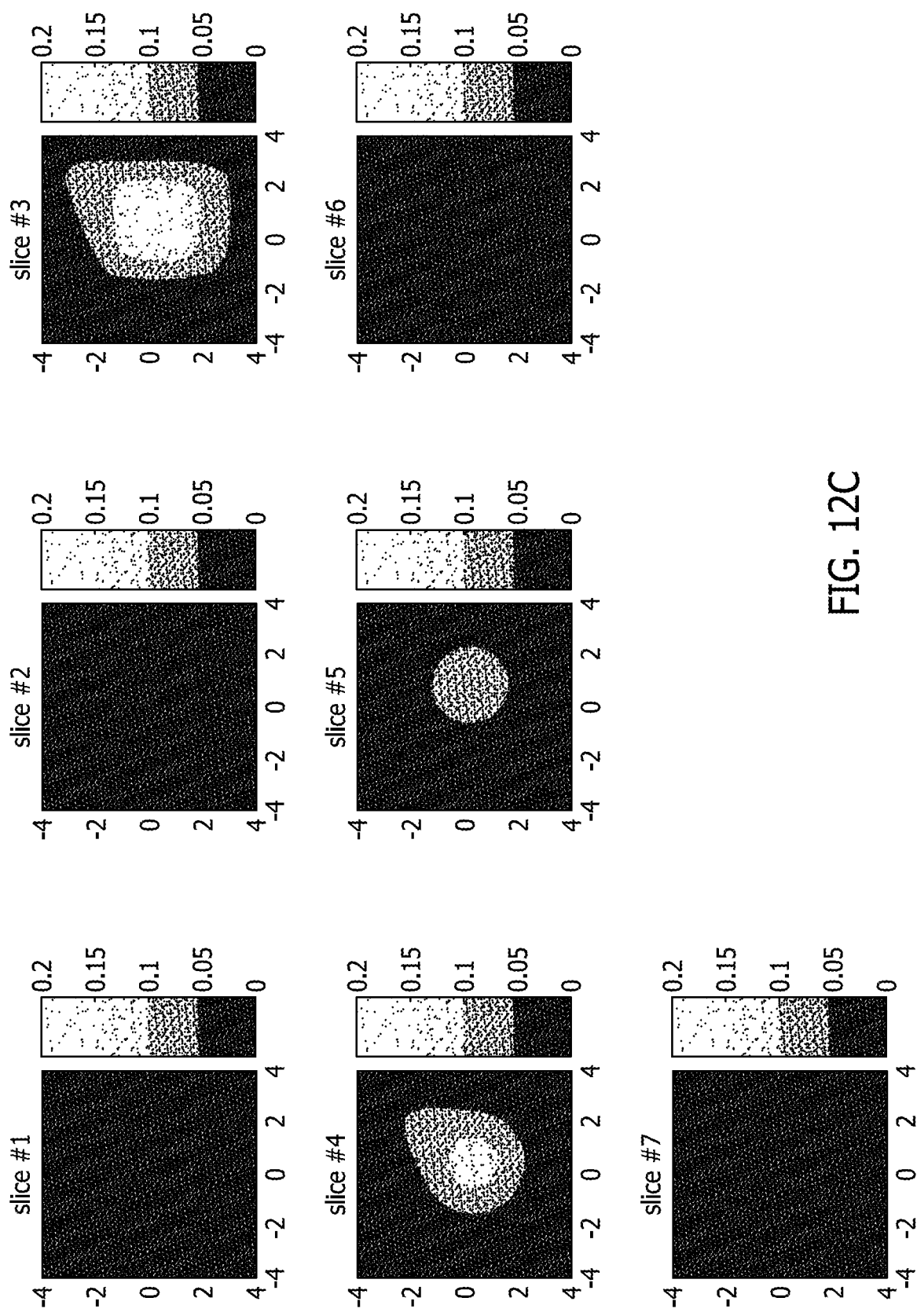
FIG. 12C contains a series of absorption maps for various slices of the breast image of FIG. 12A, generated by a regularized Newton method with zero as the initial estimate.
Figure 12D:
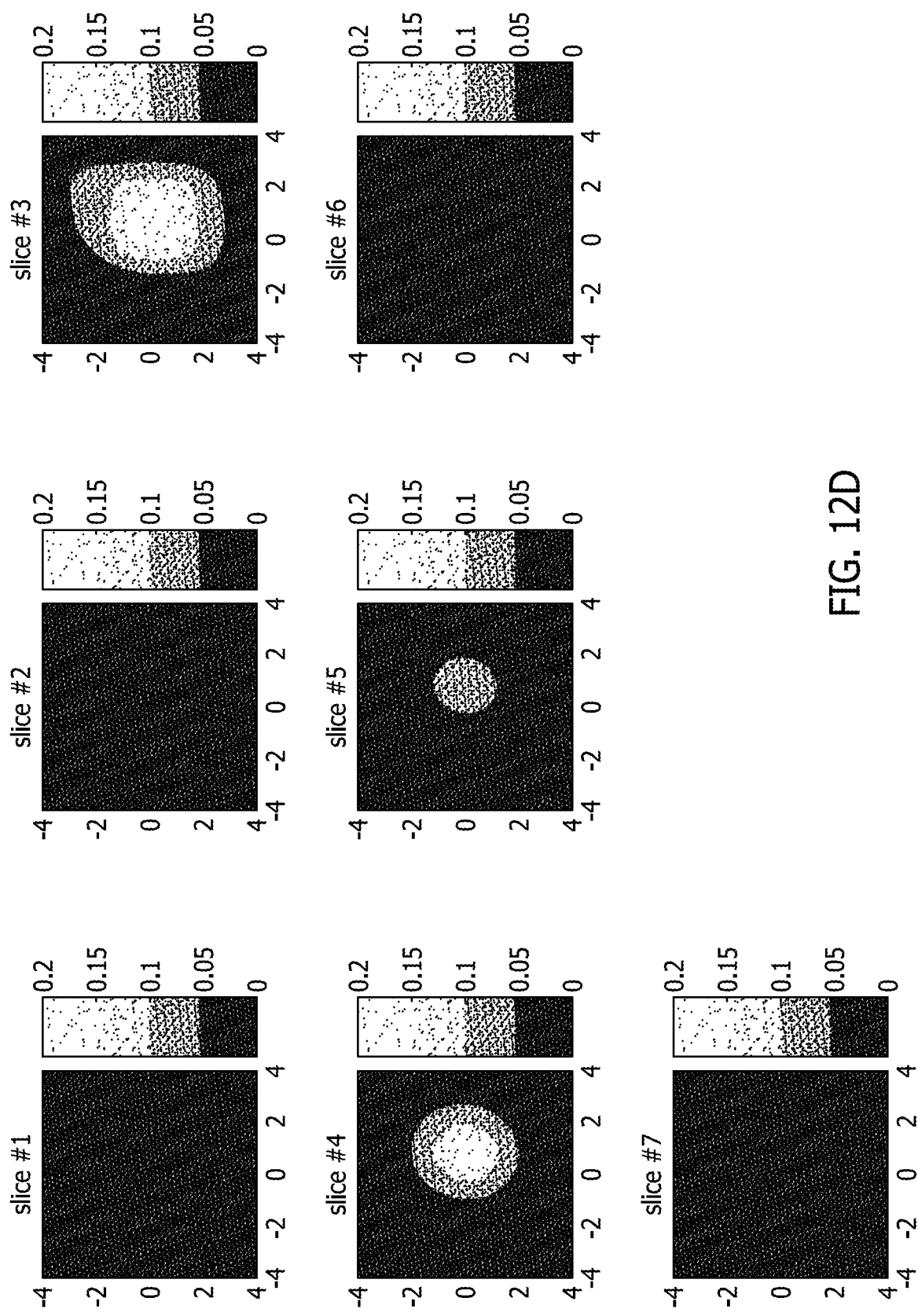
FIG. 12D contains a series of absorption maps for various slices of the breast image of FIG. 12A, generated by a regularized Newton method with the truncated pseudoinverse initial estimate.
Figure 12E:
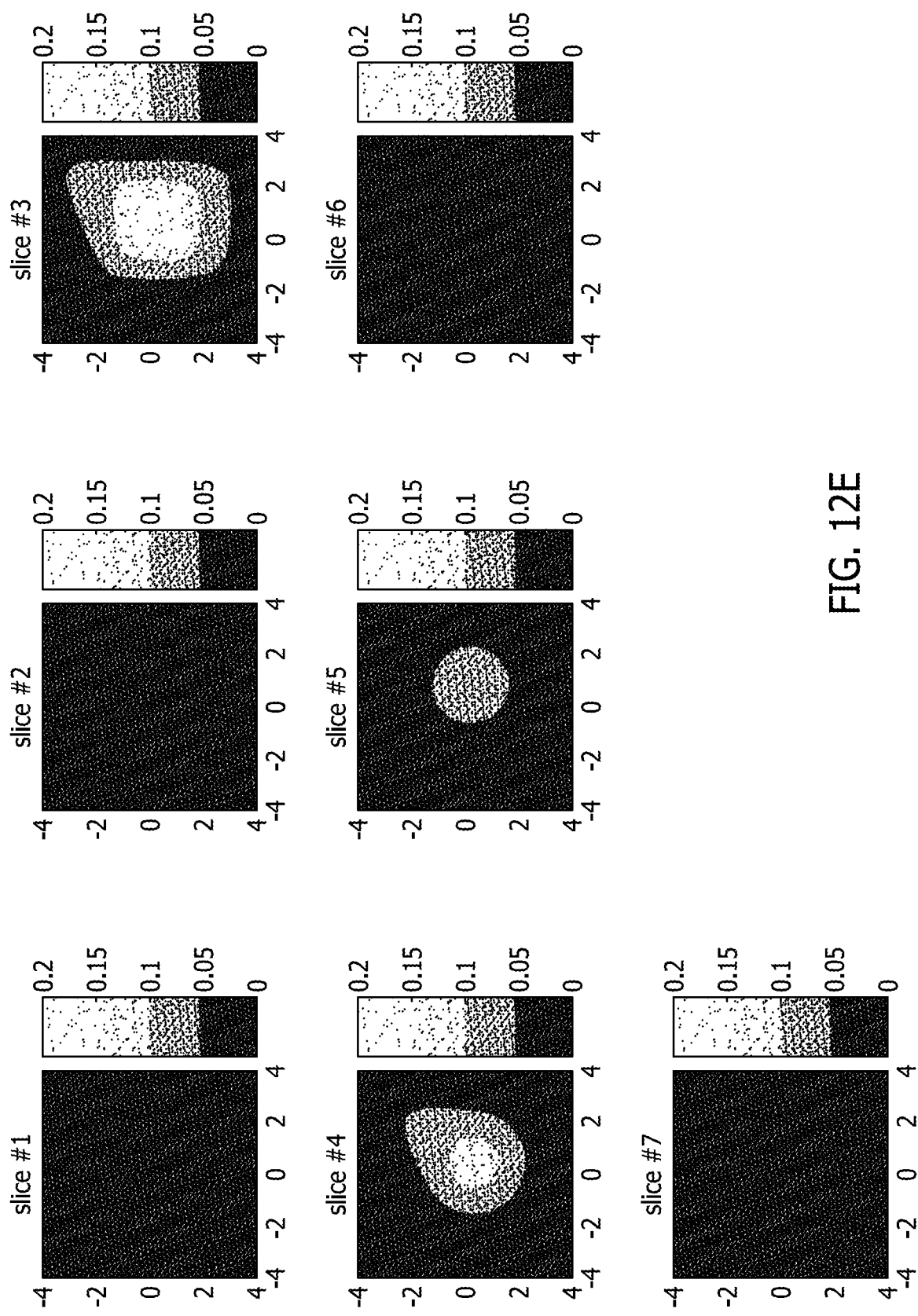
FIG. 12E contains a series of absorption maps for various slices of the breast image of FIG. 12A, generated by a regularized conjugate gradient (CG) method with zero as the initial estimate.
Figure 12F:
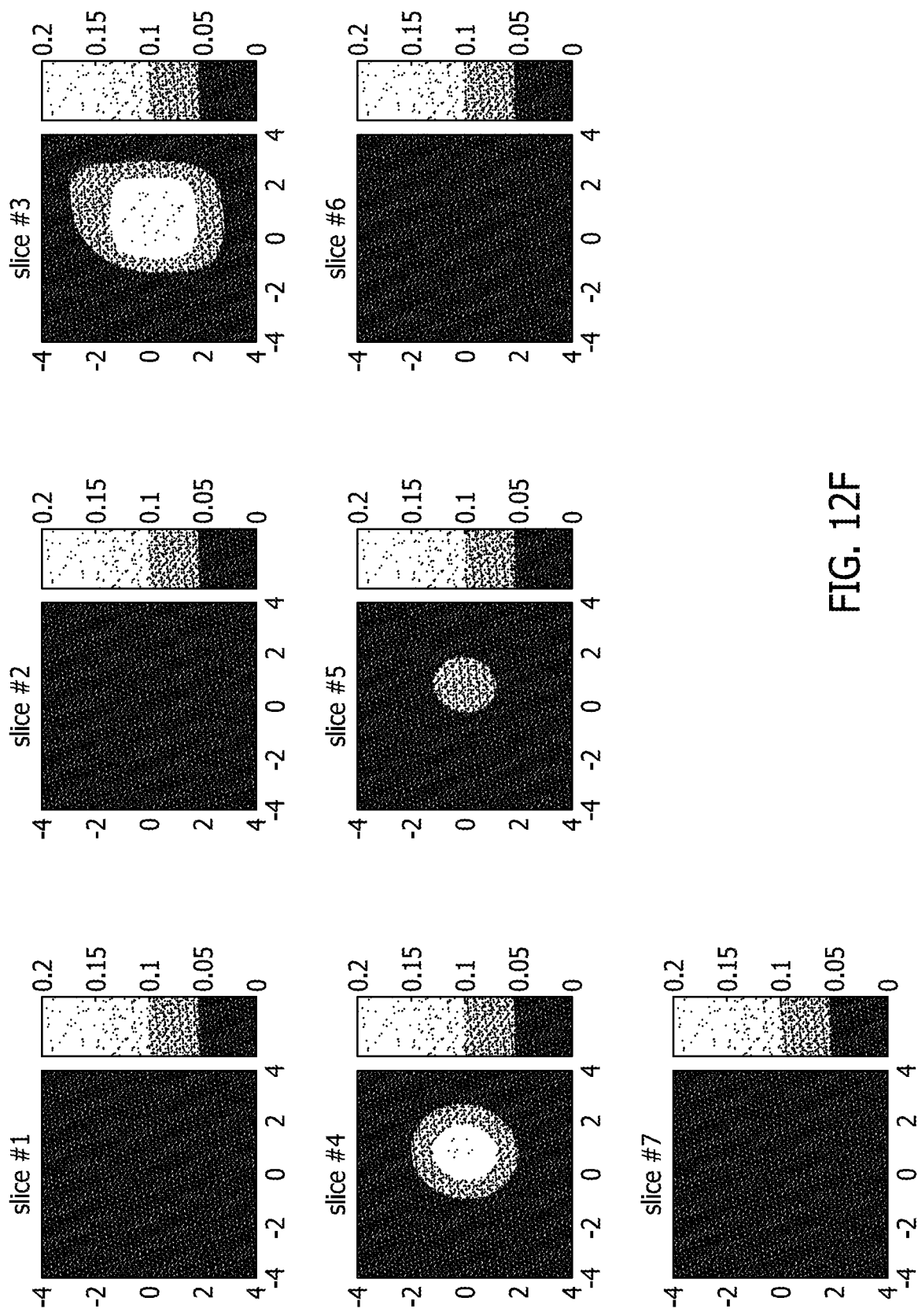
FIG. 12F contains a series of absorption maps for various slices of the breast image of FIG. 12A, generated by a regularized CG method with the truncated pseudoinverse initial estimate.
Figure 12G:
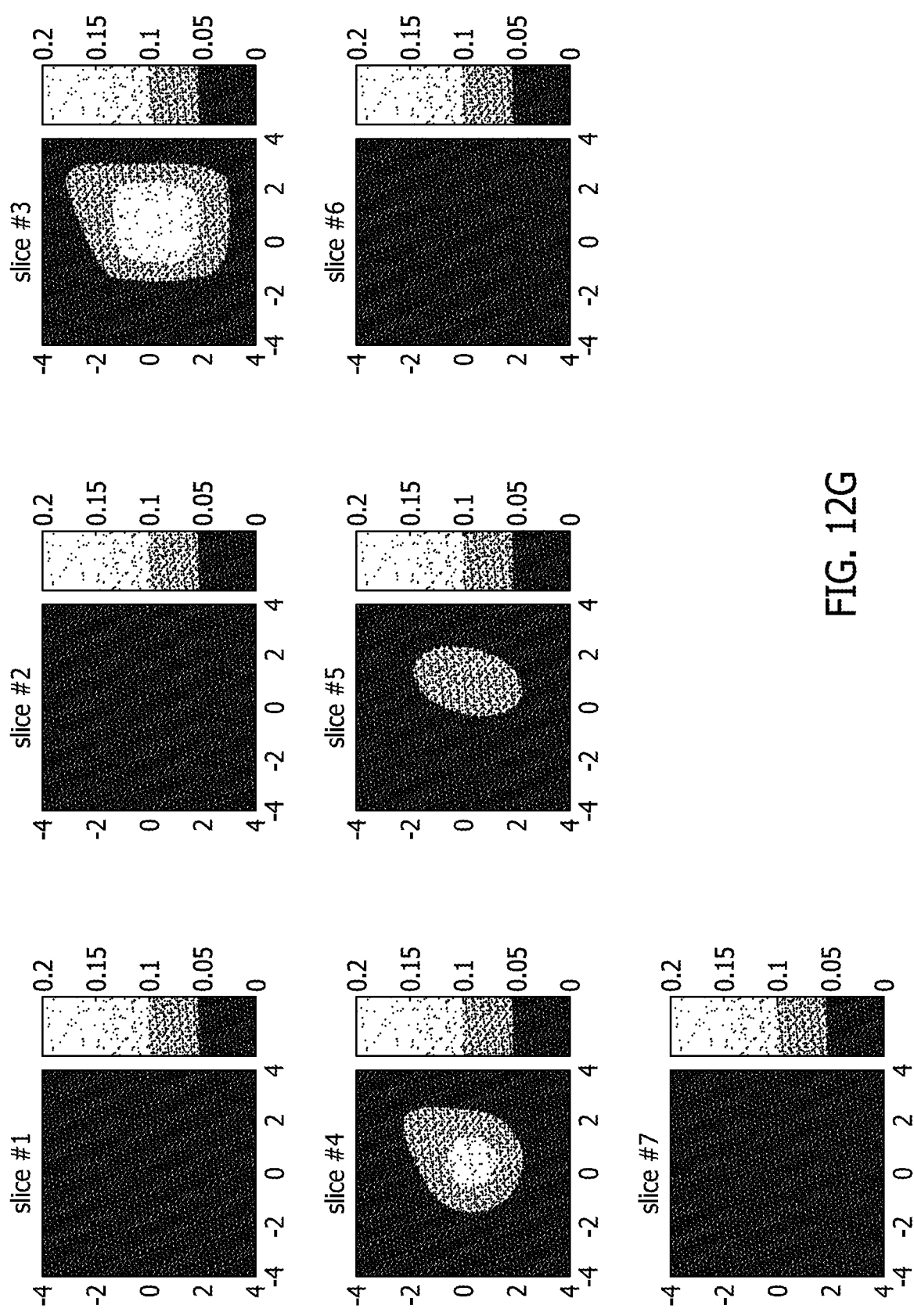
FIG. 12G contains a series of absorption maps for various slices of the breast image of FIG. 12A, generated by an unregularized CG method.

An example of a cancer case is shown in FIGS. 12A, 12B, 12C, 12D, 12E, 12F, and 12G. FIGS. 12B, 12C, 12D, 12E, 12F, and 12G depict the reconstructed absorption maps at 780 nm wavelength. FIG. 12A shows a co-registered US image with the suspicious lesion marked by a circle. FIG. 12B shows the absorption maps reconstructed by PINV initial, where maximum $\mu_a$=0.194 cm$^{-1}$. FIG. 12C shows the absorption maps reconstructed by Newton with zero initial, where maximum $\mu_a$=0.179 cm$^{-1}$. FIG. 12D shows the absorption maps reconstructed by Newton with PINV initial, where maximum $\mu_a$=0.268 cm$^{-1}$. FIG. 12E shows the absorption maps reconstructed by regularized CG with zero initial, where maximum $\mu_a$=0.179 cm$^{-1}$. FIG. 12F shows the absorption maps reconstructed by regularized CG with PINV initial, where maximum $\mu_a$=0.267 cm$^{-1}$. FIG. 12G shows the absorption maps reconstructed by unregularized CG, where maximum $\mu_a$=0.216 cm$^{-1}$.

Each set of maps in each figures in FIGS. 12B, 12C, 12D, 12E, 12F, and 12G comprise 7 sub-images marked as slice 1 to 7 and each sub-image shows an x-y plane distribution of absorption coefficients at the depth of from 0.5 cm to 3.5 cm from the skin surface. The spacing between the sub-images in terms of depth is 0.5 cm. The color bar is absorption coefficients in cm$^{-1}$. We chose the $\mu$ a display range from 0 to 0.2 cm$^{-1}$ because most of the reconstructed absorption values fall within this range. The dimension of the sub-image is 8 cm×8 cm with scales marked as from −4 cm to 4 cm in both X and Y axis. Absorption maps reconstructed with the five methods showed similar lesion position and shape, but the method of Newton with PINV initial (FIG. 12D) yielded the highest reconstructed $\mu_a$=0.268 cm$^{-1}$.

Figure 13A:
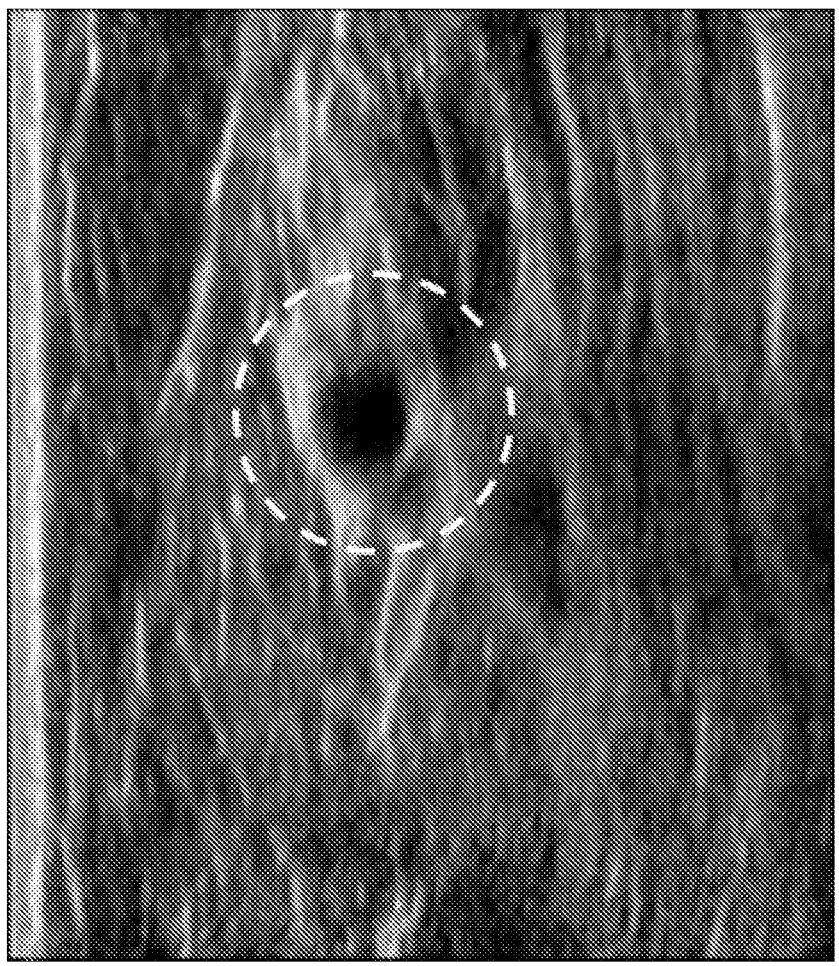
FIG. 13A is an ultrasound image of a breast of yet another patient.
Figure 13B:
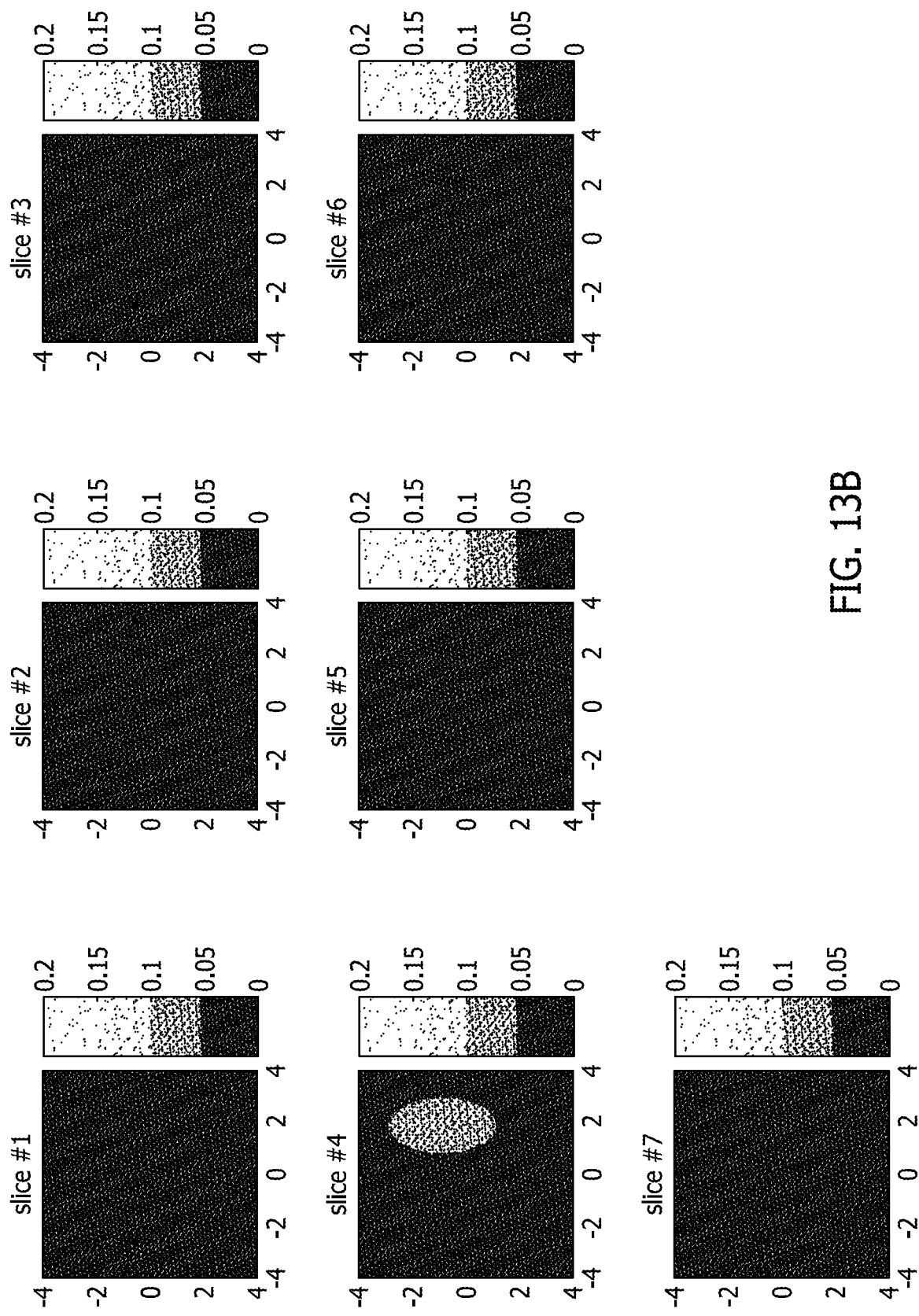
FIG. 13B contains a series of truncated pseudoinverse initial estimates of the absorption maps of various slices of the breast image of FIG. 13A.
Figure 13C:
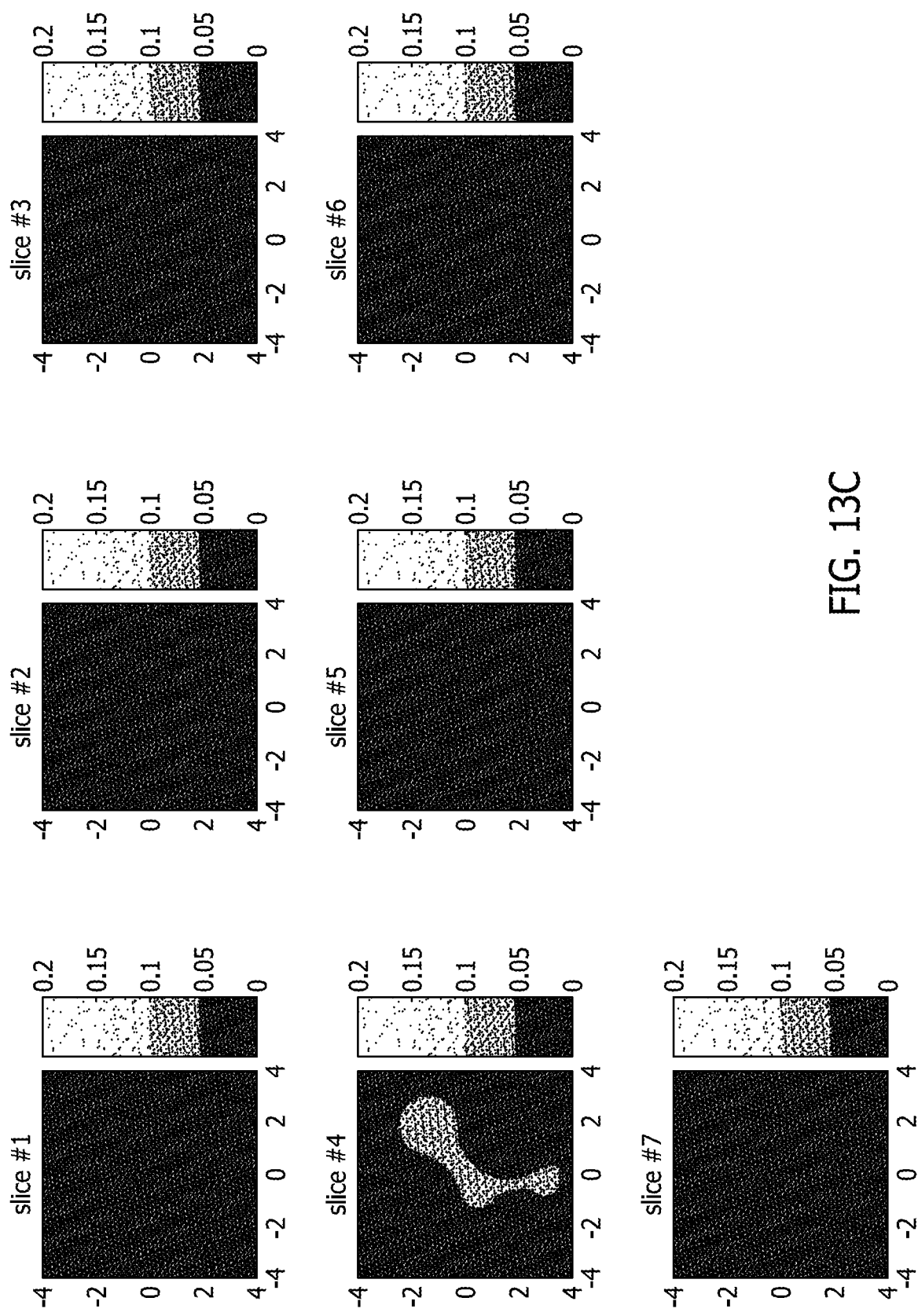
FIG. 13C contains a series of absorption maps for various slices of the breast image of FIG. 13A, generated by a regularized Newton method with zero as the initial estimate.
Figure 13D:
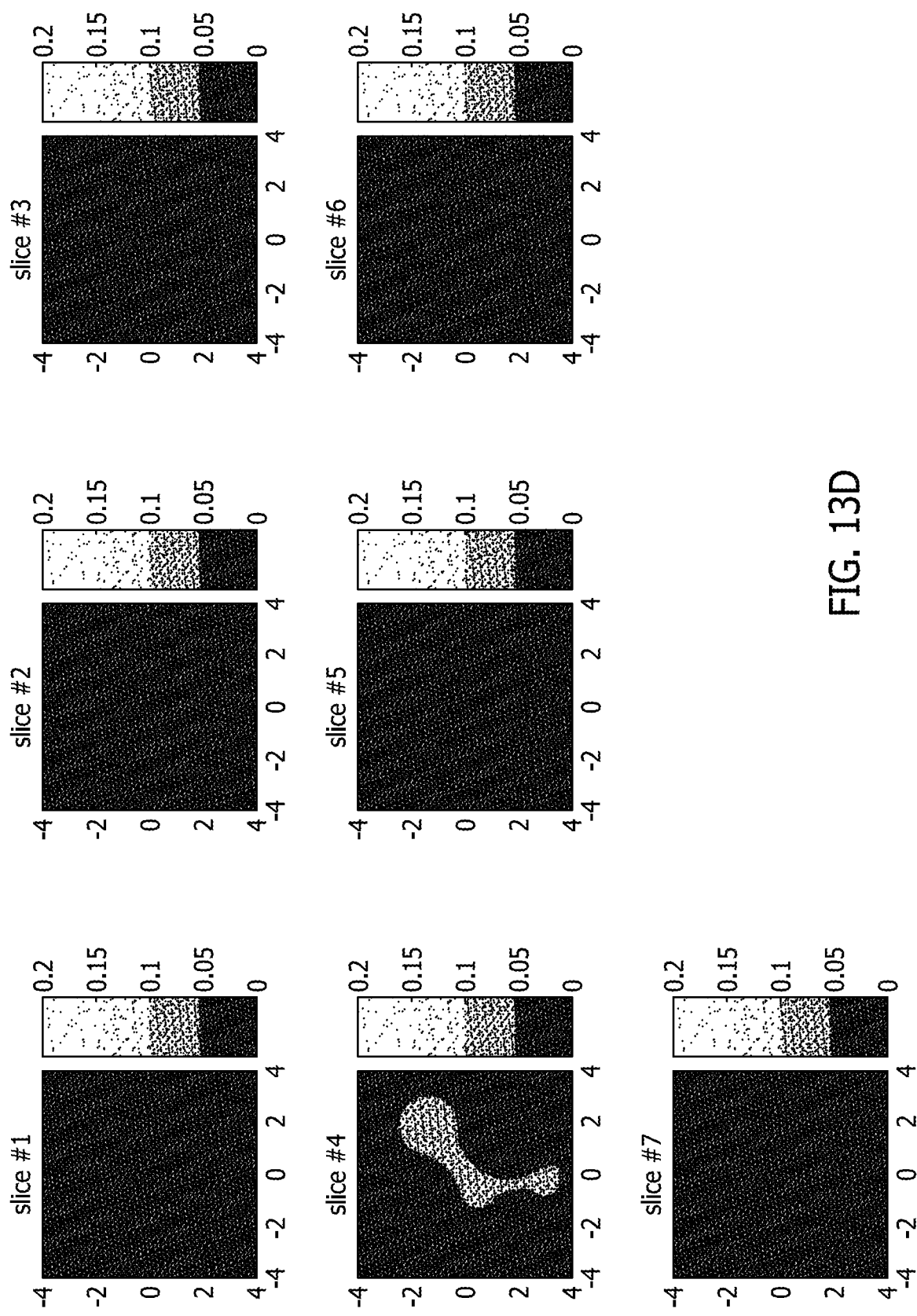
FIG. 13D contains a series of absorption maps for various slices of the breast image of FIG. 13A, generated by a regularized Newton method with the truncated pseudoinverse initial estimate.
Figure 13E:
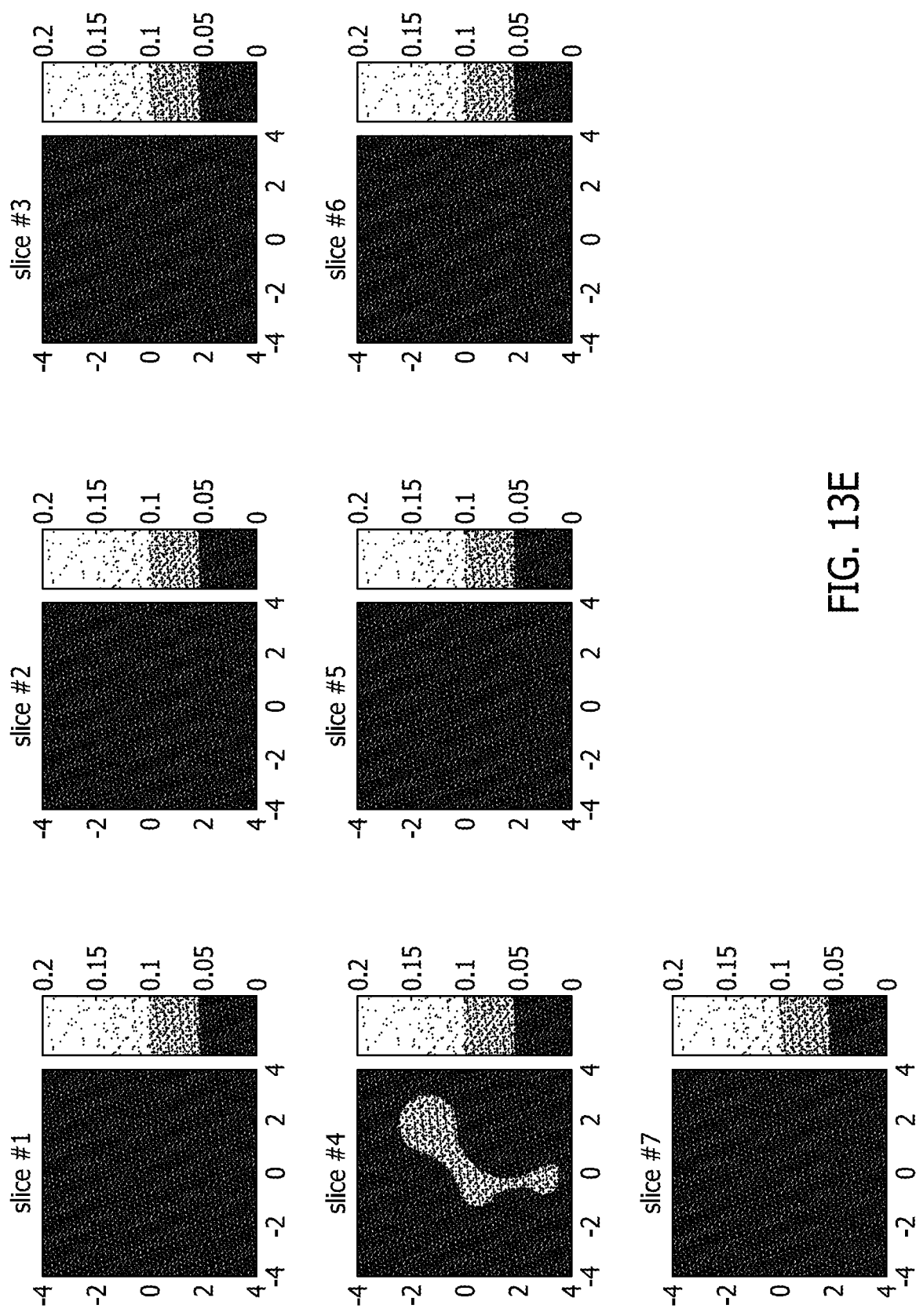
FIG. 13E contains a series of absorption maps for various slices of the breast image of FIG. 13A, generated by a regularized conjugate gradient (CG) method with zero as the initial estimate.
Figure 13F:
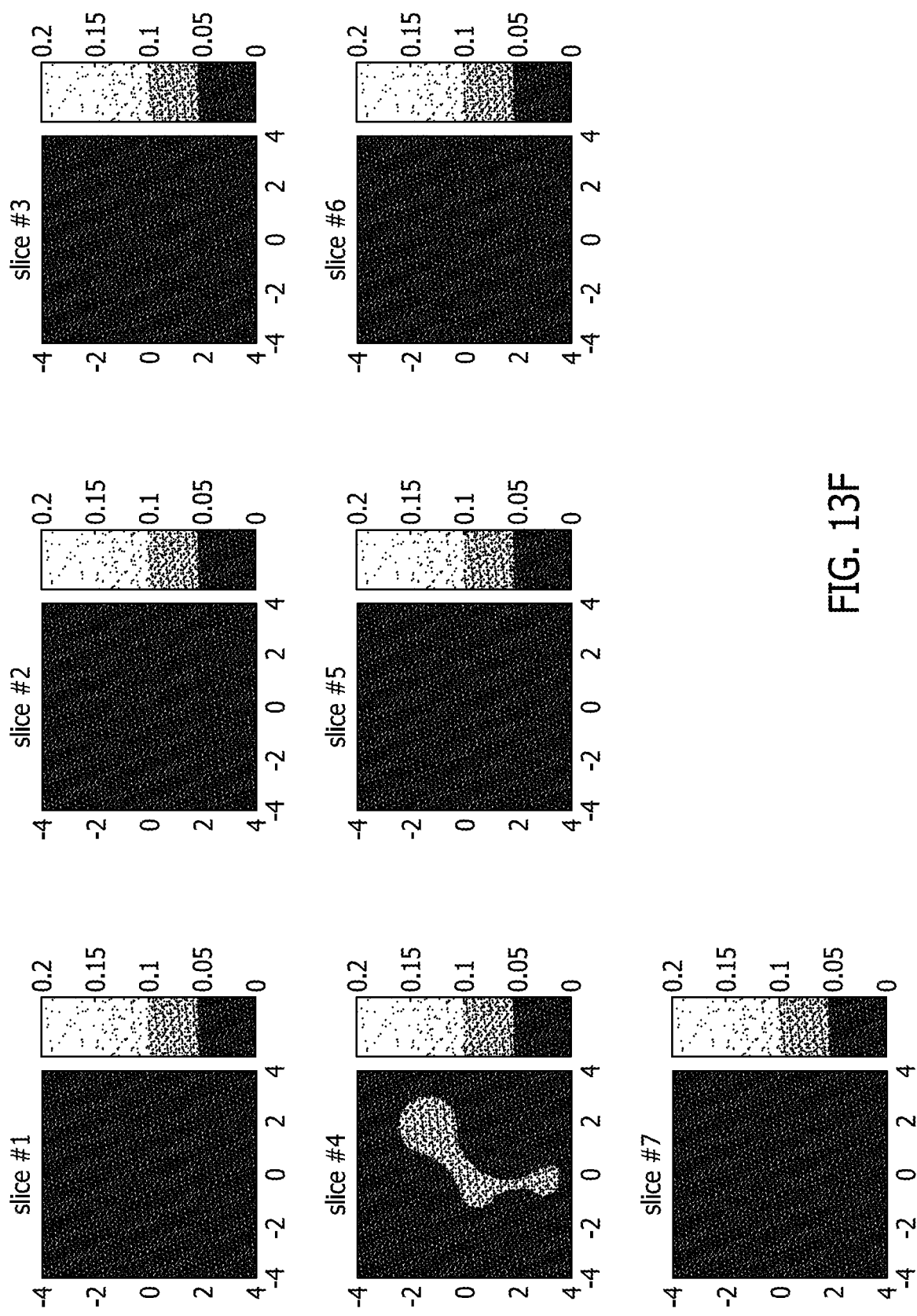
FIG. 13F contains a series of absorption maps for various slices of the breast image of FIG. 13A, generated by a regularized CG method with the truncated pseudoinverse initial estimate.
Figure 13G:
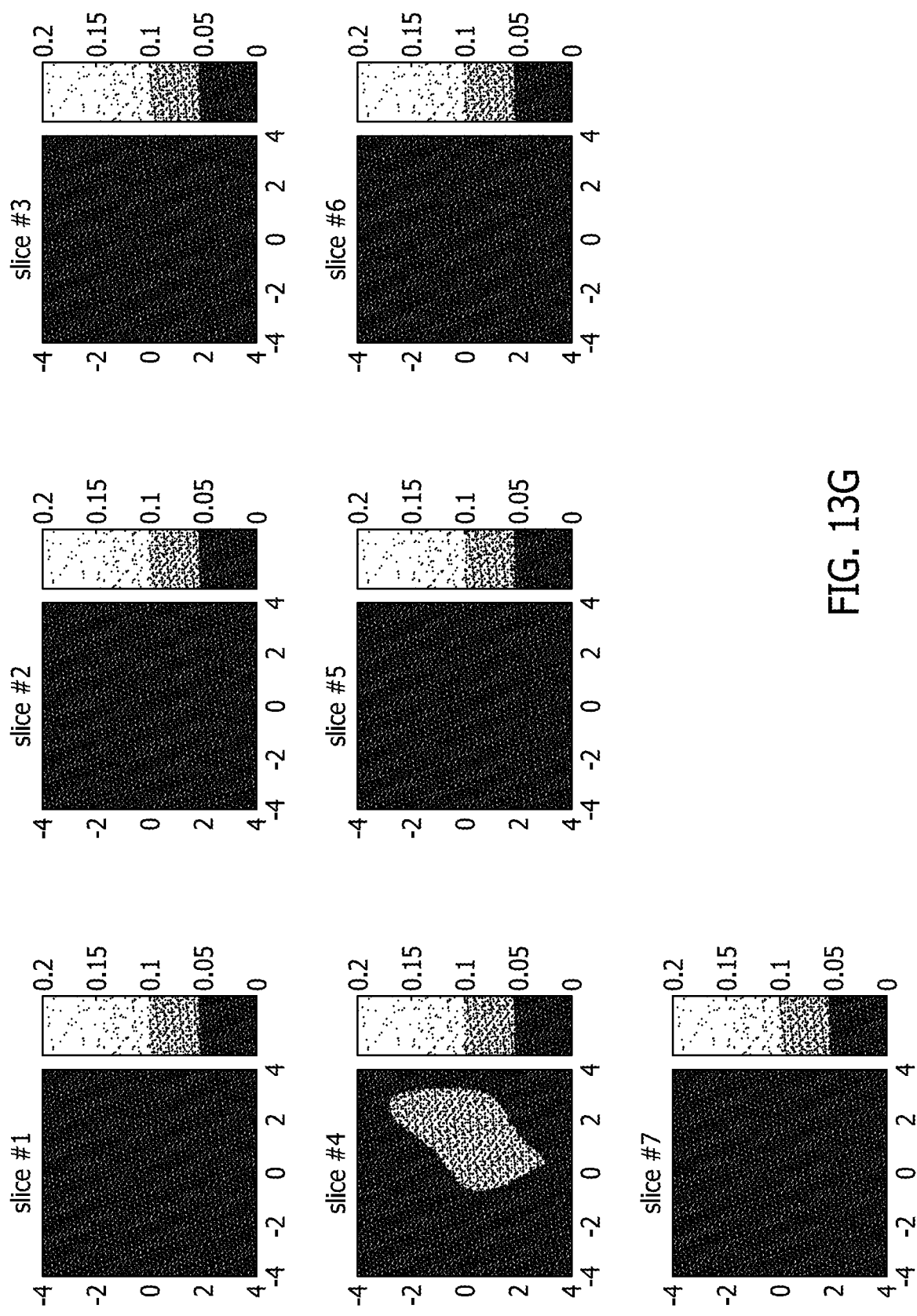
FIG. 13G contains a series of absorption maps for various slices of the breast image of FIG. 13A, generated by an unregularized CG method.

An example of a benign lesion is shown in FIGS. 13A, 13B, 13C, 13D, 13E, 13F, and 13G. FIGS. 13B, 13C, 13D, 13E, 13F, and 13G show reconstructed absorption maps at the 780 nm wavelength of a benign case. FIG. 13A is a co-registered US image with the suspicious lesion marked by a circle. FIG. 13B is PINV initial estimate images, where maximum $\mu_a$=0.076 cm$^{-1}$. FIG. 13C is reconstructed by Newton with zero initial, where maximum $\mu_a$=0.078 cm$^{-1}$. FIG. 13D is reconstructed by Newton with PINV initial, where maximum $\mu_a$=0.087 cm$^{-1}$. FIG. 13E is reconstructed by regularized CG with zero initial, where maximum $\mu_a$=0.077 cm$^{-1}$. FIG. 13F is reconstructed by regularized CG with PINV initial, where maximum $\mu_a$=0.088 cm$^{-1}$. FIG. 13G is reconstructed by unregularized CG, where maximum $\mu_a$=0.092 cm$^{-1}$. The absorption maps in FIGS. 13B, 13C, 13D, 13E, 13F, and 13G have the same scale as in FIGS. 12B, 12C, 12D, 12E, 12F, and 12G.

Figure 14:
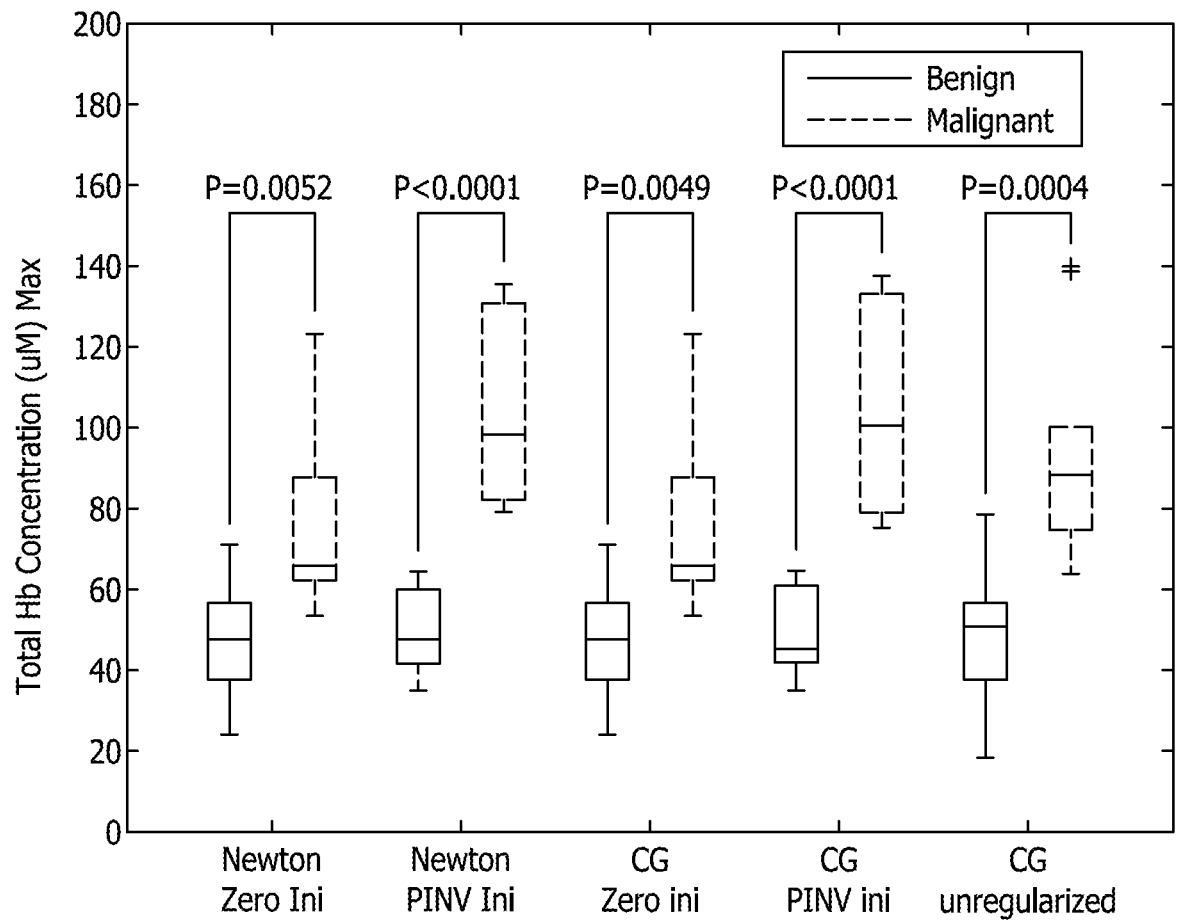
FIG. 14 is a box plot comparing tHb of 20 patients obtained using five different reconstruction methods.

A box plot of maximum tHb of 20 clinical cases (20 patients with 10 patients having a malignant tumor (dashed line), and 10 patients having a benign tumor (solid line) reconstructed with the five different methods is shown in FIG. 14. The first column and the second column summarize tHb concentrations reconstructed by a Newton method, with the first column using zero as the initial estimate and the second column using PINV as the initial estimate. The third and fourth columns summarize tHb reconstructed by CG, with the third column using zero as the initial estimate and the fourth column using PINV as the initial estimate. The last column summarizes tHb reconstructed by unregularized CG. A two-sample t test was performed between malignant and benign groups for each method. The Newton or CG method with PINV as an initial estimate provided the highest statistical significance.

Additionally, the malignant to benign contrast ratios were 1.61, 2.11, 1.61, 2.07, and 1.93 for Newton's with zero initial, PINV initial, CG zero initial, PINV initial and unregularized CG respectively. The average and standard deviation of maximum tHb concentration obtained from each method is summarized in Table 7. For benign cases, reconstructed tHb was comparable using five methods, however, for malignant cases the tHb contrast was much higher when Newton's and CG were used with the PINV initial estimate.

TABLE 7

| | tHb (µmol/L) for clinical cases using different methods | | | | |
|---|---|---|---|---|---|
| | Newton with zero Ini | Newton with PINV ini | CG with zero ini | CG with PINV ini | CG unregularized |
| Total Hb conc. (Benign) | 47.5 ± 14.2 | 49.4 ± 10.6 | 47.5 ± 14.3 | 50.4 ± 9.8 | 48.5 ± 16.3 |
| Total Hb conc. (Malignant) | 76.4 ± 23.9 | 104.2 ± 23.6 | 76.5 ± 23.8 | 104.2 ± 23.6 | 93.5 ± 26.9 |

Example 5: Convergence Speed of Reconstruction Methods

Figure 15:
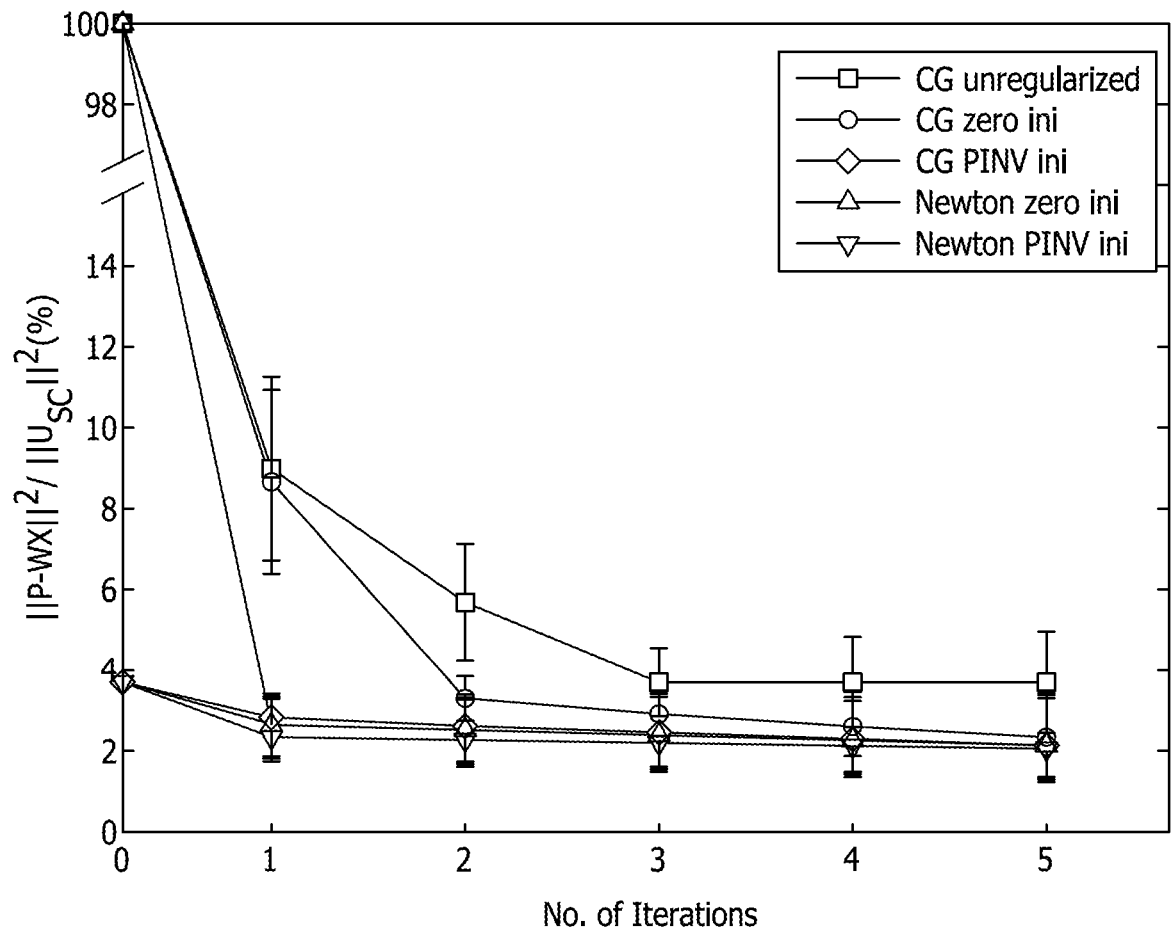
FIG. 15 is a graph summarizing the least square errors of five different reconstruction methods at different iterations of reconstruction.

When an iterative image reconstruction algorithm converges quickly, reconstructed images can be provided for on-site diagnosis by physicians. To compare the convergence of different reconstruction methods, the Least Square Error (LSE), $\|U_{sc}-WX\|^2$ for each method was normalized to the power of the scattered field, $\|U^{sc}\|^2$, which served as the initial objective function for unregularized CG method. Shown in FIG. 15 are the mean and standard deviations of normalized LSE for the five methods using phantom data. Truncated pseudoinverse provided a good initial guess which reduced the initial LSE, $\|U_{sc}-WX\|^2$, to 4% of the power of the scattered field, $\|U_{sc}\|^2$. Newton and CG with PINV as an initial estimate converged in 1 and 2 iterations, respectively. Newton and CG with zero initial converged in 1 and 3 iterations, respectively, and the residual LSE of CG was slightly higher than that with PINV as an initial. Unregularized CG converged in 3 iterations.

Example 6: Target Centroid Error

To compare different reconstruction methods, the target centroid error, i.e., the absolute difference between the center of a phantom target measured by co-registered US and the centroid of corresponding reconstructed target absorption map, was calculated as a measure of reconstruction quality. Phantom data of both low and high contrast phantom targets of 1 cm diameter located at different depths and measured at 780 nm were used to estimate the centroid error and results are shown in Table 8. The MATLAB function 'regionprop' was used to estimate the centroid of the target absorption map and the difference between the estimated centroid and the measured target center from corresponding co-registered US was calculated. As seen from Table 8, the target centroid error which was less than one voxel size of 0.25 cm did not depend on the reconstruction method. Thus, all reconstruction methods provided essentially the same target centroid.

TABLE 8

Object centroid error (Δx, Δy) (mean ± standard deviation) for phantom data

| | Newton with zero ini | Newton with PINV ini | CG with zero ini | CG with PINV ini | CG unregularized |
|---|---|---|---|---|---|
| Object centroid Error (Δx) | 0.157 ± 0.093 | 0.157 ± 0.093 | 0.157 ± 0.093 | 0.157 ± 0.093 | 0.163 ± 0.091 |
| Object centroid Error (Δy) | 0.225 ± 0.101 | 0.225 ± 0.101 | 0.225 ± 0.101 | 0.225 ± 0.101 | 0.190 ± 0.069 |

Example 7: Automated Method of Outlier Removal and Data Selection

Fast data acquisition of US-guided DOT system allows the collection of several data sets during one imaging session. The data contains multiple data sets from both lesion and contralateral reference breast. An automated method for outlier removal and data selection is introduced to eliminate the effect of inaccurate measurements. The block diagram of the procedures is provided in FIG. 16.

Figure 16:
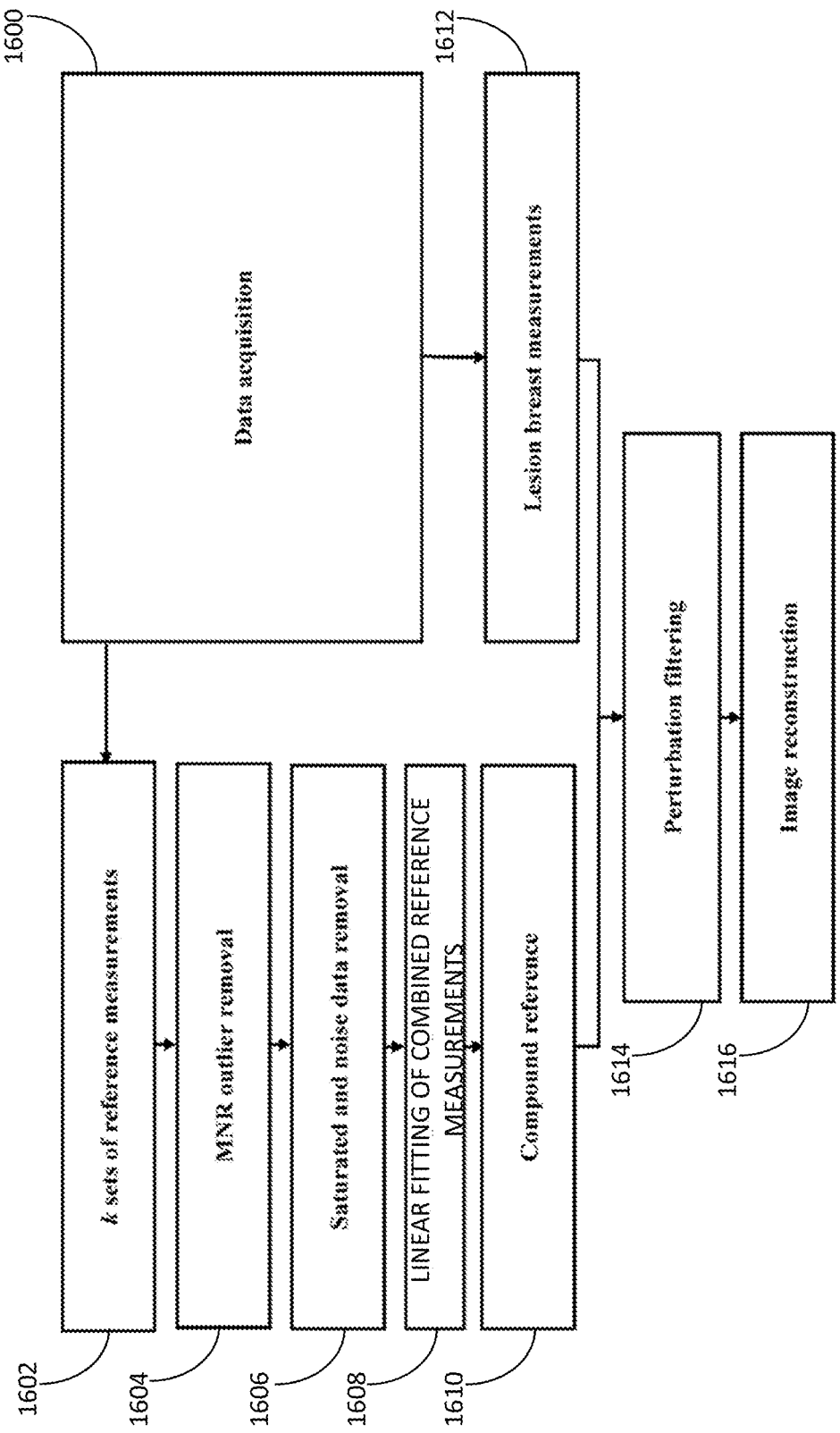
FIG. 16 shows a flow chart of an example automated method for generating optimized functional images FIG. 17 contains a series of amplitude and phase profiles of reference data sets before preprocessing (left column), after preprocessing (center column), and the final compound reference dataset (right column)

As illustrated in the flowchart of FIG. 16, imaging datasets of a breast containing a lesion and a contralateral breast of a patient are obtained at 1600. Multiple sets of reference measurements produced using the contralateral breast measurements were used to form a single high quality data set at 1602. An MNR outlier removal procedure is performed at 1604 as described above to eliminate the highly inaccurate measurements (outliers) with a criterion based on the distribution of data collected at each source detector pair. A piece-linear fitting is used at 1606 to reject the source-detector pair measurements obtained from the saturated PMTs. An iterative fitting of residue of the remaining data is calculated at 1608 to further eliminate inaccurate measurements based on the linearity of fitted results of the reference measurements of all source-detector pairs. A least-square error method is used at 1610 to form the most accurate reference data set from the remaining measurements.

Lesion breast imaging measurements are produced from the imaging dataset from the lesion breast of the patient at 1612 and combined with the compound reference as described above to produce a perturbation dataset, which is subjected to perturbation filtering at 1614. The perturbation filtering in various embodiments is based on analysis obtained from a semi-infinite analytical solution of light propagation in tissue as described above. The perturbation filtering at 1614 forms accurate perturbation sets that are more robust to outlier and inaccurate measurements. The perturbation set produced at 1614 is used as an initial image estimate to perform image reconstruction at 1616 to produce an optimized reconstructed image based on the measurements obtained by the DOT device. Additional details of the selected steps illustrated in FIG. 16 are described in detail below.

Outlier Rejection in Reference Measurements

Each data set contains measurements from s sources and d detectors with the total number of m=s×d measurements. The system used in this study provides 90 source-detector measurements per data set. A total of k data sets containing a total of k×s×d measurements collected at the reference site are used for selecting a best reference data set. In general, k ranges from about 12 to about 18. Since a frequency domain DOT system is used for data acquisition, each data set consists of amplitude and phase data at each voxel. The maximum normed residual (MNR) is a widely used statistical test to address the problem of outlier rejection that has shown outstanding performance in both linear and nonlinear data. The MNR test is based on the largest absolute deviation from the sample mean in units of the sample standard deviation. In various embodiments, the MNR test is applied to remove outliers for each source-detector pair within the k data sets.

In various aspects, each outlier measurement is expunged from each source-detector pair data set based a criterion described below. An upper critical value of the t-distribution with k–2 degrees of freedom is calculated, and an outlier threshold $G_{Threshold}(i)$ is obtained based on Eq. (12).

$$G_{Threshold}(i) = \frac{k-1}{\sqrt{k}} \sqrt{\frac{t^2_{\frac{\alpha}{2k}, k-2}(i)}{k - 2 + t^2_{\frac{\alpha}{2k}, k-2}(i)}}. \quad \text{Eq. (12)}$$

where $G_{Threshold}(i)$ denotes the outlier threshold for the $i^{th}$ source-detector pair, $$t^2_{\frac{\alpha}{2k}, k-2}(i)$$

denotes the upper critical value of the t-distribution with k–2 degrees of freedom, and a represents the level of significance which determines the strictness of outlier removal procedure. By changing the value of a to a value ranging from 0 to 1, the total number of the outliers and the significance of these outliers removed from the database may be modulated. To find the optimal value of a, the outlier removal process is performed for different significance levels ranging from 0.01 to 0.5. In one embodiment, the optimal value of a is set to 0.05 based on visual examination of the removed outliers. This optimal value is selected in a way that the test only removes the significant outlier data. A G value is determined as an absolute deviation of the data point from mean value of the measurements and normalized by standard deviation. Any data point corresponding to maximum G value which has absolute deviation higher than the threshold is classified as an outlier and removed from the reference data set.

In various aspects, the MNR test is iterated until no further outliers are classified in the reference dataset. The MNR test is performed for both amplitude and phase measurements separately. If any data point in either amplitude or phase measurements is classified as an outlier, both amplitude and phase measurements are removed from the reference data sets.

Saturation and Noise Data Rejection in Reference Datasets

In addition to outliers in the reference measurements, detector saturation is another common problem in DOT that can happen as a result of higher light intensity detected at a shorter source detector distance. Each PMT may saturate at a different light intensity level. A semi-infinite analytic solution predicts that the logarithm of the detected amplitude for each source-detector pair multiplied by square distance of that specific source-detector pair, referred as logarithmic amplitude, should linearly decrease with the source-detector distance for homogeneous reference measurements. The phase measurement should increase linearly with the source-detector distance. A piece-linear fitting method is implemented for the amplitude measurements of all remaining source-detector pairs in the reference data after outlier rejection. In general, three sections of shorter source-detector distance, mid-range, and longer distance range were used. If a measured logarithmic amplitude at a shorter source-detector distance does not follow the linear profile plotted as a function of the source-detector separation in the mid and longer range, we can assume that the PMT is saturated at this detector distance. The measurements that fit the linear profile are kept for further processing. Additionally, the phase data corresponding to the saturated amplitude data are not reliable and are removed from both reference and lesion data sets.

Besides the saturated measurements which often occur for source-detector pairs with shorter separation distances, there exist measurements of source-detector pairs with longer distances which are dominated by the noise of the system and are not reliable. To improve the reference data set, any measurements of longer source-detector pairs with amplitudes below the electronic noise of the system are classified as noisy measurements and expunged from the reference data. Since the corresponding phase data with amplitudes at noise level are not reliable, the both amplitude and phase data are removed from the reference data.

Iterative Reweighted Least Square Fitting

The MNR test is based on each source detector measurements separately and it removes the outliers at each source-detector pair. All reference measurements remaining after MNR and saturation data removal are fitted using an iterative reweighted least square (IRLS) method to obtain an accurate linear fit with the minimum fitting residue for both log scaled amplitude and phase measurements as functions of source and detector separation. Without being limited to any particular theory, this IRLS method has enhanced the quality of the results obtained in various p-norm minimization problems ranging from compressive sensing to baseline correction in industrial settings.

As shown in Eq. (13), IRLS iteratively minimizes the bi-square weighted residual in the least-square sense:

$$\beta_{n+1} = \Sigma_{i=1}^m w(i) \beta_n |y(i) - f(i,\beta)|^2. \quad \text{Eq. (13)}$$

where i is the index of the measurement, w is the bi-square weight function, y is the measurement value, $\beta$ includes slope and intercept of the line fitted to the data and f(i, $\beta$) is the fitted measurement based on the current $\beta$. This method reduces the influence of large residuals in the fitted reference parameters and improves the fitted results. After the fitting for both logarithmic amplitude and phase is completed, the distance of each amplitude and phase measurement from the corresponding value on the fitted line of same source-detector distance is calculated. All the measurements with higher absolute residue compared to the threshold in either amplitude or phase measurements are selected as non-accurate measurements and removed from the data set. In various embodiments, an absolute residue threshold of 0.5 is empirically selected for both amplitude and phase based on trial and error analysis using clinical data. Since the IRLS-based minimization is robust and less sensitive to noise bursts, this method further enhances the robustness of the data set selection.

Compound Reference Dataset

Even though accurately fitted lines for both log scaled amplitude and phase are obtained from the previous steps, there may still be more than one measurement for each remaining source-detector separation. In various embodiments, a single amplitude and phase measurement are selected for each source-detector pair to form a single robust reference data set. In various embodiments, a least square method is utilized to select the measurements with minimum distances from the center of the distribution of the remaining reference measurements for each source-detector pair. This selection process is performed separately on the remaining amplitude and phase data. Therefore, a final reference data set with high similarity to the fitted slope and intercept of the combination of all the reference data sets after outlier removal is produced. This reference data set consists of the selected amplitude and phase measurements for the remaining source-detector pairs. This robust set of reference measurements is referred to herein as the compound reference and is less sensitive to outliers, PMT saturation and noise.

Figure 17:
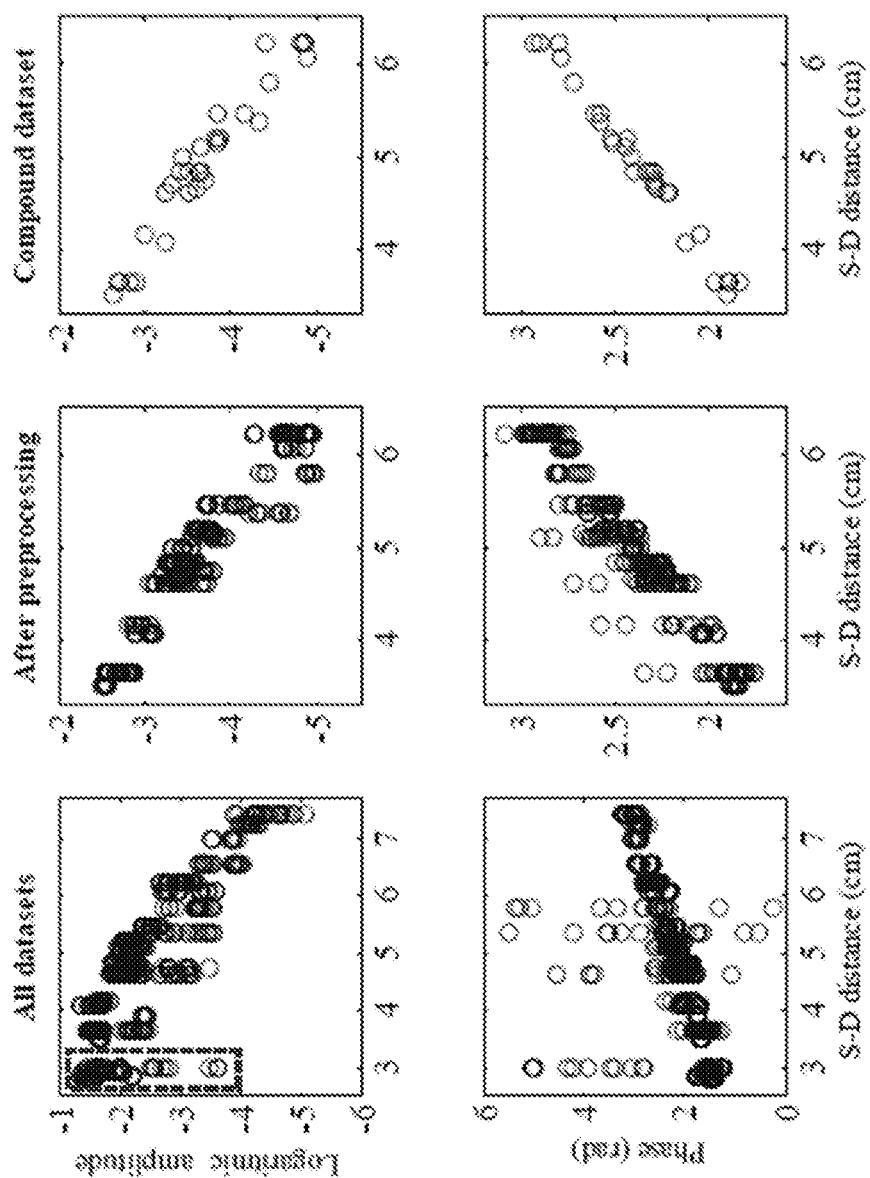

To visualize the effect of the proposed process, the amplitudes and phase profiles of one clinical case before and after preprocessing, as well as the final compound reference have been illustrated in FIG. 17. FIG. 17 shows log scaled amplitude and phase profiles of reference data sets before (left column) and after preprocessing (center column) as well as final compound reference (right column). Saturated source-detector pairs have been marked with an overlaid dashed rectangle in the amplitude part of the left column. The preprocessing includes outlier removal, saturation and noise rejection and iterative reweighted fitting with higher residue removal.

Perturbation Filtering

The procedures described above provide a robust set of reference measurements. For reconstruction of a lesion absorption map at each wavelength, the perturbation $U_{sc}$ is calculated by subtracting the compound reference from the lesion data as shown in Eq. (14), in which $A_l$ and $A_r$ are amplitude and pi and (fir are phase of each source-detector pair obtained at the lesion and compound reference, respectively:

$$U_{SC} = \frac{A_l(i) \cdot \exp(\varphi_l(i)) - A_r(i) \cdot \exp(\varphi_r(i))}{A_r(i) \cdot \exp(\varphi_r(i))} = \quad \text{Eq. (14)}$$
$$\left(\frac{A_l(i)}{A_r(i)} \cos(\varphi_l(i) - \varphi_r(i)) - 1\right) + j\left(\frac{A_l(i)}{A_r(i)} \sin(\varphi_l(i) - \varphi_r(i))\right)$$

Without being limited to any particular theory, outliers may occur in the perturbation data due to 1) measurements errors caused by movements of patient or operator's hand as well as bad coupling between the light guides and the breast; and/or 2) heterogeneity of the background tissue and the lesion. Lesion measurements are expected to be more heterogeneous than the reference measurements because the heterogeneity is partially caused by the lesion and partially by the background tissue heterogeneity. Therefore, outlier removal procedures applied to reference measurements, which include measurements of healthy tissues only, cannot be implemented to the lesion measurement dataset. Instead, a filtering method is applied to the perturbation based on constraints imposed on the phase difference between the lesion data and the reference data given in Eq. (14). These conditions are determined based on the predictions obtained from the semi-infinite analytical solution derived from diffusion approximation.

Simulations were performed using different background optical properties for both reference and lesion breasts as well as different optical properties for lesions of different sizes located at different depths. The simulations used the same probe geometry and the same number of the sources and detectors as the experiments. Table 9 shows the range of the parameters used for simulations. The results show that the maximum phase difference between lesion and reference measurements of all source detector pairs for most scenarios listed in Table 9 are in the range of few degrees.

For a 4 cm larger lesion of optical contrast of 10 times higher than the background, the maximum phase difference is only 22 degrees. This implies that the maximum phase difference of the source detector pairs cannot exceed 90 degrees even in extreme cases, and therefore the cosine term in Eq. (14) should always be positive. Consequently, the real part of the perturbation cannot be less than −1 assuming that the amplitude measured from lesion $A_l$ is smaller than that of the amplitude measured at reference $A_r$ due to a higher absorption of the lesion in general. Furthermore, the mean and the standard deviation of the imaginary part of the perturbation are calculated. If the imaginary part of a data point is farther than three standard deviations from the mean, it is classified an outlier. Any data points in the perturbation that do not meet both of these two criteria are classified as outliers and rejected from the perturbation. This step removes outliers in the perturbation likely caused by measurement errors rather than heterogeneity of the lesion data.

TABLE 9

Range of parameters used for analytical model and obtained maximum phase delay.

| Background $\mu_a$ | Background $\mu_s'$ | Lesion $\Delta\mu_a$ | Lesion depth | Lesion radius |
|---|---|---|---|---|
| 0.02–0.08 (cm$^{-1}$) | 5–10 (cm$^{-1}$) | 0.05–0.2 (cm$^{-1}$) | 1.5–3.5 (cm) | 0.5–2 (cm) |

This normalized perturbation is used for reconstructing the absorption map at each wavelength. A total hemoglobin map may be calculated from the combined data from the absorption maps summarizing absorption at four wavelengths.

In various embodiments, a dual-zone mesh scheme is used for the inversion aspect of the image reconstruction. Using the dual-zone mesh scheme, the imaging volume is segmented into two regions consisting of the lesion and background regions. These two regions are identified by a separate analysis of the co-registered ultrasound images. The dual-zone mesh scheme reduces the total number of voxels with unknown optical properties by using smaller mesh size for the lesion region and a larger coarse mesh size for the background region.

Any suitable method may be utilized for iterative optimization of the inverse problem to reconstruct the absorption maps based on the perturbation dataset including, but not limited to, a Newton method and a conjugated gradient method. In one aspect, a conjugate gradient method is utilized for iterative optimization of the inverse problem. Patient results are calculated from the selected data based on this automated outlier removal and data selection procedures.

Example 8: Iterative Imaging Reconstruction by Removing Measurement Outliers

In DOT image reconstruction, the scattered field, $U_{sc}$, or perturbation, which is the normalized difference between lesion breast and contralateral normal breast (reference) measurements, is used for mapping lesion absorption map at each wavelength. The total hemoglobin map is computed from the absorption maps of four optical wavelengths. Tissue heterogeneity, bad coupling between tissue and probe, and patient and operator's hand motions can contribute to the outliers in the perturbation measurements. These outlier measurements can cause image artifacts.

Figure 18:
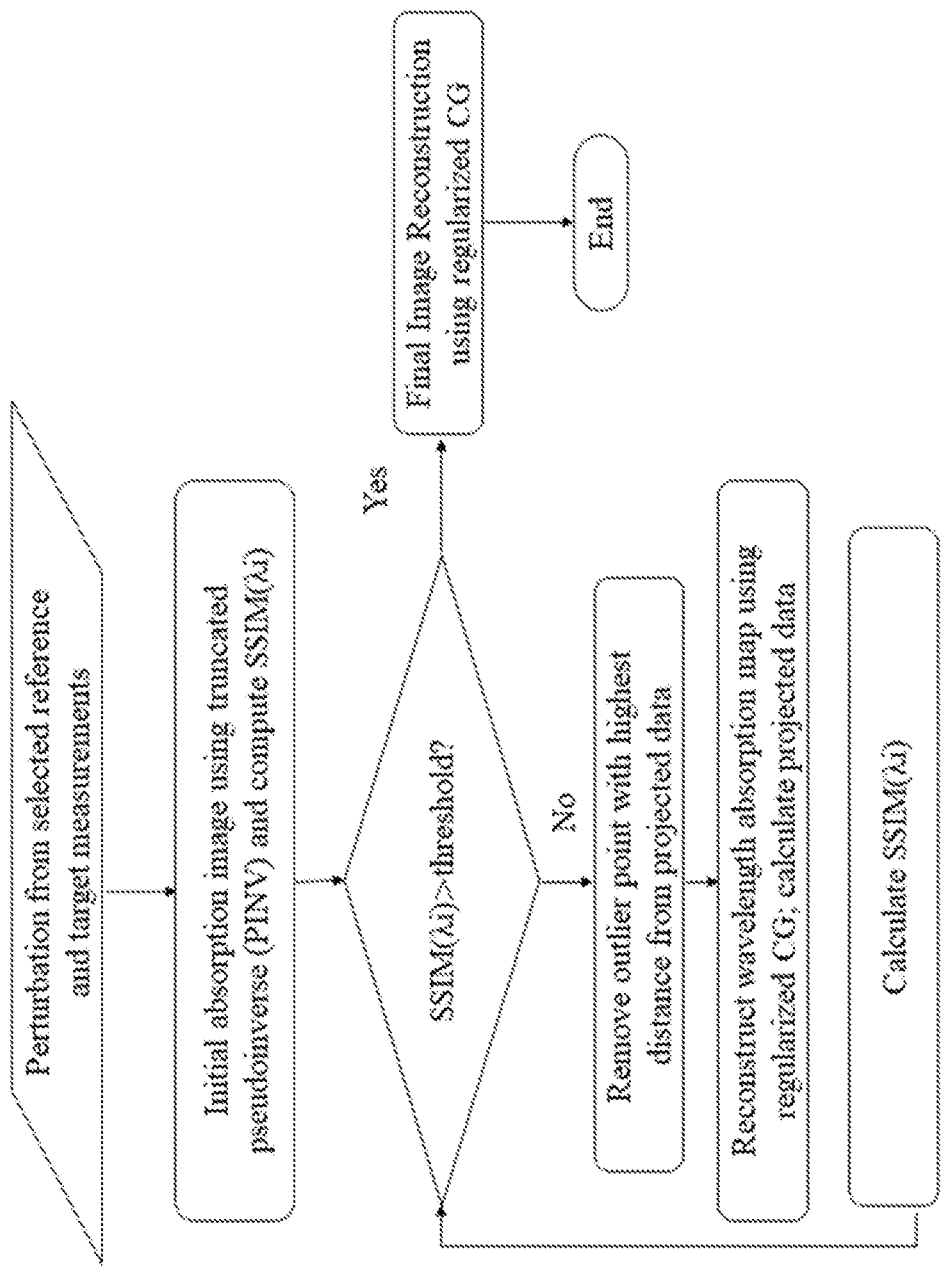
FIG. 18 is a flow chart illustrating an example automated method for generating optimized functional images that includes iterative perturbation corrections.

In various embodiments, a statistical method may be used to automatically remove outliers from contralateral normal breast measurements based on the semi-infinite medium model. However, this method cannot be used for perturbation measurements, because lesion measurements are expected to be more heterogeneous than the reference measurements. To separate the measurement errors from lesion heterogeneity, additional information from multiple wavelength measurements is incorporated in the preprocessing of the perturbation prior to the optimized image reconstruction. FIG. 18 is a flow chart illustrating shows a method for data preprocessing and an iterative perturbation correction algorithm. In this approach, a Structural Similarity Index (SSIM) is used to quantitatively evaluate imaging quality. The SSIM measure is a function of image luminance, contrast, and structure. SSIM between two images X and Y are defined as:

$$\text{SSIM}(X,Y) = [l(X,Y)]^\alpha \cdot [c(X,Y)]^\beta \cdot [s(X,Y)]^\gamma \qquad \text{Eq. (12)}$$

where l(X, Y), c(X, Y), and s(X, Y) are luminance, contrast and structure similarity respectively, and $\alpha>0$, $\beta>0$, $\gamma>0$ are three parameters used to adjust relative importance of luminance, contrast and structure similarity, respectively, in the similarity index. Luminance, contrast, and structure of two images are computed from the mean, standard deviation of normalized images according to Eq. (13):

$$l(X,Y) = (2\mu_X\mu_Y + C_1)/(\mu_X^2 + \mu_Y^2 + C_1)$$

$$c(X,Y) = (2\sigma_X\sigma_Y + C_2)/(\sigma_X^2 + \sigma_Y^2 + C_2)$$

$$s(X,Y) = (\sigma_{XY} + C_3)/(\sigma_X\sigma_Y + C_3) \qquad \text{Eq. (13)}$$

where $\mu_X$, $\mu_Y$, $\sigma_X$, $\sigma_Y$ and $\sigma_{XY}$ are mean of pixel values of image X, mean of pixel values of image Y, standard deviation of image X, standard deviation of image Y, and covariance of image X and Y respectively. $C_1$, $C_2$, $C_3$ are constants.

For each wavelength, $\lambda_i \in \{740 \text{ nm}, 780 \text{ nm}, 808 \text{ nm}, 830 \text{ nm}\}$, images at the other three wavelengths are used as references to compute SSIMs for three image pairs. An average of the resulting three SSIMs is the quantitative image quality index, SSIM($\lambda_i$), used to evaluate reconstructed image quality of wavelength $\lambda_i$ as given below:

$$SSIM(\lambda_i) = \frac{1}{n_{wavelength}-1} \sum_{j=1, j\neq i}^{n_{wavelength}} SSIM(\text{image}_i, \text{image}_j) \quad \text{Eq. (14)}$$

An iterative perturbation correction is performed based on $SSIM(\lambda_i)$ for each wavelength. Data at the wavelength with minimum $SSIM(\lambda_i)$ is corrected first. The initial estimate is produced by forming a truncated pseudoinverse (PINV) from the perturbation as described above. If the $SSIM(\lambda_i)$ is lower than a preset threshold (e.g., 0.9), perturbation from $\lambda_i$ wavelength is corrected based on the original perturbation and projected perturbation. The reconstructed image, $\delta\mu_a'$, for $\lambda_i$ is projected by multiplying weight matrix, W, to obtain the projected data according to Eq. (15):

$$[U_{projected}] = [W][\delta\mu_a'] \quad \text{Eq. (15)}$$

Based on the distance of original perturbation data, $U_{sc}$, and projected data, $U_{projected}$, a projection error, $E_{proj}$, is calculated as:

$$E_{proj} = \|U_{projected} - U_{sc}\|^2.$$

Each data point with maximum projection error is removed from $U_{sc}$. The modified perturbation is again used to reconstruct absorption map for wavelength $\lambda_i$ using regularized CG. $SSIM(\lambda_i)$ is recomputed again and compared with the threshold. This process is repeated until the lowest $SSIM(\lambda_i)$ is greater or equal to the threshold. This iterative correction procedure is performed for each wavelength until $SSIM(\lambda_i)$ for all four wavelengths are above the threshold.

Figures 19A, 19B, 19C:
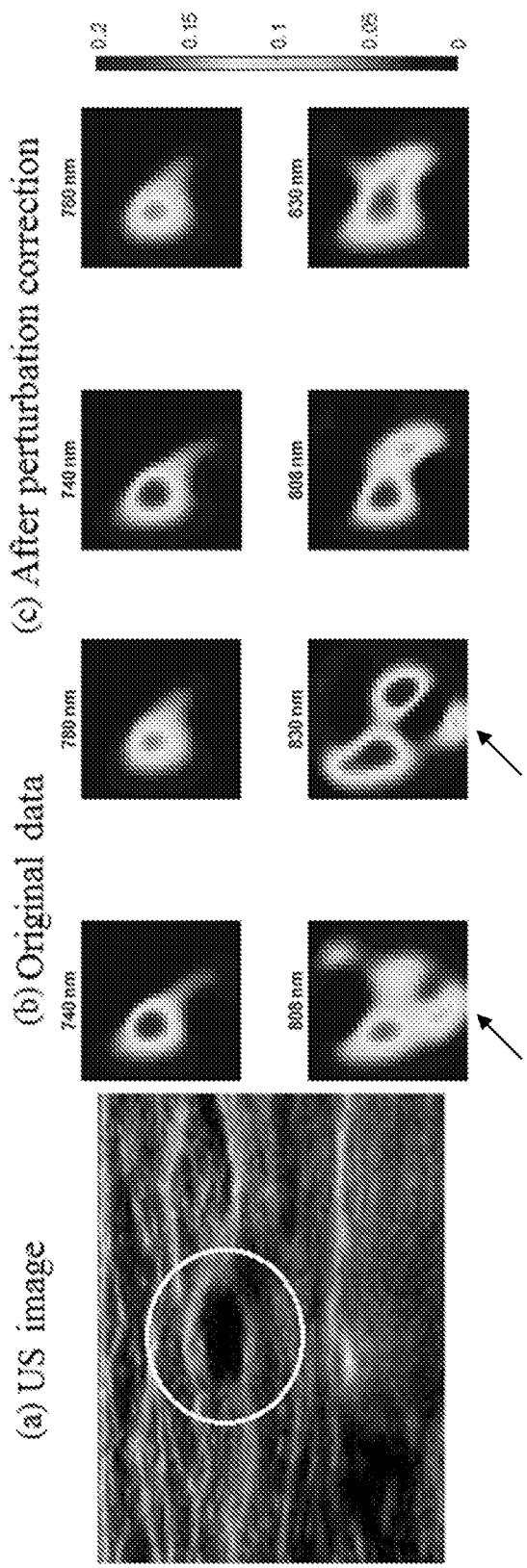
FIG. 19A is a ultrasound image of a patient.
FIG. 19B contains a series of absorption maps obtained at four wavelengths of various slices of the breast image of FIG. 19A based on data before perturbation correction.
FIG. 19C contains a series of absorption maps corresponding to the absorption maps of FIG. 19B after an iterative perturbation correction.

FIGS. 19A, 19B, and 19C show an example of the proposed iterative perturbation correction algorithm applied to an image of a breast lesion. FIG. 19A shows the ultrasound image with lesion marked by a white ellipse. FIG. 19B shows reconstructed absorption maps of four wavelengths. Each wavelength absorption map shows only 1 layer at depth of 1.5 cm. SSIM for the four wavelengths are 0.86, 0.84, 0.85, 0.81, respectively and the reconstructed maximum absorption coefficients are 0.251 cm$^{-1}$, 0.229 cm$^{-1}$, 0.244 cm$^{-1}$ and 0.318 cm$^{-1}$, respectively. Image artifacts are present in the 808 and 830 nm absorption maps as indicated by superimposed black arrows. FIG. 19C shows reconstructed absorption maps after the perturbation correction as described above. Mean SSIMs for the four wavelengths have improved to 0.93, 0.94, 0.93, 0.92, respectively while reconstructed maximum absorption coefficients became more consistent as 0.251 cm$^{-1}$, 0.229 cm$^{-1}$, 0.266 cm$^{-1}$ and 0.262 cm$^{-1}$, respectively.

Figures 20A, 20B, 20C:
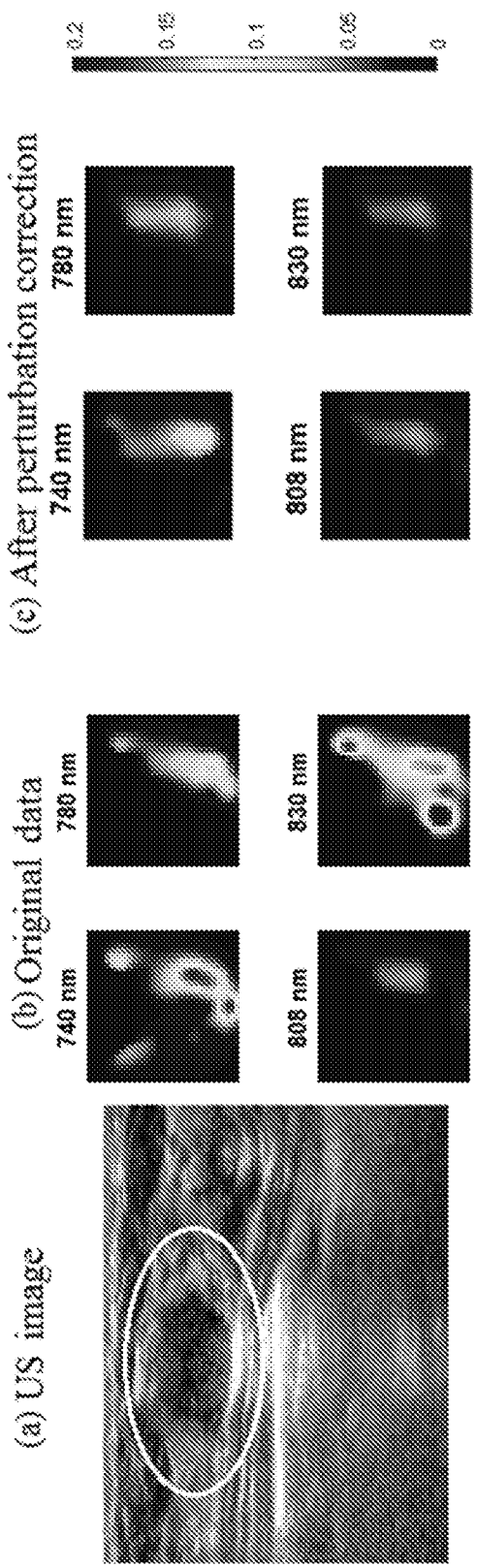
FIG. 20A is an ultrasound image of another patient.
FIG. 20B contains a series of absorption maps obtained at four wavelengths of various slices of the breast image of FIG. 20A based on data before perturbation correction.
FIG. 20C contains a series of absorption maps corresponding to the absorption maps of FIG. 19B after an iterative perturbation correction.

FIGS. 20A, 20B, and 20C show an example of the proposed iterative perturbation correction algorithm applied to an image of a normal breast. FIG. 20A shows the ultrasound image with lesion marked by an overlaid white ellipse. FIG. 20B shows reconstructed absorption maps for the four wavelengths. Each wavelength absorption map has one 2D layer at a depth of 1 cm. Mean SSIMs for the four wavelengths 740, 780, 808, 830 nm are 0.87, 0.91, 0.87, 0.82, respectively, and reconstructed absorption coefficients are 0.246 cm$^{-1}$, 0.207 cm$^{-1}$, 0.133 cm$^{-1}$ and 0.332 cm$^{-1}$, respectively. Image SSIM indicates that there is image artifact in wavelength 830 nm, which is confirmed by visual inspection. FIG. 3C shows reconstructed absorption maps after perturbation correction. Mean SSIMs for the four wavelengths change to 0.95, 0.97, 0.97, 0.96, respectively while the absorption coefficients change to 0.158 cm$^{-1}$, 0.147 cm$^{-1}$, 0.135 cm$^{-1}$ and 0.148 cm$^{-1}$, respectively.

This perturbation correction procedure is applicable to outlier removal caused by tissue heterogeneity, bad coupling between tissue and sources and detection fibers.

In operation, a computer executes computer-executable instructions embodied in one or more computer-executable components stored on one or more computer-readable media to implement aspects of the invention described and/or illustrated herein.

The order of execution or performance of the operations in embodiments of the invention illustrated and described herein is not essential, unless otherwise specified. That is, the operations may be performed in any order, unless otherwise specified, and embodiments of the invention may include additional or fewer operations than those disclosed herein. For example, it is contemplated that executing or performing a particular operation before, contemporaneously with, or after another operation is within the scope of aspects of the invention.

When introducing elements of aspects of the invention or the embodiments thereof, the articles "a," "an," "the," and "said" are intended to mean that there are one or more of the elements. The terms "comprising," "including," and "having" are intended to be inclusive and mean that there may be additional elements other than the listed elements.

Although described in connection with an exemplary computing system environment, embodiments of the invention are operational with numerous other general purpose or special purpose computing system environments or configurations. The computing system environment is not intended to suggest any limitation as to the scope of use or functionality of any aspect of the invention.

Embodiments of the invention may be described in the general context of computer-executable instructions, such as program modules, executed by one or more computers or other devices. The computer-executable instructions may be organized into one or more computer-executable components or modules. Generally, program modules include, but are not limited to, routines, programs, objects, components, and data structures that perform particular tasks or implement particular abstract data types. Aspects of the invention may be implemented with any number and organization of such components or modules. For example, aspects of the invention are not limited to the specific computer-executable instructions or the specific components or modules illustrated in the figures and described herein. Other embodiments of the invention may include different computer-executable instructions or components having more or less functionality than illustrated and described herein. Aspects of the invention may also be practiced in distributed computing environments where tasks are performed by remote processing devices that are linked through a communications network. In a distributed computing environment, program modules may be located in both local and remote computer storage media including memory storage devices.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A system for generating optimized functional images of a lesion region of a breast, the system comprising:

a diffuse optical tomography (DOT) device configured to acquire lesion functional data from the lesion region of the breast and to acquire reference functional data from a healthy tissue region of a contralateral breast;

a computing device in communication with the DOT device programmed to:
  transform the lesion functional data and the reference functional data to produce perturbation data, the perturbation data comprising a normalized difference between the lesion functional data and the reference functional data;
  generate a preliminary estimate of functional images by applying a truncated pseudoinverse matrix of a weight matrix to the perturbation data, the weight matrix comprising a plurality of elements representing system measurement sensitivity of the breast and distribution of diffused optical waves in a homogenous medium;
  generate the optimized functional images by iteratively optimizing successive estimates of the functional images regularized by the preliminary estimate of the functional images weighted by a regularization parameter, wherein a value of the optimized functional images at each voxel in the lesion region is indicative of a hemoglobin concentration at that voxel; and
  display the optimized functional images.

2. The system of claim 1, wherein the lesion functional data comprises first voxels of a fine voxel size within the lesion region and further comprises second voxels of a coarse voxel size greater than the fine voxel size in a background region adjacent to the lesion region.

3. The system of claim 1, wherein the truncated pseudoinverse matrix comprises a truncated Moore-Penrose pseudoinverse matrix.

4. The system of claim 3, wherein:
  the truncated Moore-Penrose pseudoinverse matrix comprises a pseudoinverse matrix of the weight matrix truncated to a truncated dimension;
  the truncated dimension comprises a number of singular values of the weight matrix greater than a threshold value; and
  the threshold value comprises a value of 10% of the largest singular value of the weight matrix.

5. The system of claim 1, wherein the functional images are optimized by a Newton method.

6. The system of claim 1, wherein the functional images are optimized by a conjugated gradient method.

7. The system of claim 1, wherein the optimized functional images comprise absorption maps, and the computing device is further programmed to:
  compute a total hemoglobin concentration based on the optimized functional images;
  indicate a level of malignancy based on a comparison of the total hemoglobin concentration with a threshold hemoglobin concentration; and
  generate a recommendation for biopsy based on the level of malignancy.

8. The system of claim 1, wherein the regularization parameter comprises the largest singular value of the weight matrix multiplied by a factor proportional to a tumor size.

9. A computer-implemented method of generating at least one optimized functional image of a lesion region of a breast of a subject comprising:
  receiving, using a computing device, a plurality of measurements from a diffuse optical tomography (DOT) device, the plurality of measurements comprising lesion functional data from the lesion region of the breast and reference functional data from a healthy tissue region of a contralateral breast;
  transforming, using the computing device, the lesion functional data and the reference functional data to produce perturbation data, the perturbation data comprising a normalized difference between the lesion functional data and the reference functional data;
  generating, using the computing device, a preliminary estimate of at least one functional image by applying a truncated pseudoinverse matrix of a weight matrix to the perturbation data, the weight matrix comprising a plurality of elements representing system measurement sensitivity of the breast and distribution of diffused optical waves in a homogenous medium;
  generating, using the computing device, the at least one optimized functional image by iteratively optimizing successive estimates of the at least one functional image regularized by the preliminary estimate of the at least one functional image weighted by a regularization parameter, wherein a value of the at least one optimized functional image at each voxel in the lesion region is indicative of a hemoglobin concentration at that voxel; and
  displaying the at least one optimized functional image on a display device.

10. The method of claim 9, wherein the lesion functional data comprises first voxels of a fine voxel size within the lesion region and further comprises second voxels of a coarse voxel size greater than the fine voxel size in a background region adjacent to the lesion region.

11. The method of claim 10, wherein generating a preliminary estimate comprises truncating, using the computing device, the pseudoinverse matrix of the weight matrix to a truncated dimension, wherein:
  the truncated dimension comprises a number of singular values of the weight matrix greater than a threshold value; and
  the threshold value comprises a value of 10% of the largest singular value of the weight matrix.

12. The method of claim 9, wherein the truncated pseudoinverse matrix comprises a truncated Moore-Penrose pseudoinverse matrix.

13. The method of claim 9, wherein generating the at least one optimized functional image comprises iteratively optimizing successive estimates of the at least one functional image, using the computing device, by an optimization method selected from a Newton method and a conjugated gradient method.

14. The method of claim 9, further comprising:
  computing, using the computing device, a total hemoglobin concentration based on the at least one optimized functional image;
  transforming, using the computing device, the total hemoglobin concentration to a level of malignancy by comparing the total hemoglobin concentration with a threshold hemoglobin concentration;
  generating, using the computing device, a recommendation for biopsy based on the level of malignancy; and
  displaying the recommendation for biopsy using a display device.

15. The method of claim 9, wherein selecting a regularization parameter comprises selecting a regularization parameter comprising the largest singular value of the weight matrix multiplied by a factor proportional to a tumor size.

16. A non-transitory computer readable medium that includes computer-executable instructions for generating at least one optimized functional image of a lesion region of a breast, wherein when executed by at least one processor of a computing device, the computer-executable instructions cause the at least one processor to:

receive a plurality of measurements from a diffuse optical tomography (DOT) device, the plurality of measurements comprising lesion functional data from the lesion region of the breast and reference functional data from a healthy tissue region of a contralateral breast;

transform the lesion functional data and the reference functional data to produce perturbation data, the perturbation data comprising a normalized difference between the lesion functional data and the reference functional data;

generate a preliminary estimate of at least one functional image by applying a truncated pseudoinverse matrix of a weight matrix to the perturbation data, the weight matrix comprising a plurality of elements representing system measurement sensitivity of the breast and distribution of diffused optical waves in a homogenous medium;

generate the at least one optimized functional image by iteratively optimizing successive estimates of the at least one functional image regularized by the preliminary estimate of the at least one functional image weighted by a regularization parameter, wherein a value of the optimized at least one functional image at each voxel in the lesion region is indicative of a hemoglobin concentration at that voxel; and display the at least one optimized functional image on a display device.

17. The non-transitory computer readable medium of claim 16, wherein the lesion functional data comprises first voxels of a fine voxel size within the lesion region and further comprises second voxels of a coarse voxel size greater than the fine voxel size in a background region adjacent to the lesion region.

18. The non-transitory computer readable medium of claim 16, wherein the truncated pseudoinverse matrix comprises a truncated Moore-Penrose pseudoinverse matrix, and the computer-executable instructions further cause the at least one processor to:

truncate the pseudoinverse matrix of the weight matrix to a truncated dimension, wherein:

the truncated dimension comprises a number of singular values of the weight matrix greater than a threshold value; and the threshold value comprises a value of 10% of the largest singular value of the weight matrix.

19. The non-transitory computer readable medium of claim 16, wherein the computer-executable instructions further cause the at least one processor to:

compute a total hemoglobin concentration based on the at least one optimized functional image;

indicate a level of malignancy based on a comparison of the total hemoglobin concentration with a threshold hemoglobin concentration; and generate a recommendation for biopsy based on the level of malignancy.

20. The non-transitory computer readable medium of claim 16, wherein the regularization parameter comprises the largest singular value of the weight matrix multiplied by a factor proportional to a tumor size.

\* \* \* \* \*